United States Patent
Saravia et al.

(10) Patent No.: US 9,155,574 B2
(45) Date of Patent: Oct. 13, 2015

(54) BONE FIXATION DEVICE, TOOLS AND METHODS

(75) Inventors: Heber Saravia, Santa Rosa, CA (US); Stephen R. McDaniel, Santa Rosa, CA (US); Trung Ho Pham, Santa Rosa, CA (US); Charles L. Nelson, Santa Rosa, CA (US); Stephen Gunther, Santa Rosa, CA (US)

(73) Assignee: Sonoma Orthopedic Products, Inc., Buffalo Grove, IL (US)

( * ) Notice: Subject to any disclaimer, the term of this patent is extended or adjusted under 35 U.S.C. 154(b) by 429 days.

(21) Appl. No.: 13/203,713

(22) PCT Filed: Sep. 28, 2009

(86) PCT No.: PCT/US2009/058632
§ 371 (c)(1),
(2), (4) Date: Jun. 6, 2012

(87) PCT Pub. No.: WO2010/037038
PCT Pub. Date: Apr. 1, 2010

(65) Prior Publication Data
US 2012/0239038 A1 Sep. 20, 2012

Related U.S. Application Data

(60) Provisional application No. 61/100,635, filed on Sep. 26, 2008, provisional application No. 61/100,652, filed on Sep. 26, 2008, provisional application No. 61/117,901, filed on Nov. 25, 2008, provisional application No. 61/122,563, filed on Dec. 15, 2008, provisional application No. 61/138,920, filed on Dec. 18, 2008.

(51) Int. Cl.
*A61B 17/72* (2006.01)
*A61B 17/88* (2006.01)
*A61B 17/17* (2006.01)
*A61B 17/00* (2006.01)

(52) U.S. Cl.
CPC .......... *A61B 17/7208* (2013.01); *A61B 17/1725* (2013.01); *A61B 17/7266* (2013.01);
(Continued)

(58) Field of Classification Search
CPC ....................... A61B 17/7002–17/7031; A61B 17/72–17/7291
USPC .................................. 606/62–68; 623/23.23
See application file for complete search history.

(56) References Cited

U.S. PATENT DOCUMENTS 958,127 A 5/1910 Hufrud
1,169,635 A 1/1916 Grimes
(Continued)

FOREIGN PATENT DOCUMENTS

CA 2561552 A1 11/2005
EP 1582163 A1 11/2003
(Continued)

OTHER PUBLICATIONS

Helical, May 17, 2014, Merriam-Webster, www.merriam-webster.com/dictionary/helical.*
Andermahr et al., "Anatomy of the clavicle and the intramedullary nailing of midclavicular fractures," Clinical Anatomy, vol. 20; pp. 48-56; 2007.
US 6,030,385, 02/2000, Faccioli et al. (withdrawn)

*Primary Examiner* — Jan Christopher Merene
*Assistant Examiner* — Steven Cotroneo
(74) *Attorney, Agent, or Firm* — Knobbe, Martens, Olson & Bear, LLP

(57) ABSTRACT

A bone fixation device is provided with an elongate body having a longitudinal axis and having a first state in which at least a portion of the body is flexible and a second state in which the body is generally rigid, an actuateable gripper disposed at one or more locations on the elongated body, a hub located on a proximal end of the elongated body, and an actuator operably connected to the gripper(s) to deploy the gripper(s) from a retracted configuration to an expanded configuration. Methods of repairing a fracture of a bone are also disclosed. One such method comprises inserting a bone fixation device into an intramedullary space of the bone to place at least a portion of an elongate body of the fixation device in a flexible state on one side of the fracture and at least a portion of a hub on another side of the fracture, and operating an actuator to deploy at least one gripper of the fixation device to engage an inner surface of the intramedullary space to anchor the fixation device to the bone. Alternative gripper designs are disclosed that may be used in various combinations.

21 Claims, 74 Drawing Sheets

(52) U.S. Cl.
CPC ......... *A61B17/8872* (2013.01); *A61B 17/7225* (2013.01); *A61B 17/7241* (2013.01); *A61B 2017/00004* (2013.01)

(56) References Cited

U.S. PATENT DOCUMENTS

| | | | |
|---|---|---|---|
| 1,790,841 A | 2/1931 | Rosen | |
| 2,502,267 A | 3/1950 | McPherson | |
| 2,685,877 A | 8/1954 | Dobelle | |
| 2,998,007 A | 8/1961 | Herzog | |
| 3,118,444 A | 1/1964 | Serrato, Jr. | |
| 3,441,017 A | 4/1969 | Kaessmann | |
| 3,626,935 A | 12/1971 | Pollock et al. | |
| 3,710,789 A | 1/1973 | Ersek | |
| 3,759,257 A | 9/1973 | Fischer et al. | |
| 3,760,802 A | 9/1973 | Fischer et al. | |
| 3,779,239 A | 12/1973 | Fischer et al. | |
| 3,791,380 A | 2/1974 | Dawidowski | |
| 3,846,846 A * | 11/1974 | Fischer | 623/23.18 |
| 3,955,565 A | 5/1976 | Johnson, Jr. | |
| 3,978,528 A | 9/1976 | Crep | |
| 3,986,504 A * | 10/1976 | Avila | 606/63 |
| 4,007,528 A | 2/1977 | Shea et al. | |
| 4,011,602 A | 3/1977 | Rybicki et al. | |
| 4,016,874 A | 4/1977 | Maffei et al. | |
| 4,050,464 A | 9/1977 | Hall | |
| 4,064,567 A | 12/1977 | Burstein et al. | |
| 4,065,816 A | 1/1978 | Sawyer | |
| 4,091,806 A | 5/1978 | Aginsky | |
| 4,146,022 A | 3/1979 | Johnson et al. | |
| 4,164,794 A | 8/1979 | Spector et al. | |
| 4,190,044 A | 2/1980 | Wood | |
| D255,048 S | 5/1980 | Miller | |
| 4,204,531 A | 5/1980 | Aginsky | |
| 4,227,518 A | 10/1980 | Aginsky | |
| 4,236,512 A | 12/1980 | Aginsky | |
| 4,237,875 A | 12/1980 | Tennanini | |
| 4,246,662 A | 1/1981 | Pastrick | |
| 4,262,665 A | 4/1981 | Roalstad et al. | |
| 4,275,717 A | 6/1981 | Bolesky | |
| 4,293,962 A | 10/1981 | Fuson | |
| 4,294,251 A | 10/1981 | Greenwald et al. | |
| 4,312,336 A | 1/1982 | Danieletto et al. | |
| 4,313,434 A | 2/1982 | Segal | |
| 4,338,926 A | 7/1982 | Kummer et al. | |
| 4,351,069 A | 9/1982 | Ballintyn et al. | |
| 4,352,212 A | 10/1982 | Greene et al. | |
| 4,353,358 A | 10/1982 | Emerson | |
| 4,379,451 A | 4/1983 | Getscher | |
| 4,409,974 A | 10/1983 | Freedland | |
| 4,453,539 A | 6/1984 | Raftopoulos et al. | |
| 4,457,301 A | 7/1984 | Walker | |
| 4,459,708 A | 7/1984 | Buttazzoni | |
| 4,462,394 A | 7/1984 | Jacobs | |
| 4,467,794 A | 8/1984 | Maffei et al. | |
| RE31,809 E | 1/1985 | Danieletto et al. | |
| 4,492,226 A | 1/1985 | Belykh et al. | |
| 4,503,847 A | 3/1985 | Mouradian | |
| 4,519,100 A | 5/1985 | Wills et al. | |
| 4,520,511 A | 6/1985 | Gianezio et al. | |
| 4,522,200 A | 6/1985 | Stednitz | |
| 4,541,423 A | 9/1985 | Barber | |
| 4,552,136 A | 11/1985 | Kenna | |
| 4,589,883 A | 5/1986 | Kenna | |
| 4,590,930 A | 5/1986 | Kurth et al. | |
| 4,604,997 A | 8/1986 | De Bastiani et al. | |
| 4,621,627 A | 11/1986 | De Bastiani et al. | |
| 4,622,959 A | 11/1986 | Marcus | |
| 4,624,673 A | 11/1986 | Meyer | |
| 4,628,920 A | 12/1986 | Mathys, Jr. et al. | |
| 4,632,101 A | 12/1986 | Freedland | |
| 4,643,177 A | 2/1987 | Sheppard et al. | |
| 4,651,724 A | 3/1987 | Berentey et al. | |
| 4,653,487 A | 3/1987 | Maale | |
| 4,662,887 A | 5/1987 | Tuner et al. | |
| 4,667,663 A | 5/1987 | Miyata | |
| D290,399 S | 6/1987 | Kitchens | |
| 4,681,590 A | 7/1987 | Tansey | |
| 4,697,585 A | 10/1987 | Williams | |
| 4,705,027 A | 11/1987 | Klaue | |
| 4,705,032 A | 11/1987 | Keller | |
| 4,721,103 A | 1/1988 | Freedland | |
| 4,735,625 A | 4/1988 | Davidson | |
| 4,753,657 A | 6/1988 | Lee et al. | |
| 4,776,330 A | 10/1988 | Chapman et al. | |
| 4,781,181 A | 11/1988 | Tanguy | |
| 4,805,595 A | 2/1989 | Kanbara | |
| 4,805,607 A | 2/1989 | Engelhardt et al. | |
| 4,813,963 A | 3/1989 | Hori et al. | |
| 4,817,591 A | 4/1989 | Klaue | |
| 4,827,919 A | 5/1989 | Barbarito et al. | |
| 4,828,277 A | 5/1989 | De Bastiani et al. | |
| 4,854,312 A | 8/1989 | Raftopoulos et al. | |
| 4,858,602 A | 8/1989 | Seidel et al. | |
| 4,862,883 A | 9/1989 | Freeland | |
| 4,871,369 A | 10/1989 | Muller | |
| 4,875,474 A | 10/1989 | Border | |
| 4,875,475 A | 10/1989 | Comte et al. | |
| 4,896,662 A | 1/1990 | Noble | |
| 4,921,499 A | 5/1990 | Hoffman et al. | |
| 4,927,424 A | 5/1990 | McConnell et al. | |
| 4,932,969 A | 6/1990 | Frey et al. | |
| 4,943,291 A | 7/1990 | Tanguy | |
| 4,946,179 A | 8/1990 | De Bastiani et al. | |
| 4,959,066 A | 9/1990 | Dunn et al. | |
| 4,969,889 A | 11/1990 | Greig | |
| 4,976,258 A | 12/1990 | Richter et al. | |
| 4,978,349 A | 12/1990 | Frigg | |
| 4,978,358 A | 12/1990 | Bobyn | |
| 4,988,349 A | 1/1991 | Pennig | |
| 5,002,547 A | 3/1991 | Poggie et al. | |
| 5,002,580 A | 3/1991 | Noble et al. | |
| 5,006,120 A | 4/1991 | Carter | |
| 5,013,314 A | 5/1991 | Firica et al. | |
| 5,019,077 A | 5/1991 | De Bastiani et al. | |
| 5,026,374 A | 6/1991 | Dezza et al. | |
| 5,027,799 A | 7/1991 | Laico et al. | |
| 5,030,222 A | 7/1991 | Calandruccio et al. | |
| 5,034,012 A | 7/1991 | Frigg | |
| 5,034,013 A | 7/1991 | Kyle et al. | |
| 5,035,697 A | 7/1991 | Frigg | |
| 5,037,423 A | 8/1991 | Kenna | |
| 5,041,114 A | 8/1991 | Chapman et al. | |
| 5,041,115 A | 8/1991 | Frigg et al. | |
| 5,053,035 A | 10/1991 | McLaren | |
| 5,057,103 A | 10/1991 | Davis | |
| 5,062,854 A | 11/1991 | Noble et al. | |
| 5,066,296 A | 11/1991 | Chapman et al. | |
| 5,084,050 A | 1/1992 | Draenert | |
| 5,092,892 A | 3/1992 | Ashby | |
| 5,098,433 A | 3/1992 | Freedland | |
| 5,100,404 A | 3/1992 | Hayes | |
| 5,102,413 A | 4/1992 | Poddar | |
| 5,108,404 A | 4/1992 | Scholten et al. | |
| 5,112,333 A | 5/1992 | Fixel | |
| 5,116,335 A | 5/1992 | Hannon et al. | |
| 5,116,380 A | 5/1992 | Hewka et al. | |
| 5,122,141 A | 6/1992 | Simpson et al. | |
| 5,122,146 A | 6/1992 | Chapman et al. | |
| 5,124,106 A | 6/1992 | Morr et al. | |
| 5,147,408 A | 9/1992 | Noble et al. | |
| 5,152,766 A | 10/1992 | Kirkley | |
| 5,163,963 A | 11/1992 | Hewka et al. | |
| 5,171,324 A | 12/1992 | Campana et al. | |
| 5,176,681 A | 1/1993 | Lawes et al. | |
| 5,178,621 A | 1/1993 | Cook et al. | |
| 5,190,544 A | 3/1993 | Chapman et al. | |
| 5,190,546 A | 3/1993 | Jervis | |
| 5,192,281 A | 3/1993 | de la Caffiniere | |
| 5,197,966 A | 3/1993 | Sommerkamp | |
| 5,197,990 A | 3/1993 | Lawes et al. | |
| 5,201,735 A | 4/1993 | Chapman et al. | |
| 5,201,767 A | 4/1993 | Caldarise et al. | |
| 5,211,664 A | 5/1993 | Tepic et al. | |

(56) References Cited

U.S. PATENT DOCUMENTS

| | | |
|---|---|---|
| 5,217,049 A | 6/1993 | Forsyth |
| 5,263,955 A | 11/1993 | Baumgart et al. |
| 5,268,000 A | 12/1993 | Ottieri et al. |
| 5,281,224 A | 1/1994 | Faccioli et al. |
| 5,281,225 A | 1/1994 | Vicenzi |
| 5,292,322 A | 3/1994 | Faccioli et al. |
| 5,295,991 A | 3/1994 | Frigg |
| 5,303,718 A | 4/1994 | Krajicek |
| 5,314,489 A | 5/1994 | Hoffman et al. |
| 5,320,622 A | 6/1994 | Faccioli et al. |
| 5,320,623 A | 6/1994 | Pennig |
| 5,326,376 A | 7/1994 | Warner et al. |
| 5,334,184 A | 8/1994 | Bimman |
| 5,342,360 A | 8/1994 | Faccioli et al. |
| 5,342,362 A | 8/1994 | Kenyon et al. |
| 5,346,496 A | 9/1994 | Pennig |
| 5,350,379 A | 9/1994 | Spievack |
| 5,352,227 A | 10/1994 | O'Hara |
| 5,358,534 A | 10/1994 | Dudasik et al. |
| 5,364,398 A | 11/1994 | Chapman et al. |
| 5,368,594 A | 11/1994 | Martin et al. |
| 5,376,090 A | 12/1994 | Pennig |
| 5,376,123 A | 12/1994 | Klaue et al. |
| 5,380,328 A | 1/1995 | Morgan |
| 5,383,932 A | 1/1995 | Wilson et al. |
| 5,387,243 A | 2/1995 | Devanathan |
| 5,397,328 A | 3/1995 | Behrens et al. |
| 5,403,321 A | 4/1995 | DiMarco |
| 5,411,503 A | 5/1995 | Hollstien et al. |
| 5,415,660 A | 5/1995 | Campbell et al. |
| 5,417,695 A | 5/1995 | Axelson, Jr. |
| RE34,985 E | 6/1995 | Pennig |
| 5,423,848 A | 6/1995 | Washizuka et al. |
| 5,423,850 A | 6/1995 | Berger |
| 5,433,718 A | 7/1995 | Brinker |
| 5,433,720 A | 7/1995 | Faccioli et al. |
| 5,441,500 A | 8/1995 | Seidel et al. |
| 5,443,477 A | 8/1995 | Marin et al. |
| 5,445,642 A | 8/1995 | McNulty et al. |
| 5,454,813 A | 10/1995 | Lawes |
| 5,454,816 A | 10/1995 | Ashby |
| 5,458,599 A | 10/1995 | Adobbati |
| 5,458,651 A | 10/1995 | Lawes |
| 5,458,653 A | 10/1995 | Davidson |
| 5,468,242 A | 11/1995 | Reisberg |
| 5,472,444 A | 12/1995 | Huebner et al. |
| 5,478,341 A | 12/1995 | Cook et al. |
| 5,480,400 A | 1/1996 | Berger |
| 5,484,438 A | 1/1996 | Pennig |
| 5,484,446 A | 1/1996 | Burke et al. |
| 5,488,761 A | 2/1996 | Leone |
| 5,490,852 A | 2/1996 | Azer et al. |
| 5,505,734 A | 4/1996 | Caniggia et al. |
| 5,514,137 A | 5/1996 | Coutts |
| 5,516,335 A | 5/1996 | Kummer et al. |
| 5,520,695 A | 5/1996 | Luckman |
| 5,527,316 A | 6/1996 | Stone et al. |
| 5,531,748 A | 7/1996 | de la Caffiniere |
| 5,534,004 A | 7/1996 | Santangelo |
| 5,545,162 A | 8/1996 | Huebner |
| 5,549,610 A | 8/1996 | Russell et al. |
| 5,549,706 A | 8/1996 | McCarthy |
| 5,554,192 A | 9/1996 | Crowninshield |
| 5,556,433 A | 9/1996 | Gabriel et al. |
| 5,562,667 A | 10/1996 | Shuler et al. |
| 5,562,673 A | 10/1996 | Koblish et al. |
| 5,562,674 A | 10/1996 | Stalcup et al. |
| 5,562,675 A | 10/1996 | McNulty et al. |
| 5,569,249 A | 10/1996 | James et al. |
| 5,571,189 A | 11/1996 | Kuslich |
| 5,571,204 A | 11/1996 | Nies |
| 5,573,536 A | 11/1996 | Grosse et al. |
| 5,578,035 A | 11/1996 | Lin |
| 5,586,985 A | 12/1996 | Putnam et al. |
| 5,591,169 A | 1/1997 | Benoist |
| 5,591,196 A | 1/1997 | Marin et al. |
| 5,593,451 A | 1/1997 | Averill et al. |
| 5,593,452 A | 1/1997 | Higham et al. |
| 5,605,713 A | 2/1997 | Boltong |
| 5,607,431 A | 3/1997 | Dudasik et al. |
| 5,613,970 A | 3/1997 | Houston et al. |
| 5,618,286 A | 4/1997 | Brinker |
| 5,618,300 A | 4/1997 | Marin et al. |
| 5,620,449 A | 4/1997 | Faccioli et al. |
| 5,624,440 A | 4/1997 | Huebner |
| 5,624,447 A | 4/1997 | Myers |
| 5,626,580 A | 5/1997 | Brosnahan |
| 5,643,258 A | 7/1997 | Robioneck et al. |
| 5,645,545 A | 7/1997 | Bryant |
| 5,645,599 A | 7/1997 | Samani |
| 5,658,283 A | 8/1997 | Huebner |
| 5,658,287 A | 8/1997 | Hofmann et al. |
| 5,658,292 A | 8/1997 | Axelson, Jr. |
| 5,658,293 A | 8/1997 | Vanlaningham |
| 5,658,351 A | 8/1997 | Dudasik et al. |
| 5,662,648 A | 9/1997 | Faccioli et al. |
| 5,662,649 A | 9/1997 | Huebner |
| 5,662,712 A | 9/1997 | Pathak et al. |
| 5,665,090 A | 9/1997 | Rockwood et al. |
| 5,665,091 A | 9/1997 | Noble et al. |
| 5,681,289 A | 10/1997 | Wilcox et al. |
| 5,681,316 A | 10/1997 | DeOrio et al. |
| 5,681,318 A | 10/1997 | Pennig et al. |
| 5,683,389 A | 11/1997 | Orsak |
| 5,683,460 A | 11/1997 | Persoons |
| 5,688,271 A | 11/1997 | Faccioli et al. |
| 5,688,279 A | 11/1997 | McNulty et al. |
| 5,690,634 A | 11/1997 | Muller et al. |
| 5,693,047 A | 12/1997 | Meyers et al. |
| 5,693,048 A | 12/1997 | Stalcup et al. |
| 5,695,729 A | 12/1997 | Chow et al. |
| 5,697,930 A | 12/1997 | Itoman et al. |
| 5,702,215 A | 12/1997 | Li |
| 5,702,481 A | 12/1997 | Lin |
| 5,702,487 A | 12/1997 | Averill et al. |
| 5,707,370 A | 1/1998 | Berki et al. |
| 5,718,704 A | 2/1998 | Medoff |
| 5,725,595 A | 3/1998 | Gustilo |
| 5,728,096 A | 3/1998 | Faccioli et al. |
| 5,741,256 A | 4/1998 | Bresina |
| 5,741,266 A | 4/1998 | Moran et al. |
| 5,749,872 A | 5/1998 | Kyle et al. |
| 5,749,880 A | 5/1998 | Banas et al. |
| 5,759,184 A | 6/1998 | Santangelo |
| 5,766,174 A | 6/1998 | Perry |
| 5,766,176 A | 6/1998 | Duncan |
| 5,766,178 A | 6/1998 | Michielli et al. |
| 5,766,179 A | 6/1998 | Faccioli et al. |
| 5,766,180 A | 6/1998 | Winquist |
| 5,772,662 A | 6/1998 | Chapman et al. |
| 5,772,663 A | 6/1998 | Whiteside et al. |
| 5,776,194 A | 7/1998 | Mikol et al. |
| 5,776,204 A | 7/1998 | Noble et al. |
| 5,779,703 A | 7/1998 | Benoist |
| 5,779,705 A | 7/1998 | Matthews |
| 5,782,921 A | 7/1998 | Colleran et al. |
| 5,785,057 A | 7/1998 | Fischer |
| 5,788,703 A | 8/1998 | Mittelmeier et al. |
| 5,807,241 A | 9/1998 | Heimberger |
| 5,810,750 A | 9/1998 | Buser |
| 5,810,820 A | 9/1998 | Santori et al. |
| 5,810,826 A | 9/1998 | Åkerfeldt et al. |
| 5,810,830 A | 9/1998 | Noble et al. |
| 5,814,047 A | 9/1998 | Emilio et al. |
| 5,814,681 A | 9/1998 | Hino et al. |
| 5,816,812 A | 10/1998 | Kownacki et al. |
| 5,827,282 A | 10/1998 | Pennig |
| 5,827,289 A | 10/1998 | Reiley et al. |
| 5,829,081 A | 11/1998 | Pearce |
| 5,836,949 A | 11/1998 | Campbell, Jr. et al. |
| 5,837,909 A | 11/1998 | Bill et al. |
| 5,849,004 A | 12/1998 | Bramlet |
| 5,849,014 A | 12/1998 | Mastrorio et al. |
| 5,849,035 A | 12/1998 | Pathak et al. |

(56) References Cited

U.S. PATENT DOCUMENTS

| | | |
|---|---|---|
| 5,855,581 A | 1/1999 | Koblish et al. |
| 5,858,020 A | 1/1999 | Johnson et al. |
| 5,863,295 A | 1/1999 | Averill et al. |
| 5,876,459 A | 3/1999 | Powell |
| 5,879,352 A * | 3/1999 | Filoso et al. ............ 606/62 |
| 5,881,878 A | 3/1999 | Faccioli et al. |
| 5,882,351 A | 3/1999 | Fox |
| 5,893,850 A | 4/1999 | Cachia |
| 5,895,390 A | 4/1999 | Moran et al. |
| 5,897,560 A | 4/1999 | Johnson |
| 5,902,302 A | 5/1999 | Berki et al. |
| 5,906,210 A | 5/1999 | Herbert |
| 5,908,422 A | 6/1999 | Bresina |
| 5,908,423 A | 6/1999 | Kashuba et al. |
| 5,912,410 A | 6/1999 | Cordell |
| 5,913,867 A | 6/1999 | Dion |
| 5,919,194 A | 7/1999 | Anderson |
| 5,925,048 A | 7/1999 | Ahmad et al. |
| 5,928,235 A | 7/1999 | Friedl |
| 5,928,240 A | 7/1999 | Johnson |
| 5,928,259 A | 7/1999 | Tovey |
| 5,931,830 A | 8/1999 | Jacobsen et al. |
| 5,931,839 A | 8/1999 | Medoff |
| 5,948,000 A | 9/1999 | Larsen et al. |
| 5,948,001 A | 9/1999 | Larsen |
| 5,951,556 A | 9/1999 | Faccioli et al. |
| 5,951,557 A | 9/1999 | Luter |
| 5,951,561 A | 9/1999 | Pepper et al. |
| 5,954,722 A | 9/1999 | Bono |
| 5,954,728 A | 9/1999 | Heller et al. |
| 5,961,553 A | 10/1999 | Coty et al. |
| 5,964,770 A | 10/1999 | Flomenblit et al. |
| 5,968,047 A | 10/1999 | Reed |
| 5,971,986 A | 10/1999 | Santori et al. |
| 5,976,134 A | 11/1999 | Huebner |
| 5,976,147 A | 11/1999 | LaSalle et al. |
| 5,976,188 A | 11/1999 | Dextradeur et al. |
| 5,989,260 A | 11/1999 | Yao |
| 5,989,261 A | 11/1999 | Walker et al. |
| 5,993,459 A | 11/1999 | Larsen et al. |
| 6,004,348 A | 12/1999 | Banas et al. |
| 6,010,505 A | 1/2000 | Asche et al. |
| 6,010,506 A | 1/2000 | Gosney et al. |
| 6,013,081 A | 1/2000 | Burkinshaw et al. |
| 6,015,413 A | 1/2000 | Faccioli et al. |
| 6,017,350 A | 1/2000 | Long |
| 6,018,094 A | 1/2000 | Fox |
| 6,019,761 A | 2/2000 | Gustilo |
| 6,019,762 A | 2/2000 | Cole |
| 6,020,396 A | 2/2000 | Jacobs |
| 6,024,745 A | 2/2000 | Faccioli et al. |
| 6,027,506 A | 2/2000 | Faccioli et al. |
| 6,027,534 A | 2/2000 | Wack et al. |
| 6,033,407 A | 3/2000 | Behrens |
| 6,039,742 A | 3/2000 | Krettek et al. |
| 6,045,556 A | 4/2000 | Cohen |
| 6,053,922 A * | 4/2000 | Krause et al. ............ 606/80 |
| 6,056,756 A | 5/2000 | Eng et al. |
| 6,074,392 A | 6/2000 | Durham |
| 6,077,264 A | 6/2000 | Chemello |
| 6,080,159 A | 6/2000 | Vichard |
| 6,083,522 A | 7/2000 | Chu et al. |
| 6,093,209 A | 7/2000 | Sanders |
| 6,096,040 A | 8/2000 | Esser |
| 6,102,911 A | 8/2000 | Faccioli et al. |
| 6,106,528 A | 8/2000 | Durham et al. |
| 6,120,504 A | 9/2000 | Brumback et al. |
| 6,120,509 A | 9/2000 | Wheeler |
| 6,126,661 A | 10/2000 | Faccioli et al. |
| 6,126,691 A | 10/2000 | Kasra et al. |
| 6,127,597 A | 10/2000 | Beyar et al. |
| 6,129,756 A | 10/2000 | Kugler et al. |
| 6,129,762 A | 10/2000 | Li |
| 6,139,583 A | 10/2000 | Johnson |
| 6,143,012 A | 11/2000 | Gausepohl |
| 6,143,033 A | 11/2000 | Paul et al. |
| 6,162,223 A | 12/2000 | Orsak et al. |
| 6,162,226 A | 12/2000 | DeCarlo et al. |
| 6,168,595 B1 | 1/2001 | Durham et al. |
| 6,168,632 B1 | 1/2001 | Moser et al. |
| 6,171,309 B1 | 1/2001 | Huebner |
| 6,176,871 B1 | 1/2001 | Pathak et al. |
| 6,179,839 B1 | 1/2001 | Weiss et al. |
| 6,179,842 B1 | 1/2001 | Spotomo et al. |
| 6,183,470 B1 | 2/2001 | Booth, Jr. et al. |
| 6,197,029 B1 | 3/2001 | Fujimori et al. |
| 6,197,031 B1 | 3/2001 | Barrette et al. |
| 6,200,321 B1 | 3/2001 | Orbay et al. |
| 6,206,880 B1 | 3/2001 | Karladani |
| 6,221,036 B1 | 4/2001 | Lucas |
| 6,221,074 B1 | 4/2001 | Cole et al. |
| 6,224,600 B1 | 5/2001 | Protogirou |
| 6,224,609 B1 | 5/2001 | Ressemann et al. |
| 6,228,123 B1 | 5/2001 | Dezzani |
| 6,231,576 B1 | 5/2001 | Frigg et al. |
| 6,235,029 B1 | 5/2001 | Faccioli et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,261,289 B1 | 7/2001 | Levy |
| 6,270,499 B1 | 8/2001 | Leu et al. |
| 6,273,876 B1 | 8/2001 | Klima et al. |
| 6,273,892 B1 | 8/2001 | Orbay et al. |
| 6,280,456 B1 | 8/2001 | Scribner et al. |
| 6,280,474 B1 | 8/2001 | Cassidy et al. |
| 6,283,969 B1 | 9/2001 | Grusin et al. |
| 6,287,310 B1 | 9/2001 | Fox |
| 6,290,725 B1 | 9/2001 | Weiss et al. |
| 6,296,603 B1 | 10/2001 | Turnlund et al. |
| 6,296,645 B1 | 10/2001 | Hover et al. |
| 6,299,642 B1 | 10/2001 | Chan |
| 6,309,396 B1 | 10/2001 | Ritland |
| 6,319,253 B1 | 11/2001 | Ackeret et al. |
| 6,325,830 B1 | 12/2001 | Mastorio et al. |
| 6,332,886 B1 | 12/2001 | Green et al. |
| 6,336,929 B1 | 1/2002 | Justin |
| 6,348,053 B1 | 2/2002 | Cachia |
| 6,355,042 B2 | 3/2002 | Winquist et al. |
| 6,355,044 B1 | 3/2002 | Hair |
| 6,355,069 B1 | 3/2002 | DeCarlo et al. |
| 6,358,250 B1 | 3/2002 | Orbay |
| 6,358,283 B1 | 3/2002 | Hogfors et al. |
| 6,364,824 B1 | 4/2002 | Fitzsimmons |
| 6,364,882 B1 | 4/2002 | Orbay |
| 6,364,909 B1 | 4/2002 | McGee |
| 6,379,359 B1 | 4/2002 | Dahners |
| 6,379,360 B1 | 4/2002 | Ackeret et al. |
| 6,383,188 B2 | 5/2002 | Kuslich et al. |
| 6,395,004 B1 | 5/2002 | Dye et al. |
| 6,402,753 B1 | 6/2002 | Cole et al. |
| 6,406,477 B1 | 6/2002 | Fujiwara |
| 6,416,516 B1 | 7/2002 | Stauch et al. |
| 6,423,083 B2 | 7/2002 | Reiley et al. |
| 6,423,096 B1 | 7/2002 | Musset et al. |
| 6,425,923 B1 | 7/2002 | Stalcup et al. |
| 6,436,148 B1 | 8/2002 | DeCarlo, Jr. et al. |
| 6,440,135 B2 | 8/2002 | Orbay et al. |
| 6,443,954 B1 | 9/2002 | Bramlet et al. |
| 6,443,992 B2 | 9/2002 | Lubinus |
| 6,447,513 B1 | 9/2002 | Griggs |
| 6,447,514 B1 | 9/2002 | Stalcup et al. |
| 6,447,515 B1 | 9/2002 | Meldrum |
| 6,447,518 B1 | 9/2002 | Krause et al. |
| 6,461,358 B1 | 10/2002 | Faccioli et al. |
| 6,461,360 B1 | 10/2002 | Adam |
| 6,468,278 B1 | 10/2002 | Muckter |
| 6,488,684 B2 | 12/2002 | Bramlet et al. |
| 6,491,694 B1 | 12/2002 | Orsak |
| 6,500,209 B1 | 12/2002 | Kolb |
| 6,508,819 B1 | 1/2003 | Orbay |
| 6,508,820 B2 | 1/2003 | Bales |
| 6,511,481 B2 | 1/2003 | von Hoffmann et al. |
| 6,520,994 B2 | 2/2003 | Nogarin |
| 6,524,313 B1 | 2/2003 | Fassier et al. |

(56) References Cited

U.S. PATENT DOCUMENTS

| | | | |
|---|---|---|---|
| 6,527,775 B1 | 3/2003 | Warburton |
| 6,530,925 B2 | 3/2003 | Boudard et al. |
| 6,533,788 B1 | 3/2003 | Orbay |
| 6,537,275 B2 | 3/2003 | Venturini et al. |
| 6,540,752 B1 | 4/2003 | Hicken et al. |
| 6,544,265 B2 | 4/2003 | Lieberman |
| 6,551,319 B2 | 4/2003 | Lieberman |
| 6,551,321 B1 | 4/2003 | Burkinshaw et al. |
| 6,554,833 B2 | 4/2003 | Levy et al. |
| 6,554,862 B2 | 4/2003 | Hays et al. |
| 6,558,388 B1 * | 5/2003 | Bartsch et al. | 606/62 |
| 6,562,042 B2 | 5/2003 | Nelson |
| 6,565,573 B1 | 5/2003 | Ferrante et al. |
| 6,572,620 B1 | 6/2003 | Schon et al. |
| 6,575,973 B1 | 6/2003 | Shekalim |
| 6,575,986 B2 | 6/2003 | Overaker |
| 6,575,994 B1 | 6/2003 | Marin et al. |
| 6,582,453 B1 | 6/2003 | Tran et al. |
| 6,592,578 B2 | 7/2003 | Henniges et al. |
| 6,607,531 B2 | 8/2003 | Frigg |
| 6,613,052 B1 | 9/2003 | Kinnett |
| 6,616,667 B1 | 9/2003 | Steiger et al. |
| 6,616,742 B2 | 9/2003 | Lin et al. |
| 6,620,197 B2 | 9/2003 | Maroney et al. |
| 6,623,487 B1 | 9/2003 | Goshert |
| 6,629,976 B1 | 10/2003 | Gnos et al. |
| 6,632,224 B2 | 10/2003 | Cachia et al. |
| 6,632,235 B2 | 10/2003 | Weikel et al. |
| 6,641,596 B1 | 11/2003 | Uzardi |
| 6,648,889 B2 | 11/2003 | Bramlet et al. |
| 6,648,890 B2 | 11/2003 | Culbert et al. |
| 6,648,893 B2 | 11/2003 | Dudasik |
| 6,652,529 B2 | 11/2003 | Swanson |
| 6,652,591 B2 | 11/2003 | Serbousek et al. |
| 6,656,189 B1 | 12/2003 | Wilson et al. |
| 6,663,647 B2 | 12/2003 | Reiley et al. |
| 6,679,890 B2 | 1/2004 | Margulies et al. |
| 6,682,568 B2 | 1/2004 | Despres, III et al. |
| 6,685,679 B2 | 2/2004 | Merdan |
| 6,685,706 B2 | 2/2004 | Padget et al. |
| 6,688,822 B2 | 2/2004 | Ritter et al. |
| 6,692,530 B2 | 2/2004 | Doubler et al. |
| 6,694,667 B2 | 2/2004 | Davis |
| 6,695,844 B2 | 2/2004 | Bramlet et al. |
| 6,699,251 B1 | 3/2004 | Venturini |
| 6,699,253 B2 | 3/2004 | McDowell et al. |
| 6,706,046 B2 | 3/2004 | Orbay et al. |
| 6,706,072 B2 | 3/2004 | Dwyer et al. |
| 6,709,436 B1 | 3/2004 | Hover et al. |
| 6,712,820 B2 | 3/2004 | Orbay |
| 6,719,793 B2 | 4/2004 | McGee |
| 6,722,368 B1 | 4/2004 | Shaikh |
| 6,723,129 B2 | 4/2004 | Dwyer et al. |
| 6,730,087 B1 | 5/2004 | Butsch |
| 6,730,090 B2 | 5/2004 | Orbay et al. |
| 6,736,818 B2 | 5/2004 | Perren et al. |
| 6,749,611 B2 | 6/2004 | Venturini et al. |
| 6,749,614 B2 | 6/2004 | Teitelbaum et al. |
| 6,755,831 B2 | 6/2004 | Putnam et al. |
| 6,755,862 B2 | 6/2004 | Keynan |
| 6,755,866 B2 | 6/2004 | Southworth |
| 6,767,350 B1 | 7/2004 | Lob |
| 6,767,351 B2 | 7/2004 | Orbay et al. |
| 6,780,185 B2 | 8/2004 | Frei et al. |
| 6,783,529 B2 | 8/2004 | Hover et al. |
| 6,783,530 B1 | 8/2004 | Levy |
| 6,783,533 B2 | 8/2004 | Green et al. |
| 6,786,908 B2 | 9/2004 | Hover et al. |
| 6,790,210 B1 | 9/2004 | Cragg et al. |
| 6,793,655 B2 | 9/2004 | Orsak |
| 6,793,659 B2 | 9/2004 | Putnam |
| 6,808,527 B2 | 10/2004 | Lower et al. |
| 6,821,277 B2 | 11/2004 | Teitelbaum |
| 6,821,299 B2 | 11/2004 | Kirking et al. |
| 6,827,739 B2 | 12/2004 | Griner et al. |
| 6,827,741 B2 | 12/2004 | Reeder |
| 6,840,939 B2 | 1/2005 | Venturini et al. |
| 6,855,146 B2 | 2/2005 | Frigg et al. |
| 6,855,167 B2 | 2/2005 | Shimp et al. |
| 6,863,692 B2 | 3/2005 | Meulink |
| 6,866,455 B2 | 3/2005 | Hasler |
| 6,866,665 B2 | 3/2005 | Orbay |
| 6,875,212 B2 | 4/2005 | Shaolian et al. |
| 6,887,243 B2 | 5/2005 | Culbert |
| 6,887,271 B2 | 5/2005 | Justin et al. |
| 6,887,276 B2 | 5/2005 | Gerbec et al. |
| 6,890,333 B2 | 5/2005 | von Hoffmann et al. |
| 6,893,444 B2 | 5/2005 | Orbay |
| 6,899,713 B2 | 5/2005 | Shaolian et al. |
| 6,899,719 B2 | 5/2005 | Reiley et al. |
| 6,902,583 B2 | 6/2005 | Gerbec et al. |
| 6,908,465 B2 | 6/2005 | von Hoffmann et al. |
| 6,916,323 B2 | 7/2005 | Kitchens |
| 6,921,397 B2 | 7/2005 | Corcoran et al. |
| 6,926,720 B2 | 8/2005 | Castaneda |
| 6,926,741 B2 | 8/2005 | Kolb |
| 6,929,692 B2 | 8/2005 | Tas |
| 6,942,666 B2 | 9/2005 | Overaker et al. |
| 6,942,668 B2 | 9/2005 | Padget et al. |
| 6,949,100 B1 | 9/2005 | Venturini |
| 6,949,124 B2 | 9/2005 | Serbousek et al. |
| 6,951,561 B2 | 10/2005 | Warren et al. |
| 6,974,482 B2 | 12/2005 | Zhu |
| 6,981,981 B2 | 1/2006 | Reiley et al. |
| 6,986,771 B2 | 1/2006 | Paul et al. |
| 6,999,819 B2 | 2/2006 | Swoyer et al. |
| 7,001,386 B2 | 2/2006 | Sohngen et al. |
| 7,001,388 B2 | 2/2006 | Orbay et al. |
| D518,174 S | 3/2006 | Venturini et al. |
| 7,008,425 B2 | 3/2006 | Phillips |
| 7,008,428 B2 | 3/2006 | Cachia et al. |
| 7,008,451 B2 | 3/2006 | Justin et al. |
| 7,011,664 B2 | 3/2006 | Haney et al. |
| 7,012,106 B2 | 3/2006 | Yuan et al. |
| 7,029,476 B2 | 4/2006 | Hansson |
| 7,029,478 B2 | 4/2006 | Hollstien et al. |
| 7,033,363 B2 | 4/2006 | Powell |
| 7,033,365 B2 | 4/2006 | Powell et al. |
| 7,041,104 B1 | 5/2006 | Cole et al. |
| 7,044,978 B2 | 5/2006 | Howie et al. |
| 7,052,498 B2 * | 5/2006 | Levy et al. | 606/63 |
| 7,056,322 B2 | 6/2006 | Davison et al. |
| 7,060,075 B2 | 6/2006 | Govari et al. |
| 7,070,601 B2 | 7/2006 | Culbert et al. |
| 7,070,616 B2 | 7/2006 | Majercak et al. |
| 7,074,224 B2 | 7/2006 | Daniels et al. |
| 7,081,119 B2 | 7/2006 | Stihl |
| 7,083,624 B2 | 8/2006 | Irving |
| 7,090,676 B2 | 8/2006 | Huebner et al. |
| 7,097,648 B1 | 8/2006 | Globerman et al. |
| 7,097,664 B2 | 8/2006 | Despres, III et al. |
| RE39,301 E | 9/2006 | Bertin |
| 7,101,376 B2 | 9/2006 | Semet |
| 7,118,574 B2 | 10/2006 | Patel et al. |
| 7,122,056 B2 | 10/2006 | Dwyer et al. |
| 7,137,987 B2 | 11/2006 | Patterson et al. |
| 7,141,052 B2 | 11/2006 | Manderson |
| 7,141,067 B2 | 11/2006 | Jones et al. |
| 7,144,399 B2 | 12/2006 | Hayes et al. |
| 7,147,639 B2 | 12/2006 | Berki et al. |
| 7,147,640 B2 | 12/2006 | Huebner et al. |
| 7,153,309 B2 | 12/2006 | Huebner et al. |
| 7,156,852 B2 | 1/2007 | Dye et al. |
| 7,160,302 B2 | 1/2007 | Warburton |
| 7,160,333 B2 | 1/2007 | Plouhar et al. |
| 7,163,563 B2 | 1/2007 | Schwartz et al. |
| 7,175,625 B2 | 2/2007 | Culbert |
| 7,175,631 B2 | 2/2007 | Wilson et al. |
| 7,179,260 B2 | 2/2007 | Gerlach et al. |
| 7,188,687 B2 | 3/2007 | Rudd et al. |
| 7,189,237 B2 | 3/2007 | Huebner |
| 7,632,277 B2 | 12/2009 | Woll et al. |
| 7,846,162 B2 | 12/2010 | Nelson et al. |
| 7,909,825 B2 | 3/2011 | Saravia et al. |

(56) References Cited

U.S. PATENT DOCUMENTS

| | | |
|---|---|---|
| 7,914,533 B2 | 3/2011 | Nelson et al. |
| 7,942,875 B2 | 5/2011 | Nelson et al. |
| 2001/0011174 A1 | 8/2001 | Reiley et al. |
| 2001/0034526 A1 | 10/2001 | Kuslich et al. |
| 2001/0049531 A1 | 12/2001 | Reiley et al. |
| 2002/0004685 A1 | 1/2002 | White |
| 2002/0029041 A1 | 3/2002 | Hover et al. |
| 2002/0032444 A1 | 3/2002 | Mische |
| 2002/0041896 A1 | 4/2002 | Straub et al. |
| 2002/0068939 A1 | 6/2002 | Levy et al. |
| 2002/0068981 A1 | 6/2002 | Hajianpour |
| 2002/0095214 A1 | 7/2002 | Hyde, Jr. |
| 2002/0099385 A1 | 7/2002 | Ralph et al. |
| 2002/0103488 A1 | 8/2002 | Lower et al. |
| 2002/0143344 A1 | 10/2002 | Taylor |
| 2002/0161369 A1 | 10/2002 | Bramlet et al. |
| 2002/0165544 A1 | 11/2002 | Perren et al. |
| 2002/0173792 A1 | 11/2002 | Severns et al. |
| 2002/0177866 A1 | 11/2002 | Weikel et al. |
| 2002/0188297 A1 | 12/2002 | Dakin et al. |
| 2002/0198526 A1 | 12/2002 | Shaolian et al. |
| 2003/0032960 A1 | 2/2003 | Dudasik |
| 2003/0040752 A1 | 2/2003 | Kitchens |
| 2003/0045919 A1 | 3/2003 | Swoyer et al. |
| 2003/0073999 A1* | 4/2003 | Putnam .......................... 606/62 |
| 2003/0074075 A1 | 4/2003 | Thomas, Jr. et al. |
| 2003/0078669 A1 | 4/2003 | Martin et al. |
| 2003/0097136 A1 | 5/2003 | Hajianpour |
| 2003/0109932 A1 | 6/2003 | Keynan |
| 2003/0130660 A1 | 7/2003 | Levy et al. |
| 2003/0130664 A1 | 7/2003 | Boucher et al. |
| 2003/0139802 A1 | 7/2003 | Wulfman et al. |
| 2003/0181918 A1 | 9/2003 | Smothers et al. |
| 2003/0216738 A1 | 11/2003 | Azar |
| 2003/0236529 A1 | 12/2003 | Shluzas et al. |
| 2004/0006341 A1 | 1/2004 | Shaolian et al. |
| 2004/0010263 A1 | 1/2004 | Boucher et al. |
| 2004/0098017 A1 | 5/2004 | Saab et al. |
| 2004/0098134 A1 | 5/2004 | Meulink |
| 2004/0133204 A1 | 7/2004 | Davies |
| 2004/0133280 A1 | 7/2004 | Trieu |
| 2004/0153114 A1 | 8/2004 | Reiley et al. |
| 2004/0153115 A1 | 8/2004 | Reiley et al. |
| 2004/0167561 A1 | 8/2004 | Boucher et al. |
| 2004/0193255 A1 | 9/2004 | Shanley et al. |
| 2004/0193267 A1 | 9/2004 | Jones et al. |
| 2004/0213825 A1 | 10/2004 | Levy |
| 2004/0214311 A1 | 10/2004 | Levy |
| 2004/0215193 A1 | 10/2004 | Shaolian et al. |
| 2004/0230193 A1 | 11/2004 | Cheung et al. |
| 2004/0236327 A1 | 11/2004 | Paul et al. |
| 2004/0260398 A1 | 12/2004 | Kelman |
| 2004/0267269 A1 | 12/2004 | Middleton et al. |
| 2004/0267271 A9 | 12/2004 | Scribner et al. |
| 2005/0015154 A1 | 1/2005 | Lindsey et al. |
| 2005/0027294 A1 | 2/2005 | Woll et al. |
| 2005/0027301 A1 | 2/2005 | Stihl |
| 2005/0043737 A1 | 2/2005 | Reiley et al. |
| 2005/0043757 A1 | 2/2005 | Arad et al. |
| 2005/0047892 A1 | 3/2005 | Bremner |
| 2005/0055023 A1 | 3/2005 | Sohngen et al. |
| 2005/0055024 A1 | 3/2005 | James et al. |
| 2005/0080425 A1 | 4/2005 | Bhatnagar et al. |
| 2005/0090852 A1 | 4/2005 | Layne et al. |
| 2005/0107883 A1 | 5/2005 | Goodfried et al. |
| 2005/0119662 A1 | 6/2005 | Reiley et al. |
| 2005/0131386 A1 | 6/2005 | Freeman et al. |
| 2005/0143827 A1 | 6/2005 | Globerman et al. |
| 2005/0149022 A1 | 7/2005 | Shaolian et al. |
| 2005/0149024 A1 | 7/2005 | Ferrante et al. |
| 2005/0149025 A1 | 7/2005 | Ferrante et al. |
| 2005/0159749 A1 | 7/2005 | Levy et al. |
| 2005/0165395 A1 | 7/2005 | Orbay et al. |
| 2005/0171552 A1 | 8/2005 | Johnson et al. |
| 2005/0171563 A1 | 8/2005 | Heinrich et al. |
| 2005/0177158 A1 | 8/2005 | Doubler et al. |
| 2005/0203510 A1 | 9/2005 | Sohngen et al. |
| 2005/0209595 A1 | 9/2005 | Karmon |
| 2005/0216007 A1 | 9/2005 | Woll et al. |
| 2005/0228391 A1 | 10/2005 | Levy et al. |
| 2005/0234453 A1 | 10/2005 | Shaolian et al. |
| 2005/0234559 A1 | 10/2005 | Fernandez et al. |
| 2005/0251140 A1 | 11/2005 | Shaolian et al. |
| 2005/0261781 A1 | 11/2005 | Sennett et al. |
| 2005/0267481 A1 | 12/2005 | Carl et al. |
| 2005/0267483 A1 | 12/2005 | Middleton |
| 2005/0267586 A1 | 12/2005 | Sidebotham |
| 2005/0283250 A1 | 12/2005 | Coon et al. |
| 2005/0288678 A1 | 12/2005 | Reilley et al. |
| 2006/0004465 A1 | 1/2006 | Bergin et al. |
| 2006/0015101 A1 | 1/2006 | Warburton et al. |
| 2006/0015123 A1 | 1/2006 | Fencl et al. |
| 2006/0030945 A1 | 2/2006 | Wright |
| 2006/0036248 A1 | 2/2006 | Ferrante |
| 2006/0052788 A1 | 3/2006 | Thelen et al. |
| 2006/0064094 A1 | 3/2006 | Levy et al. |
| 2006/0084997 A1 | 4/2006 | Dejardin |
| 2006/0084998 A1 | 4/2006 | Levy et al. |
| 2006/0122601 A1 | 6/2006 | Tandon |
| 2006/0200143 A1 | 9/2006 | Warburton |
| 2006/0200144 A1 | 9/2006 | Warburton |
| 2006/0229617 A1 | 10/2006 | Meller et al. |
| 2006/0247638 A1 | 11/2006 | Trieu et al. |
| 2006/0264951 A1 | 11/2006 | Nelson et al. |
| 2007/0123878 A1 | 5/2007 | Shaver et al. |
| 2007/0142916 A1 | 6/2007 | Olson et al. |
| 2007/0260257 A1 | 11/2007 | Phan |
| 2008/0077154 A1 | 3/2008 | Edwards et al. |
| 2008/0132896 A1 | 6/2008 | Bowen et al. |
| 2008/0140078 A1 | 6/2008 | Nelson et al. |
| 2008/0149115 A1 | 6/2008 | Hauck et al. |
| 2008/0161805 A1* | 7/2008 | Saravia et al. .................. 606/60 |
| 2008/0221620 A1 | 9/2008 | Krause et al. |
| 2008/0234678 A1 | 9/2008 | Gutierrez et al. |
| 2008/0243132 A1 | 10/2008 | Tipirneni et al. |
| 2008/0255560 A1 | 10/2008 | Myers et al. |
| 2008/0262495 A1 | 10/2008 | Coati et al. |
| 2008/0269751 A1 | 10/2008 | Matityahu |
| 2008/0287951 A1 | 11/2008 | Stoneburner et al. |
| 2009/0018542 A1* | 1/2009 | Saravia et al. .................. 606/63 |
| 2009/0182336 A1 | 7/2009 | Brenzel et al. |
| 2009/0187116 A1 | 7/2009 | Noishiki et al. |
| 2009/0216232 A1* | 8/2009 | Buford et al. .................... 606/62 |
| 2009/0228007 A1 | 9/2009 | Justin et al. |
| 2009/0228008 A1 | 9/2009 | Justin et al. |
| 2010/0023010 A1 | 1/2010 | Nelson et al. |
| 2010/0094347 A1 | 4/2010 | Nelson et al. |
| 2011/0087227 A1 | 4/2011 | Mazur et al. |
| 2011/0144645 A1* | 6/2011 | Saravia et al. .................. 606/63 |
| 2011/0178520 A1 | 7/2011 | Taylor et al. |
| 2011/0190832 A1 | 8/2011 | Taylor et al. |
| 2011/0218585 A1 | 9/2011 | Krinke et al. |
| 2011/0218626 A1 | 9/2011 | Krinke et al. |
| 2011/0282346 A1 | 11/2011 | Pham et al. |

FOREIGN PATENT DOCUMENTS

| | | |
|---|---|---|
| EP | 1815813 A2 | 8/2007 |
| WO | WO 97/18769 | 5/1997 |
| WO | WO 98/27876 | 7/1998 |
| WO | WO 98/56301 | 12/1998 |
| WO | WO 99/20195 | 4/1999 |
| WO | WO 00/28906 | 5/2000 |
| WO | WO 01/28443 | 4/2001 |
| WO | WO 02/00270 | 1/2002 |
| WO | WO 02/00275 | 1/2002 |
| WO | WO 02/02158 | 1/2002 |
| WO | WO 2005/112804 | 12/2005 |
| WO | WO 2006/053210 | 5/2006 |
| WO | WO 2007/009123 | 1/2007 |

\* cited by examiner

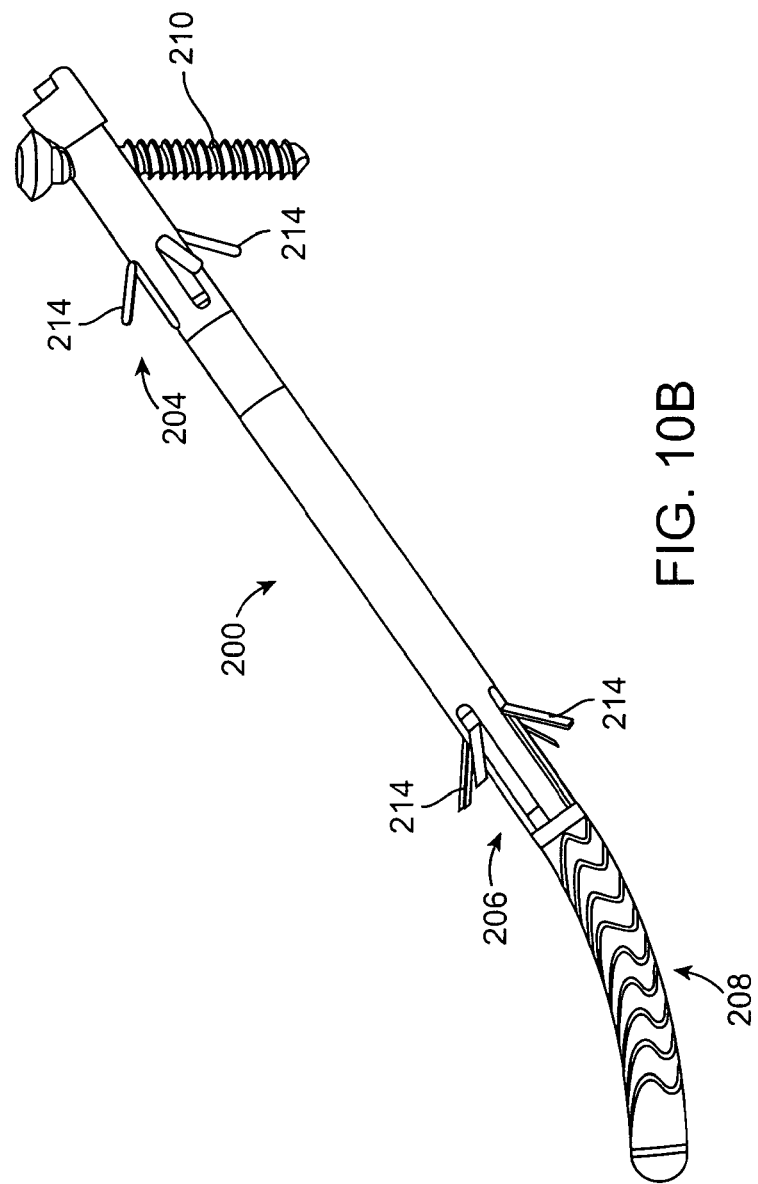

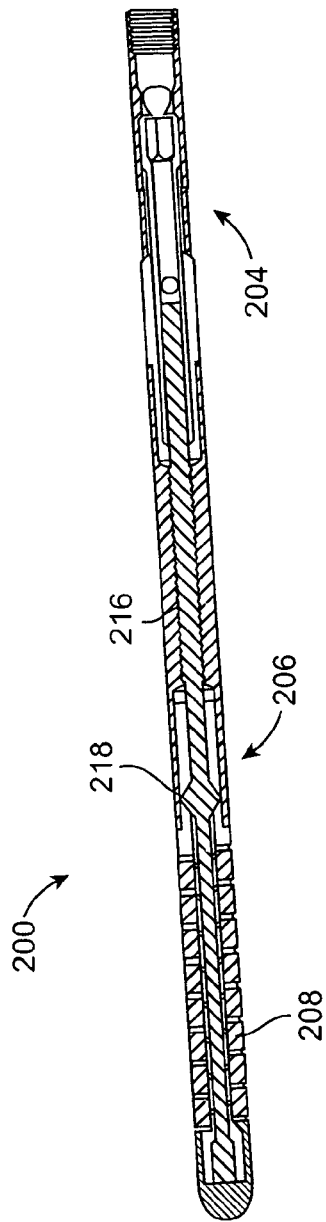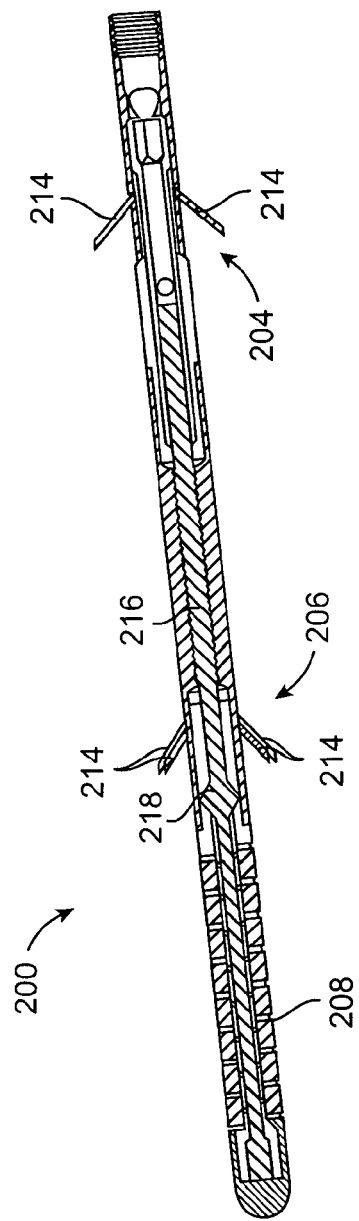

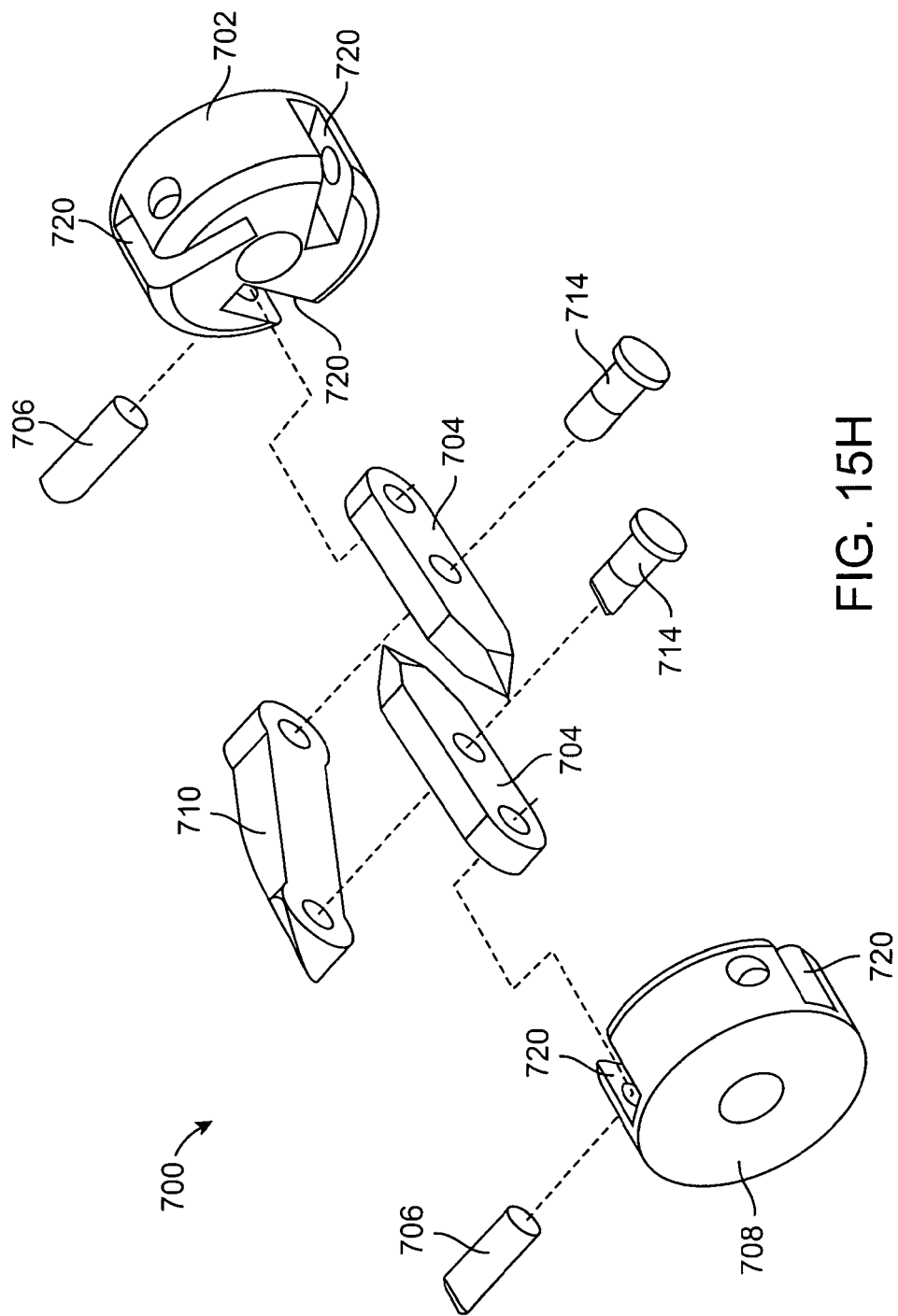

BONE FIXATION DEVICE, TOOLS AND METHODS

CROSS-REFERENCE TO RELATED APPLICATIONS

This application is a Continuation-in-Part of U.S. application Ser. No. 11/383,269, titled "MINIMALLY INVASIVE ACTUABLE BONE FIXATION DEVICES", filed May 15, 2006 which claims priority to U.S. Provisional Application No. 60/682,652, titled "METHOD AND SYSTEM FOR PROVIDING REINFORCEMENT OF BONES", filed May 18, 2005. This application is also a Continuation-in-part of U.S. application Ser. No. 11/383,800 filed May 17, 2006, titled "DEPLOYABLE INTRAMEDULLARY STENT SYSTEM FOR REINFORCEMENT OF BONE" which claims priority to U.S. Provisional Application No. 60/682,652, titled "METHOD AND SYSTEM FOR PROVIDING REINFORCEMENT OF BONES", filed May 18, 2005. This application is also a Continuation-in-Part of U.S. application Ser. No. 11/944,366, titled "FRACTURE FIXATION DEVICE, TOOLS AND METHODS", filed Nov. 21, 2007 which claims priority to U.S. provisional applications: No. 60/867,011, titled "BONE REPAIR IMPLANT WITH CENTRAL RATCHETING GUIDEWIRE", filed Nov. 22, 2006; No. 60/866,976, titled "SURGICAL TOOLS FOR USE IN DEPLOYING BONE REPAIR DEVICES," filed Nov. 22, 2006; and No. 60/949,071, titled "FRACTURE FIXATION DEVICE, TOOLS AND METHODS", filed Jul. 11, 2007. This application is also a Continuation-in-part of U.S. application Ser. No. 12/482,388 titled "FRACTURE FIXATION DEVICE, TOOLS AND METHODS" filed Jun. 10, 2009; application Ser. No. 12/482,395 titled "FRACTURE FIXATION DEVICE, TOOLS AND METHODS" filed Jun. 10, 2009 and application Ser. No. 12/482,406 titled "FRACTURE FIXATION DEVICE, TOOLS AND METHODS" filed Jun. 10, 2009.

This application claims priority of U.S. Provisional Application No. 61/100,635, titled "FRACTURE FIXATION DEVICE, TOOLS AND METHODS" filed Sep. 26, 2008; U.S. Provisional Application No. 61/100,652, titled "FRACTURE FIXATION DEVICE, TOOLS AND METHODS" filed Sep. 26, 2008; U.S. Provisional Application No. 61/122,563, titled "BONE FIXATION DEVICE, TOOLS AND METHODS" filed Dec. 15, 2008; U.S. Provisional Application No. 61/138,920, titled "BONE FIXATION DEVICE, TOOLS AND METHODS" filed Dec. 18, 2008; and U.S. Provisional Application No. 61/117,901, titled "BONE FRACTURE FIXATION SCREWS, SYSTEMS AND METHODS OF USE" filed Nov. 25, 2008.

INCORPORATION BY REFERENCE

All publications and patent applications mentioned in this specification are herein incorporated by reference to the same extent as if each individual publication or patent application was specifically and individually indicated to be incorporated by reference

BACKGROUND OF THE INVENTION

The present invention relates to devices, tools and methods for providing reinforcement of bones. More specifically, the present invention relates to devices, tools and methods for providing reconstruction and reinforcement of bones, including diseased, osteoporotic and fractured bones.

Bone fractures are a common medical condition both in the young and old segments of the population. However, with an increasingly aging population, osteoporosis has become more of a significant medical concern in part due to the risk of osteoporotic fractures. Osteoporosis and osteoarthritis are among the most common conditions to affect the musculoskeletal system, as well as frequent causes of locomotor pain and disability. Osteoporosis can occur in both human and animal subjects (e.g. horses). Osteoporosis (OP) and osteoarthritis (OA) occur in a substantial portion of the human population over the age of fifty. The National Osteoporosis Foundation estimates that as many as 44 million Americans are affected by osteoporosis and low bone mass, leading to fractures in more than 300,000 people over the age of 65. In 1997 the estimated cost for osteoporosis related fractures was $13 billion. That figure increased to $17 billion in 2002 and is projected to increase to $210-240 billion by 2040. Currently it is expected that one in two women, and one in four men, over the age of 50 will suffer an osteoporosis-related fracture. Osteoporosis is the most important underlying cause of fracture in the elderly. Also, sports and work-related accidents account for a significant number of bone fractures seen in emergency rooms among all age groups.

One current treatment of bone fractures includes surgically resetting the fractured bone. After the surgical procedure, the fractured area of the body (i.e., where the fractured bone is located) is often placed in an external cast for an extended period of time to ensure that the fractured bone heals properly. This can take several months for the bone to heal and for the patient to remove the cast before resuming normal activities.

In some instances, an intramedullary (IM) rod or nail is used to align and stabilize the fracture. In that instance, a metal rod is placed inside a canal of a bone and fixed in place, typically at both ends. See, for example, Fixion™ IM(Nail), www.disc-o-tech.com. This approach requires incision, access to the canal, and placement of the IM nail. The nail can be subsequently removed or left in place. A conventional IM nail procedure requires a similar, but possibly larger, opening to the space, a long metallic nail being placed across the fracture, and either subsequent removal, and or when the nail is not removed, a long term implant of the IM nail. The outer diameter of the IM nail must be selected for the minimum inside diameter of the space. Therefore, portions of the IM nail may not be in contact with the canal. Further, micromotion between the bone and the IM nail may cause pain or necrosis of the bone. In still other cases, infection can occur. The IM nail may be removed after the fracture has healed. This requires a subsequent surgery with all of the complications and risks of a later intrusive procedure. In general, rigid IM rods or nails are difficult to insert, can damage the bone and require additional incisions for cross-screws to attach the rods or nails to the bone.

Some IM nails are inflatable. See, for example, Meta-Fix IM Nailing System, www.disc-o-tech.com. Such IM nails require inflating the rod with very high pressures, endangering the surrounding bone. Inflatable nails have many of the same drawbacks as the rigid IM nails described above.

External fixation is another technique employed to repair fractures. In this approach, a rod may traverse the fracture site outside of the epidermis. The rod is attached to the bone with trans-dermal screws. If external fixation is used, the patient will have multiple incisions, screws, and trans-dermal infection paths. Furthermore, the external fixation is cosmetically intrusive, bulky, and prone to painful inadvertent manipulation by environmental conditions such as, for example, bumping into objects and laying on the device. Other concepts relating to bone repair are disclosed in, for example, U.S. Pat.

Nos. 5,108,404 to Scholten for Surgical Protocol for Fixation of Bone Using Inflatable Device; 4,453,539 to Raftopoulos et al. for Expandable Intramedullary Nail for the Fixation of Bone Fractures; 4,854,312 to Raftopolous for Expanding Nail; 4,932,969 to Frey et al. for Joint Endoprosthesis; 5,571,189 to Kuslich for Expandable Fabric Implant for Stabilizing the Spinal Motion Segment; 4,522,200 to Stednitz for Adjustable Rod; 4,204,531 to Aginsky for Nail with Expanding Mechanism; 5,480,400 to Berger for Method and Device for Internal Fixation of Bone Fractures; 5,102,413 to Poddar for Inflatable Bone Fixation Device; 5,303,718 to Krajicek for Method and Device for the Osteosynthesis of Bones; 6,358,283 to Hogfors et al. for Implantable Device for Lengthening and Correcting Malpositions of Skeletal Bones; 6,127,597 to Beyar et al. for Systems for Percutaneous Bone and Spinal Stabilization, Fixation and Repair; 6,527,775 to Warburton for Interlocking Fixation Device for the Distal Radius; U.S. Patent Publication US2006/0084998 A1 to Levy et al. for Expandable Orthopedic Device; and PCT Publication WO 2005/112804 A1 to Myers Surgical Solutions, LLC for Fracture Fixation and Site Stabilization System. Other fracture fixation devices, and tools for deploying fracture fixation devices, have been described in: US Patent Appl. Publ. No. 2006/0254950; U.S. Ser. No. 60/867,011 (filed Nov. 22, 2006); U.S. Ser. No. 60/866,976 (filed Nov. 22, 2006); and U.S. Ser. No. 60/866,920 (filed Nov. 22, 2006).

In view of the foregoing, it would be desirable to have a device, system and method for providing effective and minimally invasive bone reinforcement and fracture fixation to treat fractured or diseased bones, while improving the ease of insertion, eliminating cross-screw incisions and minimizing trauma.

SUMMARY OF THE INVENTION

Aspects of the invention relate to embodiments of a bone fixation device and to methods for using such a device for repairing a bone fracture. The bone fixation device may include an elongate body with a longitudinal axis and having a flexible state and a rigid state. The device further may include a plurality of grippers disposed at longitudinally-spaced locations along the elongated body, a rigid hub connected to the elongated body, and an actuator that is operably-connected to the grippers to deploy the grippers from a first shape to an expanded second shape.

In one embodiment, a bone fixation device is provided with an elongate body having a longitudinal axis and having a first state in which at least a portion of the body is flexible and a second state in which the body is generally rigid, an actuate-able gripper disposed at a distal location on the elongated body, a hub located on a proximal end of the elongated body, and an actuator operably connected to the gripper to deploy the gripper from a retracted configuration to an expanded configuration.

Methods of repairing a fracture of a bone are also disclosed. One such method comprises inserting a bone fixation device into an intramedullary space of the bone to place at least a portion of an elongate body of the fixation device in a flexible state on one side of the fracture and at least a portion of a hub on another side of the fracture, and operating an actuator to deploy at least one gripper of the fixation device to engage an inner surface of the intramedullary space to anchor the fixation device to the bone.

One embodiment of the present invention provides a low weight to volume mechanical support for fixation, reinforcement and reconstruction of bone or other regions of the musculo-skeletal system in both humans and animals. The method of delivery of the device is another aspect of the invention. The method of delivery of the device in accordance with the various embodiments of the invention reduces the trauma created during surgery, decreasing the risks associated with infection and thereby decreasing the recuperation time of the patient. The framework may in one embodiment include an expandable and contractible structure to permit re-placement and removal of the reinforcement structure or framework.

In accordance with the various embodiments of the present invention, the mechanical supporting framework or device may be made from a variety of materials such as metal, composite, plastic or amorphous materials, which include, but are not limited to, steel, stainless steel, cobalt chromium plated steel, titanium, nickel titanium alloy (nitinol), super-elastic alloy, and polymethylmethacrylate (PMMA). The device may also include other polymeric materials that are biocompatible and provide mechanical strength, that include polymeric material with ability to carry and delivery therapeutic agents, that include bioabsorbable properties, as well as composite materials and composite materials of titanium and polyetheretherketone (PEEK™), composite materials of polymers and minerals, composite materials of polymers and glass fibers, composite materials of metal, polymer, and minerals.

Within the scope of the present invention, each of the aforementioned types of device may further be coated with proteins from synthetic or animal source, or include collagen coated structures, and radioactive or brachytherapy materials. Furthermore, the construction of the supporting framework or device may include radio-opaque markers or components that assist in their location during and after placement in the bone or other region of the musculo-skeletal systems.

Further, the reinforcement device may, in one embodiment, be osteo incorporating, such that the reinforcement device may be integrated into the bone.

In still another embodiment of the invention, a method of repairing a bone fracture is disclosed that comprises: accessing a fracture along a length of a bone through a bony protuberance at an access point at an end of a bone; advancing a bone fixation device into a space through the access point at the end of the bone; bending a portion of the bone fixation device along its length to traverse the fracture; and locking the bone fixation device into place within the space of the bone. The method can also include the step of advancing an obturator through the bony protuberance and across the fracture prior to advancing the bone fixation device into the space. In yet another embodiment of the method, the step of anchoring the bone fixation device within the space can be included.

An aspect of the invention discloses a removable bone fixation device that uses a single port of insertion and has a single-end of remote actuation wherein a bone fixation device stabilizes bone after it has traversed the fracture. The bone fixation device is adapted to provide a single end in one area or location where the device initiates interaction with bone. The device can be deployed such that the device interacts with bone. Single portal insertion and single-end remote actuation enables the surgeon to insert and deploy the device, deactivate and remove the device, reduce bone fractures, displace or compress the bone, and lock the device in place. In addition, the single-end actuation enables the device to grip bone, compresses the rigidizable flexible body, permits axial, torsional and angular adjustments to its position during surgery, and releases the device from the bone during its removal procedure. A removable extractor can be provided in some embodiments of the device to enable the device to be placed and extracted by deployment and remote actuation from a single end. The device of the invention can be adapted and configured to provide at least one rigidizable flexible body or sleeve. Further the body can be configured to be flexible in all angles and directions. The flexibility provided is in selective planes and angles in the Cartesian, polar, or cylindrical coordinate systems. Further, in some embodiments, the body is configured to have a remote actuation at a single end. Additionally, the body can be configured to have apertures, windings, etc. The device may be configured to function with non-flexible bodies for use in bones that have a substantially straight segment or curved segments with a constant radius of curvature. Another aspect of the invention includes a bone fixation device in that has mechanical geometry that interacts with bone by a change in the size of at least one dimension of a Cartesian, polar, or spherical coordinate system. Further, in some embodiments, bioabsorbable materials can be used in conjunction with the devices, for example by providing specific subcomponents of the device configured from bioabsorbable materials. A sleeve can be provided in some embodiments where the sleeve is removable, has deployment, remote actuation, and a single end. Where a sleeve is employed, the sleeve can be adapted to provide a deployable interdigitation process or to provide an aperture along its length through which the deployable interdigitation process is adapted to engage bone. In some embodiments, the deployable interdigitation process is further adapted to engage bone when actuated by the sleeve. In some embodiments, the bone fixation device further comprises a cantilever adapted to retain the deployable bone fixation device within the space. The sleeve can further be adapted to be expanded and collapsed within the space by a user. One end of the device can be configured to provide a blunt obturator surface adapted to advance into the bone. A guiding tip may also be provided that facilitates guiding the device through the bone. Further, the deployable bone fixation device can be adapted to receive external stimulation to provide therapy to the bone. The device can further be adapted to provide an integral stimulator which provides therapy to the bone. In still other embodiments, the device can be adapted to receive deliver therapeutic stimulation to the bone.

The devices disclosed herein may be employed in various regions of the body, including: cranial, thoracic, lower extremities and upper extremities. Additionally, the devices are suitable for a variety of breaks including, metaphyseal and diaphyseal.

The fracture fixation devices of various embodiments of the invention are adapted to be inserted through an opening of a fractured bone, such as the radius (e.g., through a bony protuberance on a distal or proximal end or through the midshaft) into the intramedullary canal of the bone. In some embodiments, the fixation device has two main components, one configured component for being disposed on the side of the fracture closest to the opening and one component configured for being disposed on the other side of the fracture from the opening so that the fixation device traverses the fracture.

The device components cooperate to align, fix and/or reduce the fracture so as to promote healing. The device may be removed from the bone after insertion (e.g., after the fracture has healed or for other reasons), or it may be left in the bone for an extended period of time or permanently.

In some embodiments, the fracture fixation device has one or more actuatable anchors or grippers on its proximal and/or distal ends. These anchors may be used to hold the fixation device to the bone while the bone heals.

In some embodiments, to aid in insertion into the intramedullary canal, at least one component of the fracture fixation device has a substantially flexible state and a substantially rigid state. Once in place, deployment of the device also causes the components to change from the flexible state to a rigid state to aid in proper fixation of the fracture. At least one of the components may be substantially rigid or semi-flexible. At least one component may provide a bone screw attachment site for the fixation device.

Embodiments of the invention also provide deployment tools with a tool guide for precise alignment of one or more bone screws with the fracture fixation device. These embodiments also provide bone screw orientation flexibility so that the clinician can select an orientation for the bone screw(s) that will engage the fixation device as well as any desired bone fragments or other bone or tissue locations.

These and other features and advantages of the present invention will be understood upon consideration of the following detailed description of the invention and the accompanying drawings.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 10B is perspective view of the device shown in FIG. 10A shown in a deployed state.

FIG. 10E is a cross-sectional view of the device shown in FIG. 10A shown in a retracted or undeployed state.

FIG. 10F is a cross-sectional view of the device shown in FIG. 10A shown in a deployed state.

FIG. 15H is an exploded perspective view showing the gripper of FIG. 15A with two of the three sets of gripper arms removed for clarity.

DETAILED DESCRIPTION OF THE INVENTION

By way of background and to provide context for the invention, it may be useful to understand that bone is often described as a specialized connective tissue that serves three major functions anatomically. First, bone provides a mechanical function by providing structure and muscular attachment for movement. Second, bone provides a metabolic function by providing a reserve for calcium and phosphate. Finally, bone provides a protective function by enclosing bone marrow and vital organs. Bones can be categorized as long bones (e.g. radius, femur, tibia and humerus) and flat bones (e.g. skull, scapula and mandible). Each bone type has a different embryological template. Further each bone type contains cortical and trabecular bone in varying proportions. The devices of this invention can be adapted for use in any of the bones of the body as will be appreciated by those skilled in the art.

Cortical bone (compact) forms the shaft, or diaphysis, of long bones and the outer shell of flat bones. The cortical bone provides the main mechanical and protective function. The trabecular bone (cancellous) is found at the end of the long bones, or the epiphysis, and inside the cortex of flat bones. The trabecular bone consists of a network of interconnecting trabecular plates and rods and is the major site of bone remodeling and resorption for mineral homeostasis. During development, the zone of growth between the epiphysis and diaphysis is the metaphysis. Finally, woven bone, which lacks the organized structure of cortical or cancellous bone, is the first bone laid down during fracture repair. Once a bone is fractured, the bone segments are positioned in proximity to each other in a manner that enables woven bone to be laid down on the surface of the fracture. This description of anatomy and physiology is provided in order to facilitate an understanding of the invention. Persons of skill in the art will also appreciate that the scope and nature of the invention is not limited by the anatomy discussion provided. Further, it will be appreciated there can be variations in anatomical characteristics of an individual patient, as a result of a variety of factors, which are not described herein. Further, it will be appreciated there can be variations in anatomical characteristics between bones which are not described herein.

Figure 1:
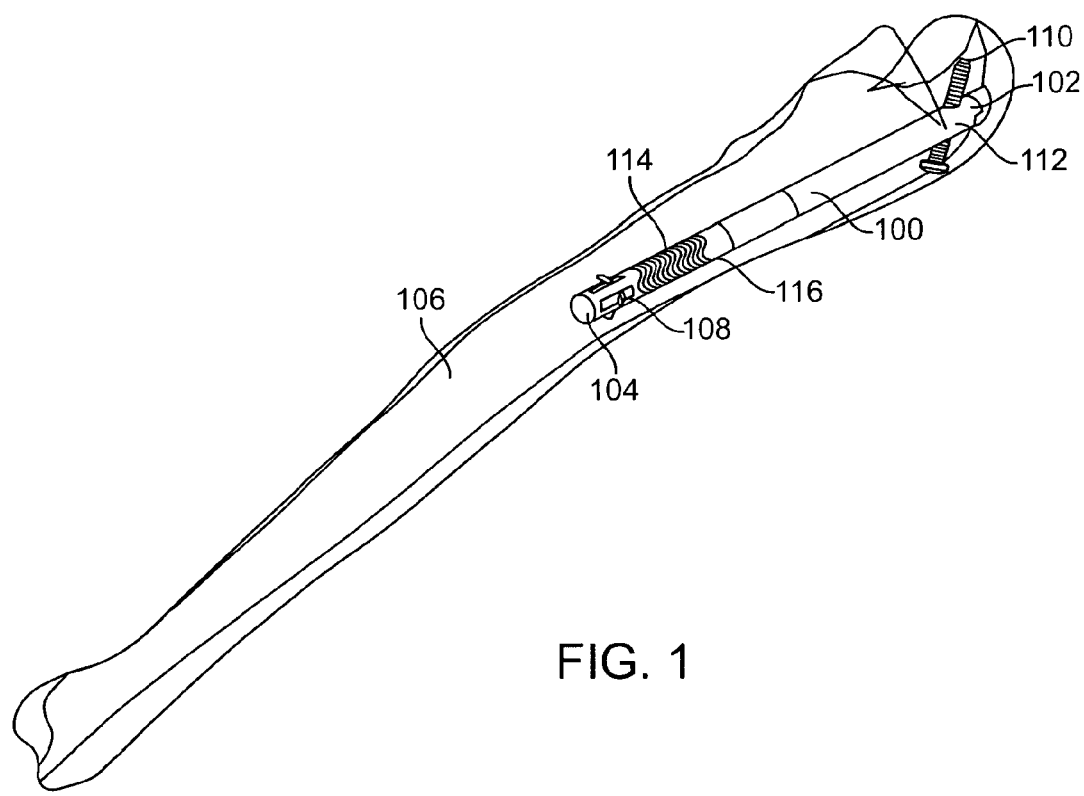
FIG. 1 is a perspective view of an embodiment of a bone fixation device implanted in a bone according to the invention.
Figure 2:
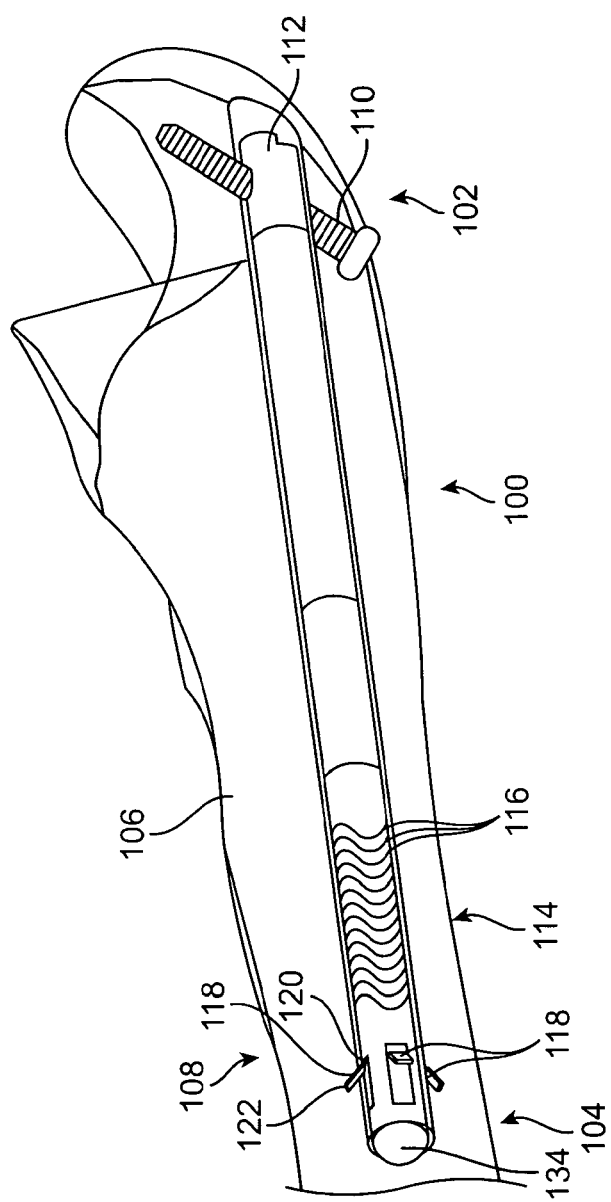
FIG. 2 is another perspective view of the implanted device of FIG. 1.

FIGS. 1 and 2 are perspective views of an embodiment of a bone fixation device 100 having a proximal end 102 (nearest the surgeon) and a distal end 104 (further from surgeon) and positioned within the bone space of a patient according to the invention. In this example, device 100 is shown implanted in the upper (or proximal) end of an ulna 106. The proximal end and distal end, as used in this context, refers to the position of an end of the device relative to the remainder of the device or the opposing end as it appears in the drawing. The proximal end can be used to refer to the end manipulated by the user or physician. The distal end can be used to refer to the end of the device that is inserted and advanced within the bone and is furthest away from the physician. As will be appreciated by those skilled in the art, the use of proximal and distal could change in another context, e.g. the anatomical context in which proximal and distal use the patient as reference, or where the entry point is distal from the surgeon.

When implanted within a patient, the device can be held in place with suitable fasteners such as wire, screws, nails, bolts, nuts and/or washers. The device 100 is used for fixation of fractures of the proximal or distal end of long bones such as intracapsular, intertrochanteric, intercervical, supracondular, or condular fractures of the femur; for fusion of a joint; or for surgical procedures that involve cutting a bone. The devices 100 may be implanted or attached through the skin so that a pulling force (traction may be applied to the skeletal system).

Figure 3:
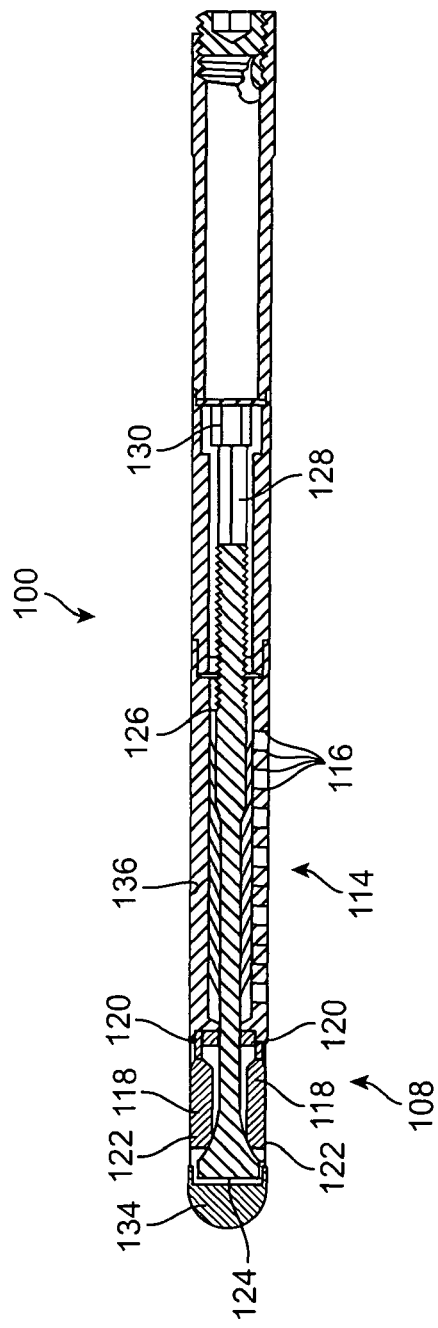
FIG. 3 is a longitudinal cross-section view of the bone fixation device of FIG. 1 in a non-deployed state.

In the embodiment shown in FIG. 1, the design of the metaphyseal to diaphyseal fixation device 100 depicted is adapted to provide a bone engaging mechanism or gripper 108 adapted to engage target bone of a patient from the inside of the bone. As configured for this anatomical application, the device is designed to facilitate bone healing when placed in the intramedullary space within a post fractured bone. This device 100 has a gripper 108 positioned distally and shown deployed radially outward against the wall of the intramedullary cavity. On entry into the cavity, gripper 108 is flat and retracted (FIG. 3). Upon deployment, gripper 108 pivots radially outward and grips the diaphyseal bone from the inside of the bone. One or more screws 110 placed through apertures through the hub 112 lock the device 100 to the metaphyseal bone. Hence, the metaphysis and the diaphysis are joined. A flexible-to-rigid body portion 114 may also be provided, and in this embodiment is positioned between gripper 108 and hub 112. It may be provided with wavy spiral cuts 116 for that purpose, as will be described in more detail below.

FIG. 3 shows a longitudinal cross-section of device 100 in a non-deployed configuration. In this embodiment, gripper 108 includes two pairs of opposing bendable gripping members 118. Two of the bendable gripping members 118 are shown in FIG. 3, while the other two (not shown in FIG. 3) are located at the same axial location but offset by 90 degrees. Each bendable gripping member 118 has a thinned portion 120 that permits bending as the opposite distal end 122 of member 118 is urged radially outward, such that member 118 pivots about thinned portion 120. When extended, distal ends 122 of bendable members 118 contact the inside of the bone to anchor the distal portion of device 100 to the bone. In alternative embodiments (not shown), the gripper may comprise 1, 2, 3, 4, 5, 6 or more bendable members similar to members 118 shown.

During actuation, bendable members 118 of gripper 108 are urged radially outward by a ramped surface on actuator head 124. Actuator head 124 is formed on the distal end of actuator 126. The proximal end of actuator 126 is threaded to engage a threaded bore of drive member 128. The proximal end of drive member 128 is provided with a keyed socket 130 for receiving the tip of a rotary driver tool 132 (shown in FIGS. 4 and 5) through the proximal bore of device 100. As rotary driver tool 132 turns drive member 128, actuator 126 is drawn in a proximal direction to outwardly actuate gripper members 118.

A hemispherical tip cover 134 may be provided at the distal end of the device as shown to act as a blunt obturator. This arrangement facilitates penetration of bone (e.g. an intramedullary space) by device 100 while keeping the tip of device 100 from digging into bone during insertion.

As previously mentioned, device 100 may include one or more flexible-to-rigid body portions 114. This feature is flexible upon entry into bone and rigid upon application of compressive axial force provided by tensioning actuator 126. Various embodiments of a flexible-to-rigid portion may be used, including dual helical springs whose inner and outer tubular components coil in opposite directions, a chain of ball bearings with flats or roughened surfaces, a chain of cylinders with flats, features, cones, spherical or pointed interdigitating surfaces, wavy-helical cut tubes, two helical cut tubes in opposite directions, linear wires with interdigitating coils, and bellows-like structures.

The design of the flexible-to-rigid tubular body portion 114 allows a single-piece design to maximize the transformation of the same body from a very flexible member that minimizes strength in bending to a rigid body that maximizes strength in bending and torsion. The flexible member transforms to a rigid member when compressive forces are applied in the axial direction at each end, such as by an actuator similar to 126. The body portion 114 is made, for example, by a near-helical cut 116 on a tubular member at an angle of incidence to the axis somewhere between 0 and 180 degrees from the longitudinal axis of the tubular body portion 114. The near-helical cut or wavy-helical cut may be formed by the superposition of a helical curve added to a cyclic curve that produces waves of frequencies equal or greater than zero per turn around the circumference and with cyclic amplitude greater than zero. The waves of one segment nest with those on either side of it, thus increasing the torque, bending strength and stiffness of the tubular body when subjected to compressive forces. The tapered surfaces formed by the incident angle allow each turn to overlap or interdigitate with the segment on either side of it, thus increasing the bending strength when the body is in compression. Additionally, the cuts can be altered in depth and distance between the cuts on the longitudinal axis along the length of body portion 114 to variably alter the flexible-to-rigid characteristics of the tubular body along its length.

The cuts 116 in body portion 114 allow an otherwise rigid member to increase its flexibility to a large degree during deployment. The tubular member can have constant or varying internal and external diameters. This design reduces the number of parts of the flexible-to-rigid body portion of the device and allows insertion and extraction of the device through a curved entry port in the bone while maximizing its rigidity once inserted. Application and removal of compressive forces provided by a parallel member such as wire(s), tension ribbons, a sheath, wound flexible cable, or actuator 126 as shown will transform the body from flexible to rigid and vice versa.

In operation, as actuator 126 is tightened, gripper members 118 are extended radially outwardly. Once the distal ends of gripper members 118 contact bone and stop moving outward, continued rotation of actuator 126 draws the proximal end 102 and the distal end 104 of device 100 closer together until cuts 116 are substantially closed. As this happens, body portion 114 changes from being flexible to rigid to better secure the bone fracture(s), as will be further described below. Rotating drive member 128 in the opposite direction causes body portion 114 to change from a rigid to a flexible state, such as for removing device 100 if needed in the initial procedure or during a subsequent procedure after the bone fracture(s) have partially or completely healed. Body portion 114 may be provided with a solid longitudinal portion 136 (as best seen in FIGS. 3 and 9B) such that cuts 116 are a series of individual cuts each traversing less than 360 degrees in circumference, rather than a single, continuous helical cut. This solid portion 136 can aid in removal of device 100 by keeping body portion 114 from extending axially like a spring.

Figure 4:
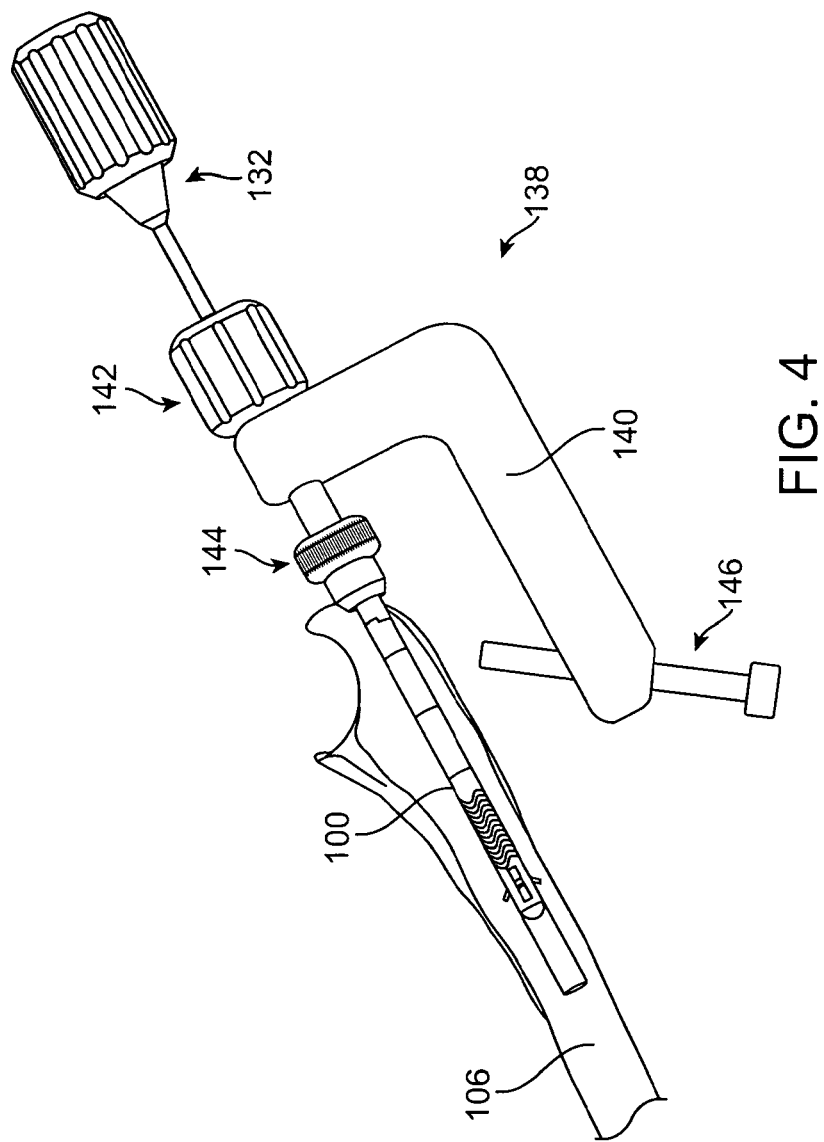
FIG. 4 is a plan view of a combination deployment tool that may be used with the bone fixation device of FIG. 1.

FIG. 4 illustrates a combination tool 138 useful for inserting device 100, actuating gripper 108, compressing flexible-to-rigid body portion 114, approximating the fracture in bone 106, aligning anchor screw(s) 110, and removing device 100, if desired. In this exemplary embodiment, tool 138 includes an L-shaped body 140 that mounts the other components of the tool and also serves as a handle. The main components of tool 138 are a device attachment portion 142, a rotary driver 132, an approximating driver 144, and a screw alignment portion 146.

Figure 5:
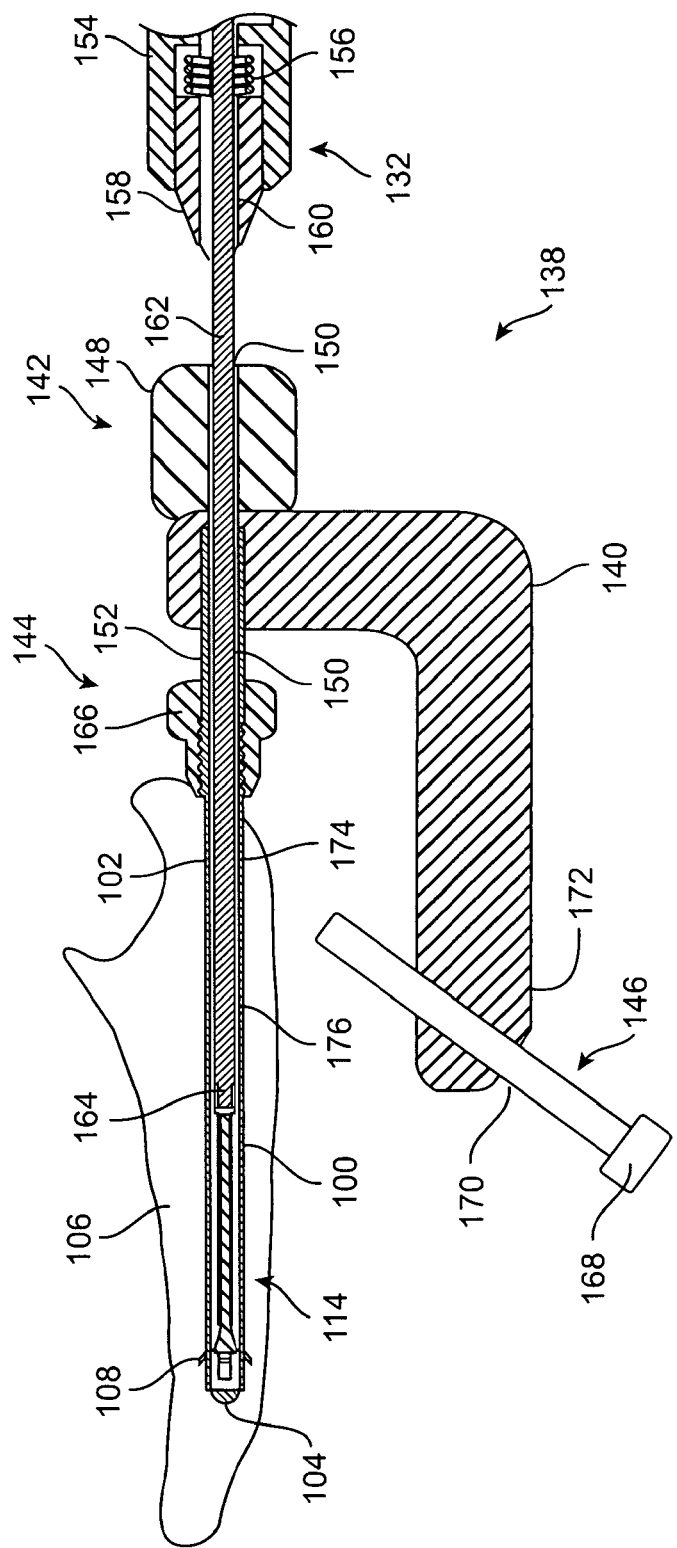
FIG. 5 is a cross-section view of the tool and device shown in FIG. 4.

FIG. 5 shows a cross-section of the tool 138 and device 100 illustrated in FIG. 4. As shown, device attachment portion 142 includes a knob 148 rigidly coupled to a tube 150 which is rotatably mounted within sleeve 152. Sleeve 152 in turn is fixedly mounted to tool body 140. The distal end of tube 150 is provided with external threads for engaging the internal threads on the proximal end of device 100. As best seen in FIG. 4, both the distal end of sleeve 152 and the proximal end of device 100 may be provided with semicircular steps that inter-engage to prevent device 100 from rotating with respect to sleeve 152. With this arrangement, device 100 can be prevented from rotating when it is secured to tool 138 by tube 150 of device attachment portion 142. The mating semicircular steps also serve to position device 100 in a particular axial and angular orientation with respect to tool 138 for aligning screws with screw holes, as will be later described.

Rotary driver 132 may be used to actuate gripper 108 and compress flexible-to-rigid body portion 114 after device 100 is inserted into bone 106. Driver 132 may also be used to allow body portion 114 to decompress and gripper 108 to retract if removal of device 100 from bone 106 is desired. In the embodiment shown, driver 132 includes knob 154, torsion spring 156, hub 158, bushing 160 and shaft 162. The distal end of shaft 162 is provided with a mating tip 164, such as one having a hex-key shape, for engaging with keyed socket 130 of device 100 (best seen in FIG. 3), such that turning driver shaft 162 turns drive member 128 and axially actuates actuator 126, as described above.

The proximal end of shaft 162 may be fitted with a bushing 160, such as with a press-fit. Hub 158 may be secured over bushing 160, such as with a pin through bushing 160 and shaft 162. In this embodiment, knob 154 is rotatably mounted over hub 158 and bushing 160 such that knob 154 can rotate independently from shaft 162. A torsion spring 156 may be used to couple knob 154 to hub 158 as shown to create a torque limiting and/or torque measuring driver. With this indirect coupling arrangement, as knob 154 is rotated about shaft 162, spring 156 urges hub 158 and shaft 162 to rotate in the same direction. Rotational resistance applied by device 100 to shaft tip 164 will increase in this embodiment as gripper 108 engages bone 106, and flexible-to-rigid body portion 114 compresses. As more torque is applied to knob 154, it will advance rotationally with respect to hub 158 as torsion spring 156 undergoes more stress. Markings may be provided on knob 154 and hub 158 to indicate the torque being applied. In this manner, a surgeon can use driver 132 to apply torque to device 100 in a predetermined range. This can help ensure that gripper 108 is adequately set in bone 106, body portion 114 is sufficiently compressed, and excessive torque is not being applied that might damage device 100, bone 106 or cause slippage there between. A slip clutch or other mechanism may be provided to allow the applied torque to be limited or indicated. For example, driver 132 may be configured to "click" into or out of a detent position when a desired torque is reached, thus allowing the surgeon to apply a desired torque without needing to observe any indicia on the driver. In alternative embodiments, the driver knob may be selectably or permanently coupled to shaft 162 directly.

After device 100 is inserted in bone 106 and deployed with tool 138 as described above, the approximating driver portion 144 of tool 138 may be used to compress one or more fractures in bone 106. Approximating driver 144 includes knob 166 located on sleeve 152. Knob 166 may be knurled on an outer circumference, and have threads on at least a portion of its axial bore. The internal threads of knob 166 engage with mating external threads on sleeve 152 such that when knob 166 is rotated it advances axially with respect to sleeve 152. When device 100 is anchored in bone 106, sleeve 152 is prevented from moving away from the bone. Accordingly, as knob 166 is advanced axially toward bone 106, it serves to approximate bone fractures located between gripper 108 and knob 166. Suitable thread pitch and knob circumference may be selected to allow a surgeon to supply a desired approximating force to bone 106 by using a reasonable rotation force on knob 166. In alternative embodiments (not shown), a torque indicating and/or torque limiting mechanism as described above may be incorporated into approximating driver 144.

As previously indicated, tool 138 may also include a screw alignment portion 146. In the embodiment depicted in the figures, alignment portion 146 includes a removable alignment tube 168 and two bores 170 and 172 through tool body 140. In alternative embodiments (not shown), a single bore or more than two bores may be used, with or without the use of separate alignment tube(s).

In operation, alignment tube 168 is first received in bore 170 as shown. In this position, tube 168 is in axial alignment with angled hole 174 at the distal end 102 of device 100. As described above, the mating semicircular steps of device 100 and sleeve 152 position angled hole 174 in its desired orientation. With this arrangement, a drill bit, screw driver, screw and/or other fastening device or tool may be inserted through the bore of tube 168 such that the device(s) are properly aligned with hole 174. The outward end of alignment tube 168 may also serve as a depth guide to stop a drill bit, screw and/or other fastener from penetrating bone 106 beyond a predetermined depth.

Alignment tube 168 may be withdrawn from bore 170 as shown, and inserted in bore 172. In this position, tube 168 aligns with hole 176 of device 100. As described above, a drill bit, screw driver, screw and/or other fastening device may be inserted through the bore of tube 168 such that the device(s) are properly aligned with hole 176.

Figure 6:
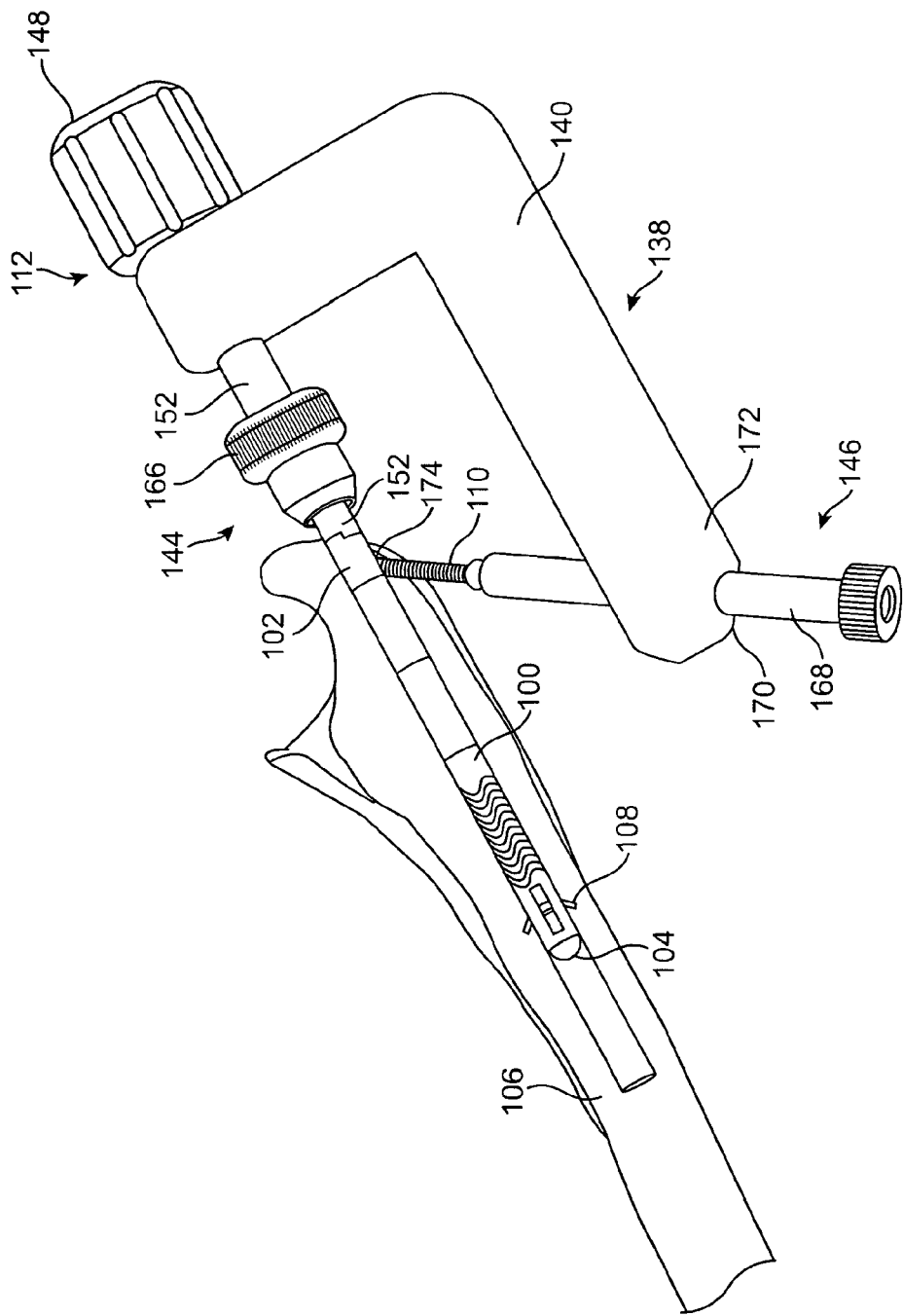
FIG. 6 is a perspective view of the tool and device shown in FIG. 4.

FIG. 6 shows alignment tube 168 of tool 138 aligning screw 110 with angled hole 174 at the distal end of device 100, as described above.

Figure 7:
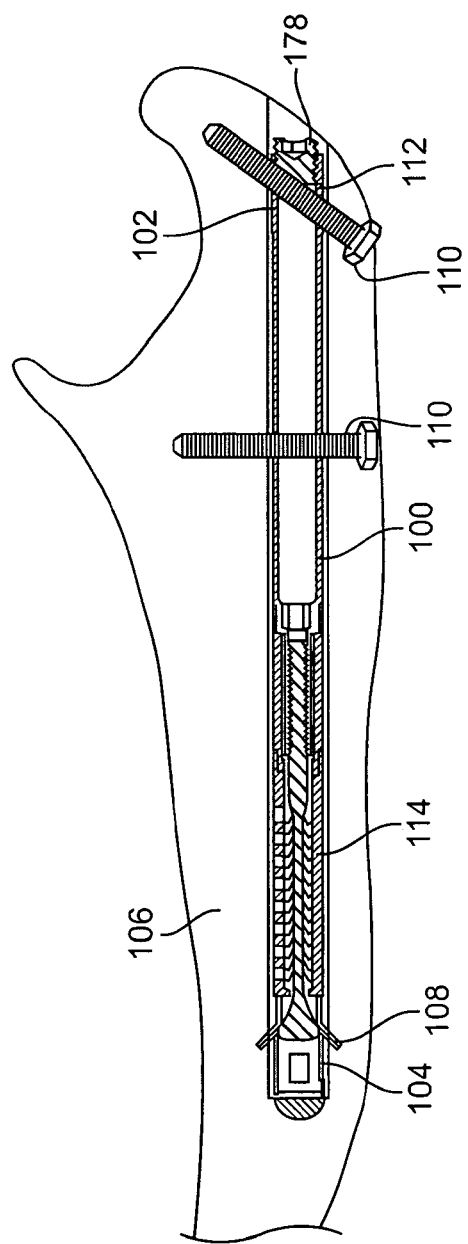
FIG. 7 is a cross-section view of the implanted device of FIG. 1.

FIG. 7 shows a first screw 110 received through angled hole 174 and a second screw 110 received through hole 176 in device 100 and into bone 106. Screws 110 may be installed manually or with the aid of tool 138 as described above. The heads of screws 110 may be configured to be self-countersinking such that they remain substantially beneath the outer surface of the bone when installed, as shown, so as to not interfere with adjacent tissue. In this embodiment, the proximal end 102 of device 100 is secured to bone 106 with two screws 110, and the distal end 104 is secured by gripper 108. In this manner, any bone fractures located between the proximal screw 110 and distal gripper 108 may be approximated and rigidly held together by device 100. In alternative embodiments (not shown), more than one gripper may be used, or only screws or other fasteners without grippers may be used to secure device 100 within bone 106. For example, the device shown in FIG. 1 could be configured with a second gripper located between screw 110 and the middle of the device if the fracture is located more at the mid-shaft of the bone. Similarly, more than two screws or other fasteners may be used, or only grippers without fasteners may be used. In various embodiments, holes such as 174 and 176 as shown and described above can be preformed in the implantable device. In other embodiments, some or all of the holes can be drilled or otherwise formed in situ after the device is implanted in the bone.

Once device 100 is secured within bone 106, combination tool 138 may be removed by turning knob 148 to disengage threads of tube 150 from threads within the proximal end 102 of device 100. An end plug 178 may be threaded into the proximal end 102 of device 100 to preventingrowth of tissue into implanted device 100. Device 100 may be left in bone 106 permanently, or it may be removed by performing the above described steps in reverse. In particular, plug 178 is removed, tool 138 is attached, screws 110 are removed, gripper 108 is retracted, and device 100 is pulled out using tool 138.

Figure 8:
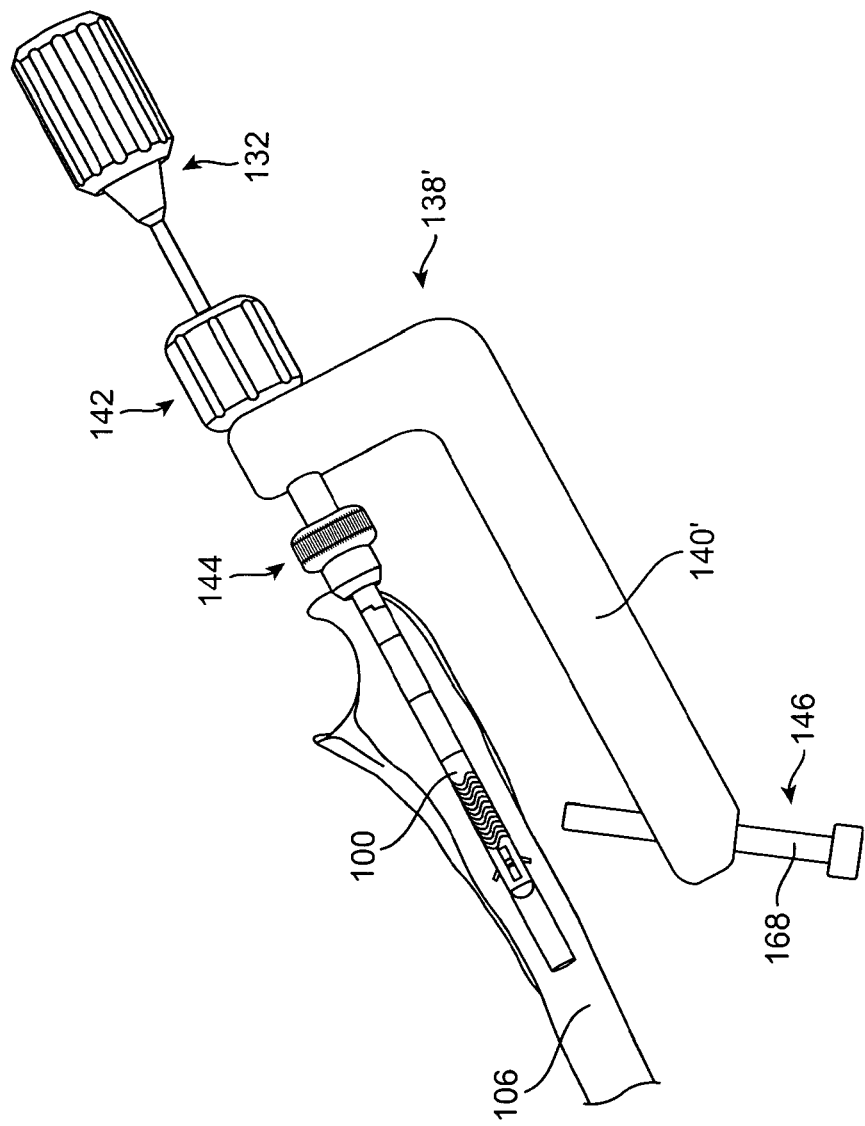
FIG. 8 is a plan view of an alternative combination deployment tool that may be used with the bone fixation device of FIG. 1.

FIG. 8 shows an alternative embodiment of a combination tool 138' useful for inserting device 100, actuating gripper 108, compressing flexible-to-rigid body portion 114, approximating the fracture in bone 106, aligning anchor screw(s) 110, and removing device 100, if desired. Like tool 138 described above, exemplary tool 138' includes an L-shaped body 140' that mounts the other components of the tool and also serves as a handle. The main components of tool 138' are a device attachment portion 142, a rotary driver 132, an approximating driver 144, and a screw alignment portion 146. These components are constructed and function in a similar fashion to the components of tool 138 described above. Tool 138' is constructed to allow one or more screw holes to be formed in vivo, and/or allow screw(s) to be aligned with such screw holes or preformed screw holes, through flexible-to-rigid body portion 114 of device 100. Tool 138' may be configured to allow the screw hole(s) may be formed at an angle through body portion 114, and/or formed perpendicularly to the longitudinal axis of device 100. Tool 138' may also include the capability to form screw holes or align screws for insertion in the proximal hub portion of device 100 as described above.

Tool 138' may be used to form screw hole(s) in flexible-to-rigid body portion 114 by guiding a drill bit with alignment tube 168. Screw hole(s) may also be formed directly in body portion 114 without pre-forming or drilling holes in vivo, but by placing a screw directly into body portion 114, such as with a self-tapping screw guided with alignment tube 168.

Internal components within device 100, such as actuator 126, may be configured such that screw(s) pass though it or pass around it. For example, in some embodiments the actuator comprises one or more cables, leaving enough room within body portion 114 so that a screw can avoid the actuator(s), or move it/them out of the way when passing into or through body portion 114. In some embodiments, the one or more actuators are large enough to allow one or more screws to pass through it/them without impeding the operation of the actuator(s). In some embodiments, the screw(s) only enter one wall of tubular body portion 114 without entering the interior space of the body portion.

Figure 9A:
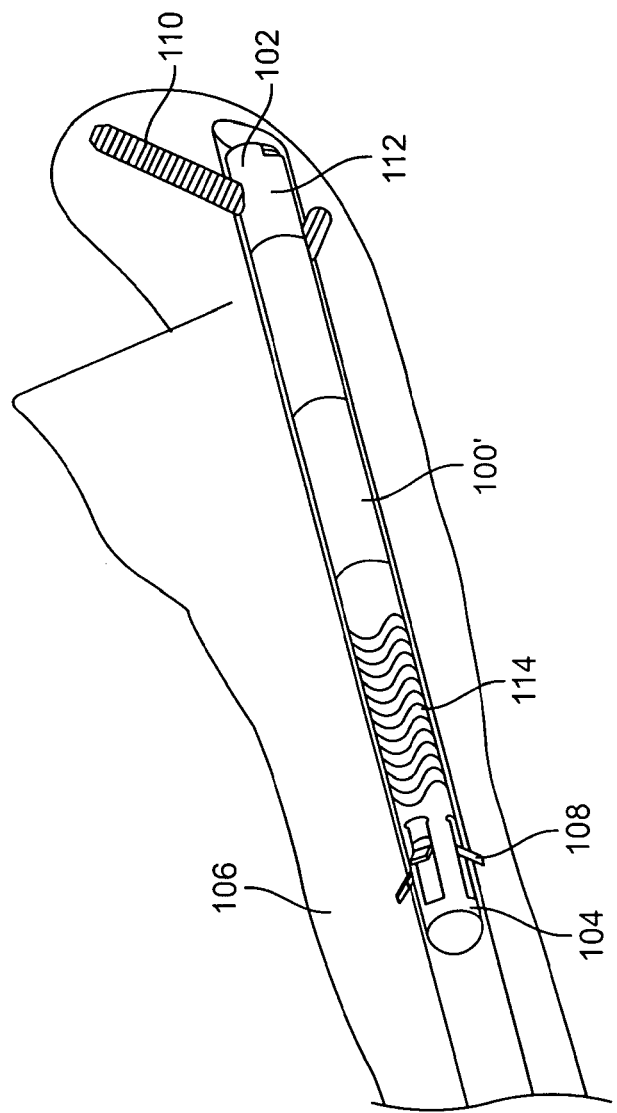
FIG. 9A is a perspective view of an alternative embodiment of the implanted device of FIG. 1.
Figure 9B:
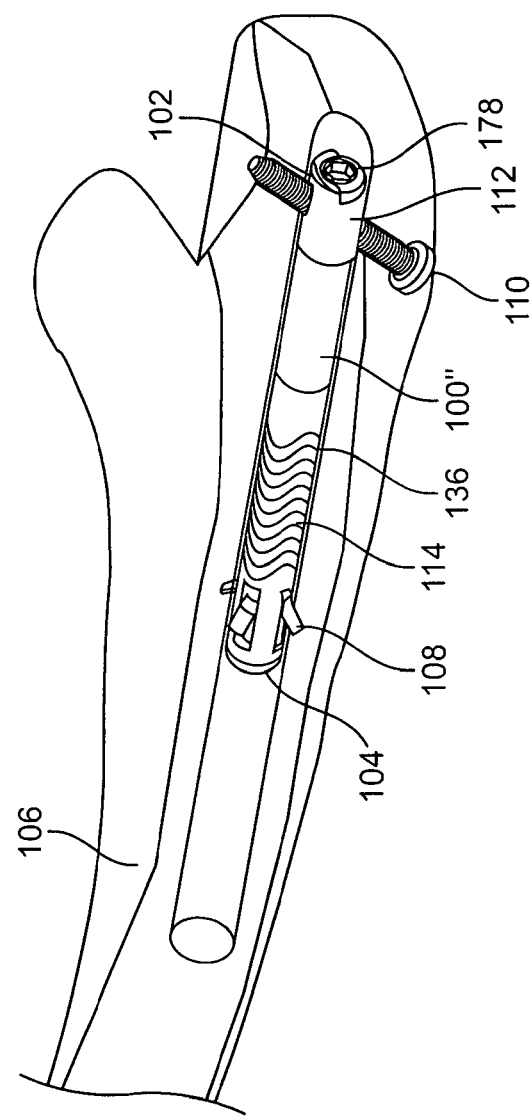
FIG. 9B is a perspective view of another alternative embodiment of the implanted device of FIG. 1.

FIGS. 9A and 9B show alternative embodiments similar to device 100 described above. Device 100' shown in FIG. 9A is essentially identical to device 100 described above but is shorter in length and utilizes a single anchor screw 110 at its proximal end 102. Device 100" shown in FIG. 9B is similar to device 100', but is shorter still. In various embodiments, the devices may be configured to have a nominal diameter of 3 mm, 4 mm, 5 mm or 6 mm. It is envisioned that all three device designs 100, 100' and 100" may each be provided in all three diameters such that the chosen device is best suited for the particular fracture(s) and anatomy in which it is implanted.

In accordance with the various embodiments of the present invention, the device may be made from a variety of materials such as metal, composite, plastic or amorphous materials, which include, but are not limited to, steel, stainless steel, cobalt chromium plated steel, titanium, nickel titanium alloy (nitinol), superelastic alloy, and polymethylmethacrylate (PMMA). The device may also include other polymeric materials that are biocompatible and provide mechanical strength, that include polymeric material with ability to carry and delivery therapeutic agents, that include bioabsorbable properties, as well as composite materials and composite materials of titanium and polyetheretherketone (PEEK™), composite materials of polymers and minerals, composite materials of polymers and glass fibers, composite materials of metal, polymer, and minerals.

Within the scope of the present invention, each of the aforementioned types of device may further be coated with proteins from synthetic or animal source, or include collagen coated structures, and radioactive or brachytherapy materials. Furthermore, the construction of the supporting framework or device may include radio-opaque markers or components that assist in their location during and after placement in the bone or other region of the musculo-skeletal systems.

Further, the reinforcement device may, in one embodiment, be osteo incorporating, such that the reinforcement device may be integrated into the bone.

In a further embodiment, there is provided a low weight to volume device deployed in conjunction with other suitable materials to form a composite structure in-situ. Examples of such suitable materials may include, but are not limited to, bone cement, high density polyethylene, Kapton®, polyetheretherketone(PEEK™), and other engineering polymers.

Once deployed, the device may be electrically, thermally, or mechanically passive or active at the deployed site within the body. Thus, for example, where the device includes nitinol, the shape of the device may be dynamically modified using thermal, electrical or mechanical manipulation. For example, the nitinol device may be expanded or contracted once deployed, to move the bone or other region of the musculo-skeletal system or area of the anatomy by using one or more of thermal, electrical or mechanical approaches.

It is contemplated that the inventive implantable device, tools and methods may be used in many locations within the body. Where the proximal end of a device in the anatomical context is the end closest to the body midline and the distal end in the anatomical context is the end further from the body midline, for example, on the humerus, at the head of the humerus (located proximal, or nearest the midline of the body) or at the lateral or medial epicondyle (located distal, or furthest away from the midline); on the radius, at the head of the radius (proximal) or the radial styloid process (distal); on the ulna, at the head of the ulna (proximal) or the ulnar styloid process (distal); for the femur, at the greater trochanter (proximal) or the lateral epicondyle or medial epicondyle (distal); for the tibia, at the medial condyle (proximal) or the medial malleolus (distal); for the fibula, at the neck of the fibula (proximal) or the lateral malleoulus (distal); the ribs; the clavicle; the phalanges; the bones of the metacarpus; the bones of the carpus; the bones of themetatarsus; the bones of the tarsus; the sternum and other bones, the device may be adapted and configured with adequate internal dimension to accommodate mechanical fixation of the target bone and to fit within the anatomical constraints. As will be appreciated by those skilled in the art, access locations other than the ones described herein may also be suitable depending upon the location and nature of the fracture and the repair to be achieved. Additionally, the devices taught herein are not limited to use on the long bones listed above, but can also be used in other areas of the body as well, without departing from the scope of the invention. It is within the scope of the invention to adapt the device for use in flat bones as well as long bones.

Figure 10A:
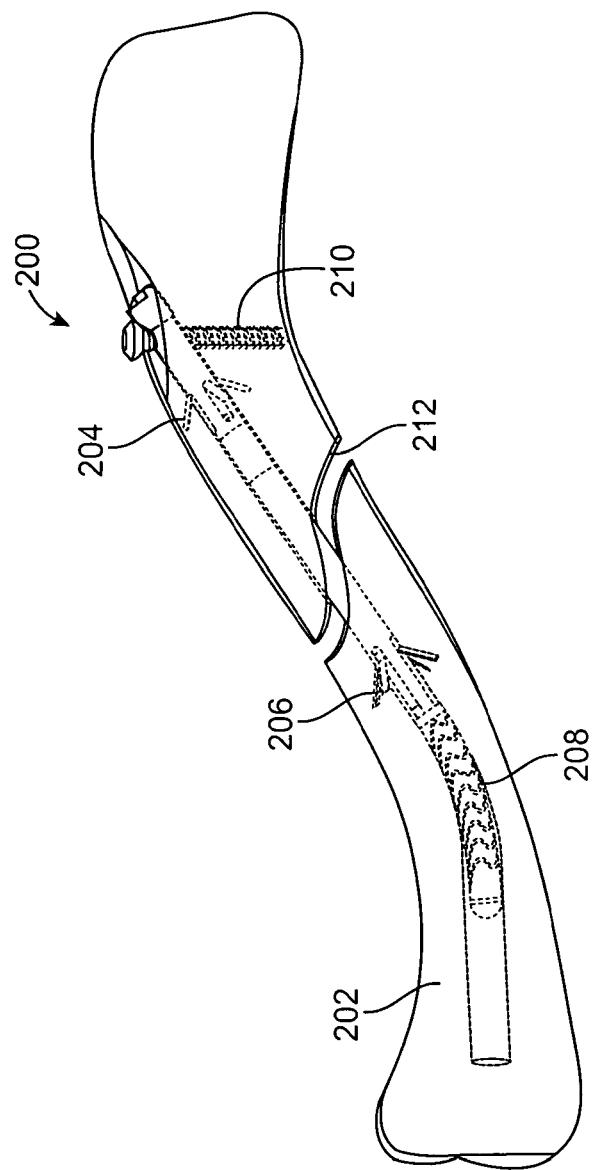
FIG. 10A is a perspective view of another embodiment of a bone fixation device shown deployed in a fractured clavicle.
Figure 10C:
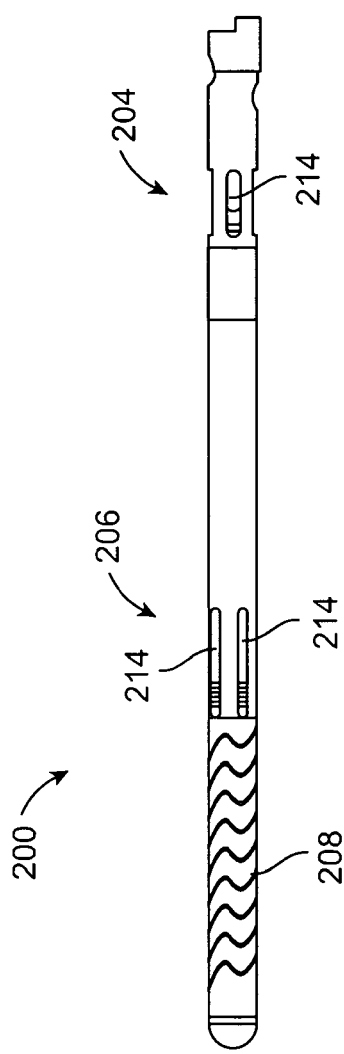
FIG. 10C is a side elevation view of the device shown in FIG. 10A shown in a retracted or undeployed state.
Figure 10D:
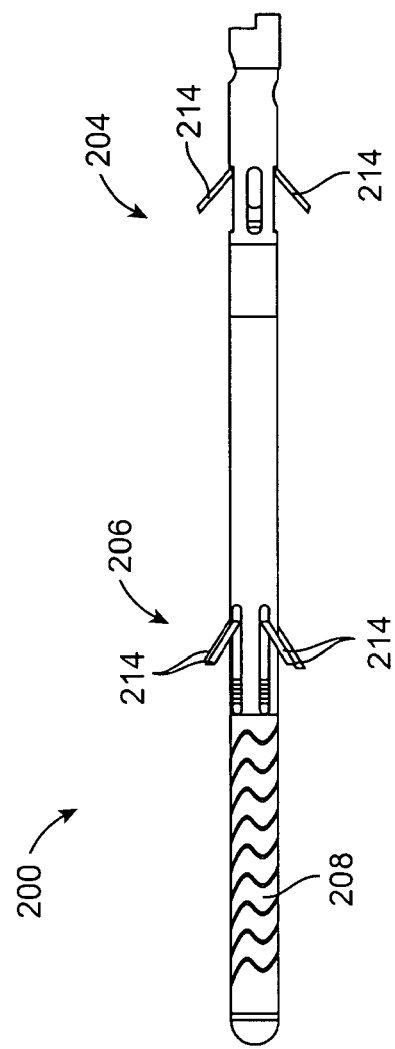
FIG. 10D is a side elevation view of the device shown in FIG. 10A shown in a deployed state.

FIGS. 10A-10I show another embodiment of a bone fixation device constructed according to aspects of the invention. FIG. 10A is a perspective view showing the exemplary device 200 deployed in a fractured clavicle 202. Device 200 is similar to device 100 described above and shown in FIGS. 1-7, but has a gripper 204 located near its proximal end, another gripper 206 located at a more distal location, and a flexible-to-rigid body portion 208 located near the distal end of the device. A bone screw 210 and gripper 204 are configured to secure device 200 inside bone 202 on the proximal side of fracture 212, while gripper 206 and flexible-to-rigid body portion 208 are configured to secure device 200 on the distal side of fracture 212. In other respects, construction and operation of device 200 is much like that of device 100 described above.

In this exemplary embodiment, each of the two grippers 204 and 206 has four outwardly expanding arms 214. These arms are spaced at 90 degree intervals around the circumference of the device body. The arms 214 of gripper 204 may be offset by 45 degrees from arms 214 of gripper 206 as shown in the figures to distribute the forces applied by grippers 204 and 206 on the bone 202. As shown in FIGS. 10E and 10F, a single actuator 216 may be used to deploy both grippers 204 and 206. Actuator 216 may also be used to axially compress flexible-to-rigid body portion 208 to make it substantially rigid. At least a portion of actuator 216 may be flexible to allow flexible-to-rigid body portion 208 to assume a curved shape, as best seen in FIGS. 10A and 10B. Alternatively, it may be desirable in some embodiments to have flexible-to-rigid body portion 208 maintain a straight or a curved configuration regardless of whether it is in a flexible or rigid state. In these embodiments, the actuator may be rigid and formed with the desired straight and/or curved shape to match the flexible-to-rigid body portion. In some embodiments, it may also be desirable to design at least a portion of the actuator with a high degree of axial elasticity to allow the actuator to continue to expand some gripper(s) and/or compress some flexible-to-rigid body portion(s) after other gripper(s) and/or flexible-to-rigid body portion(s) have already been fully deployed.

Figure 10G:
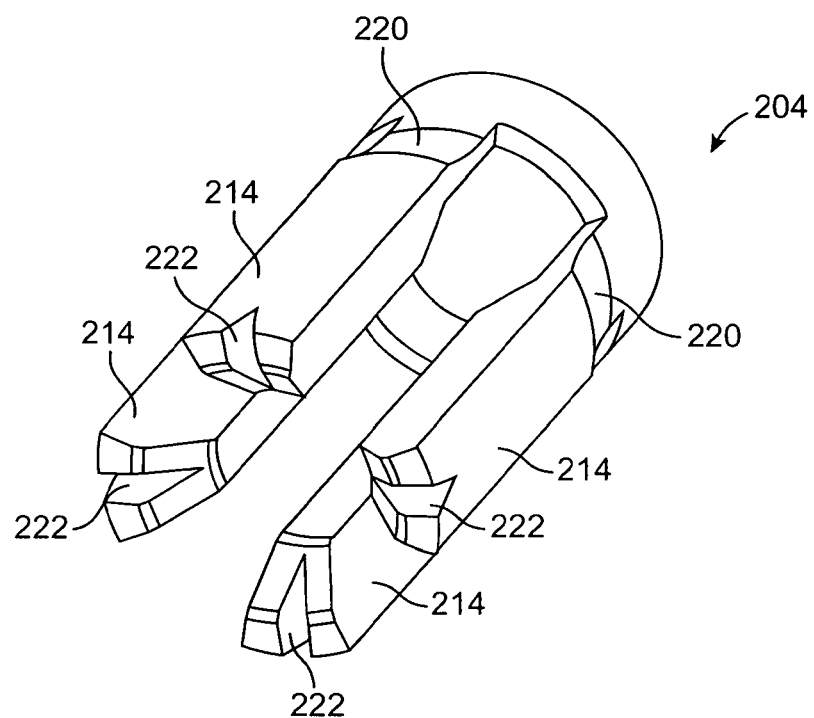
FIG. 10G is a perspective view of a gripper of the device shown in FIG. 10A shown in a retracted or undeployed state.
Figure 10H:
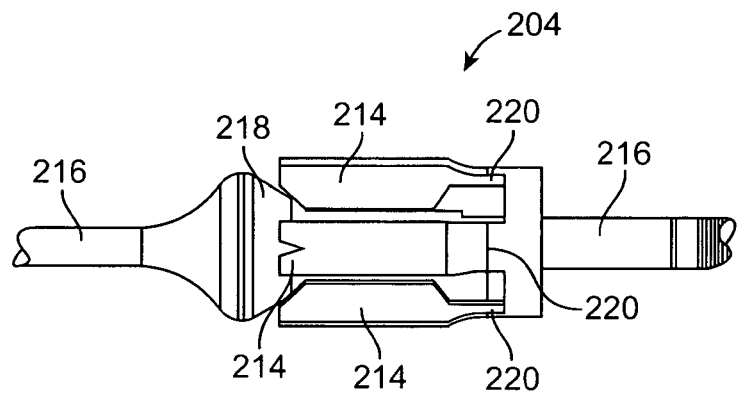
FIG. 10H is a side elevation view of a gripper and actuator of the device shown in FIG. 10A shown in a retracted or undeployed state.
Figure 10I:
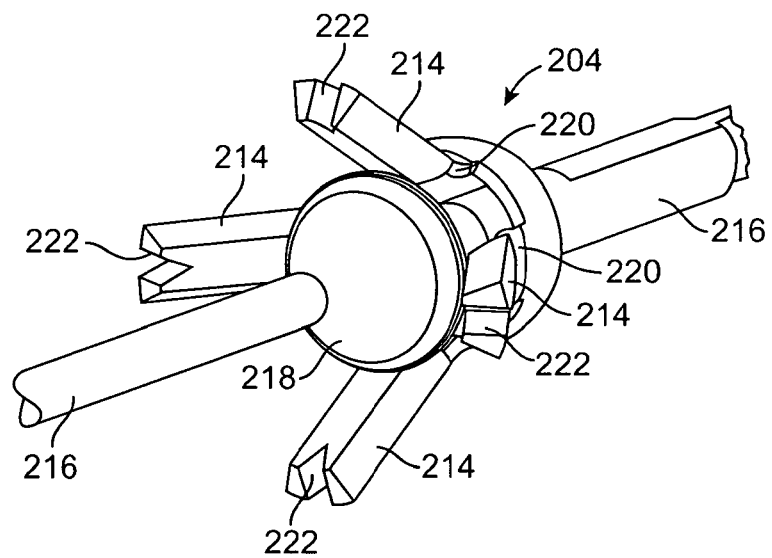
FIG. 10I is a perspective view of a gripper and actuator of the device shown in FIG. 10A shown in a deployed state.

Referring to FIGS. 10G-10I, further details of an exemplary gripper 204 are shown. FIGS. 10G and 10H show gripper 204 with bendable arms 214 in a retracted state. As cam 218 of actuator 216 is driven axially into the distal ramped ends of arms 214, arms 214 bend at thinned portions 220 to move radially outward toward the deployed position shown in FIG. 10I. Notches 222 may be provided in the distal ends of arms 214 as shown to allow arms 214 to better grip interior bone surfaces. Without departing from the scope of the invention, one, two, three, or more bendable arms may be used.

Figure 11A:
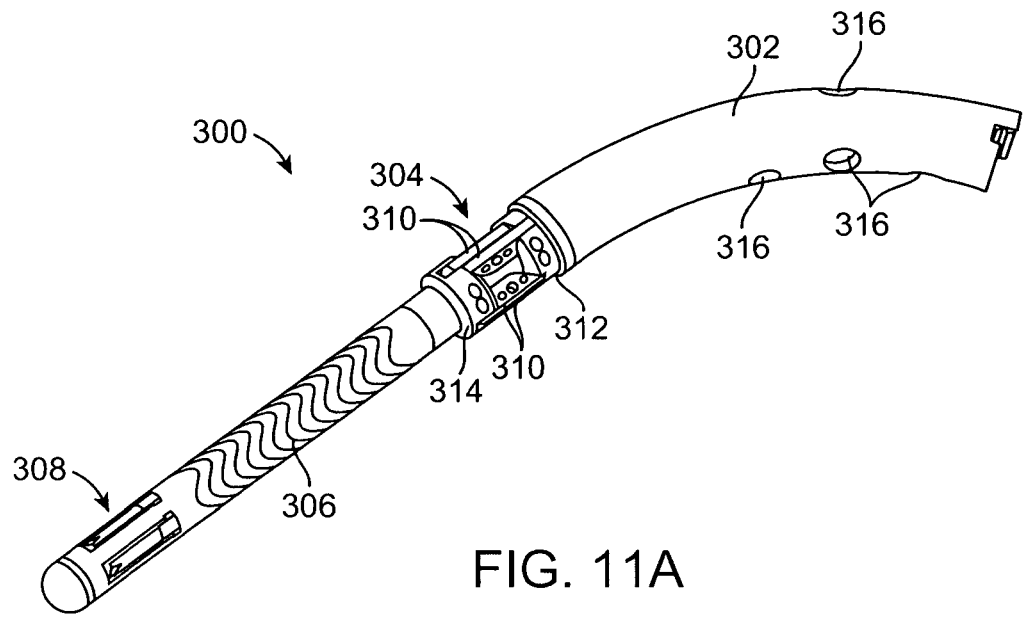
FIG. 11A is perspective view of another embodiment of a bone fixation device shown in a retracted or undeployed state.
Figure 11B:
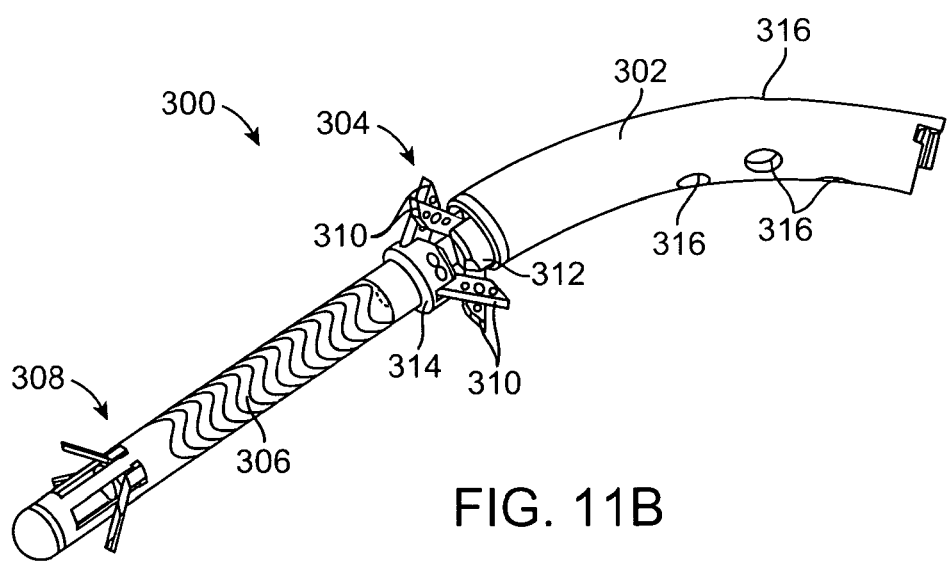
FIG. 11B is perspective view of the device shown in FIG. 11A shown in a deployed state.
Figure 11C:
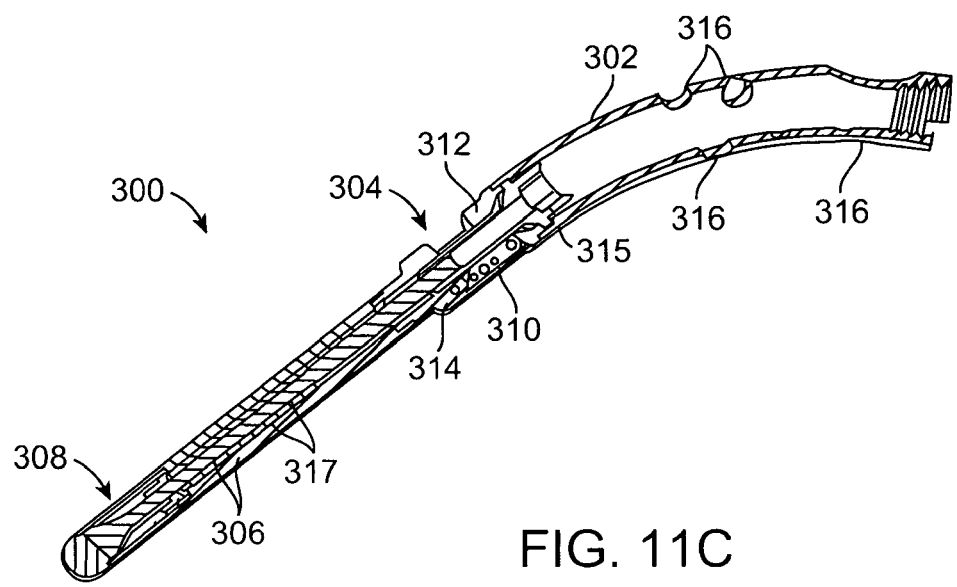
FIG. 11C is a cross-sectional view of the device shown in FIG. 11A shown in a retracted or undeployed state.
Figure 11D:
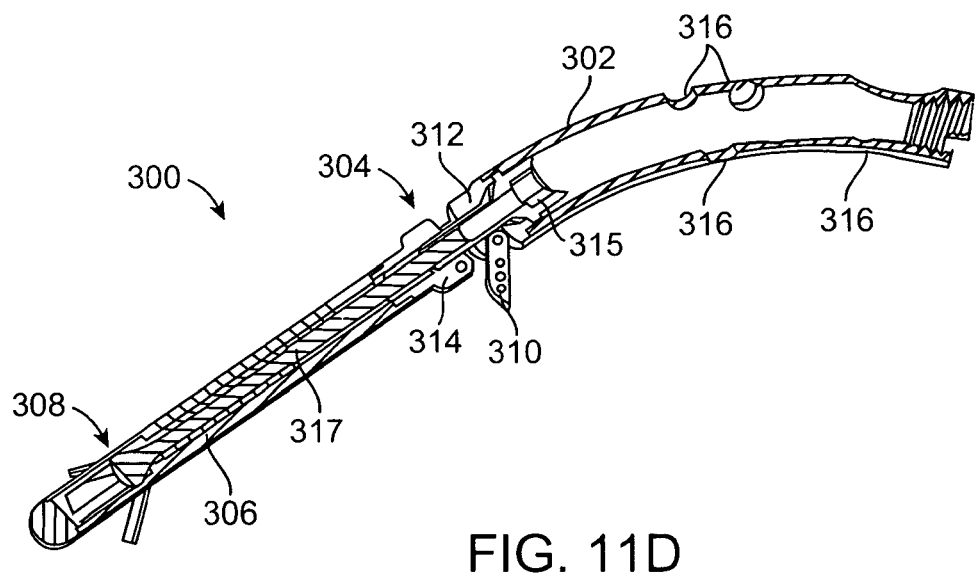
FIG. 11D is a cross-sectional view of the device shown in FIG. 11A shown in a deployed state.

Referring to FIGS. 11A-11D, another embodiment of a bone fixation device is shown. Device 300 includes a curved hub 302, proximal gripper 304, flexible-to-rigid body portion 306, and distal gripper 308. Distal gripper 308 is similar in construction and operation to grippers 204 and 206 described above. Proximal gripper 304 is provided with three pairs of scissor arms 310. Each pair of arms 310 is pivotably interconnected at a mid-portion by a pin. Each arm is pivotably connected with a pin to either proximal end piece 312 or distal end piece 314. When end pieces 312 and 314 are moved closer together, arms 310 pivot radially outward from an axially aligned retracted position, as shown in FIGS. 11A and 11C, to a deployed position, as shown in FIGS. 11B and 11D. In the deployed position, the distal ends of the six arms 310 engage an inner surface of a bone as previously described.

In operation, device 300, with grippers 304 and 308 in a retracted state, may be inserted into the intramedullary space within a bone, such as the radius. Device 300 may be inserted through a curved opening formed in the bone, such as an opening formed through a bony protuberance on a distal or proximal end or through the midshaft of the bone. Curved hub 302 may be configured with the same geometry of the curved opening in the bone, and when the flexible-to-rigid body portion 306 is in its flexible state, it can assume this same geometry. Once device 300 is in place inside the bone, actuator 315 (shown in FIGS. 11C and 11D) may be actuated from the proximal end of device 300 by turning drive member 317 in a manner similar to that previously described. Longitudinal movement of actuator 315 toward the proximal end of device 300 causes flexible-to-rigid body portion 306 to foreshorten and assume its rigid state, and causes grippers 304 and 308 to outwardly deploy against the bone. Bone screws may be inserted through holes 316 shown in curved hub 302 to secure the proximal end of device 300 to the bone. Further details of the construction and operation of a device similar to device 300 may be found in co-pending U.S. application Ser. No. 11/944,366 filed Nov. 21, 2007 and entitled Fracture Fixation Device, Tools and Methods.

Device 300 is an example of an embodiment utilizing mixed gripper types. In other words, this device uses one scissors-arm tripod gripper 304 and one bendable-arm gripper 308. Other embodiments of the invention (not shown) use various combinations of gripper(s) and/or flexible-to-rigid body portion(s). Further exemplary gripper embodiments are described in detail below. It is envisioned that virtually any combination of zero, one, two, or more grippers may be used in combination with zero, one, two or more flexible-to-rigid body portions to form a device adapted to a particular bone anatomy, fracture, disease state or fixation purpose. The grippers and/or flexible-to-rigid body portions may each be of identical or different construction, and may be placed together or at other locations along the device. Further, a straight, curved, flexible, rigid, or no hub at all may be used with the above combinations. Additionally, screws, K-wires, sutures or no additional fixation may be used with these various devices. The devices may be specially designed and constructed for a particular purpose or range of purposes. According to aspects of the invention, the components may also be designed to be interchangeable and/or produced in various sizes so that surgical kits may be provided. Such kits would allow surgical teams to select from a variety of components to build devices themselves, each suited to a particular patient's unique situation.

FIGS. 12A through 21B show alternative gripper embodiments that may be used with the above described bone fixation devices, or with similar devices. Each of the following gripper embodiments may be provided at one or more locations along the length of the device. Each gripper is designed to have a retracted state for allowing a bone fixation device to be inserted into a bone, and an expanded state to secure the device within the bone. Each gripper arrangement includes fixation elements that are in a radially inward position when in the retracted state. Upon axial compression of each of the grippers, the fixation elements are deployed radially outward to contact interior bone surfaces, such as those defining an intramedullary space along the longitudinal axis of the bone, as described above. Each gripper design may optionally be provided with a threaded end to engage an actuator for moving the gripper between the retracted and expanded states.

Referring to FIGS. 12A-12G, one alternative gripper embodiment is shown. Gripper 400 includes a proximal end piece 402 with two long arms 404 each pivotably connected at their proximal ends to proximal end piece 402 by a pin 406. (Again, the words "proximal" and "distal" are being used herein with reference to the surgeon rather than to the patient's anatomy.) Gripper 400 also includes a distal end piece 408 with two short arms 410 each pivotably connected at their proximal ends to distal end piece 408 by a pin 412. A distal portion of each long arm 404 is pivotably connected to a mid-portion of each short arm 410 by a pin 414, thereby forming two pairs of scissor-arms, each pair spanning between end pieces 402 and 408.

Figure 12A:
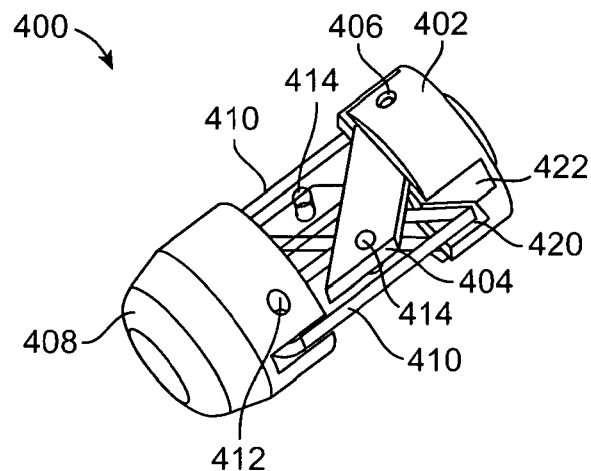
FIG. 12A is a perspective view showing an alternative gripper design in a retracted or undeployed state.
Figure 12B:
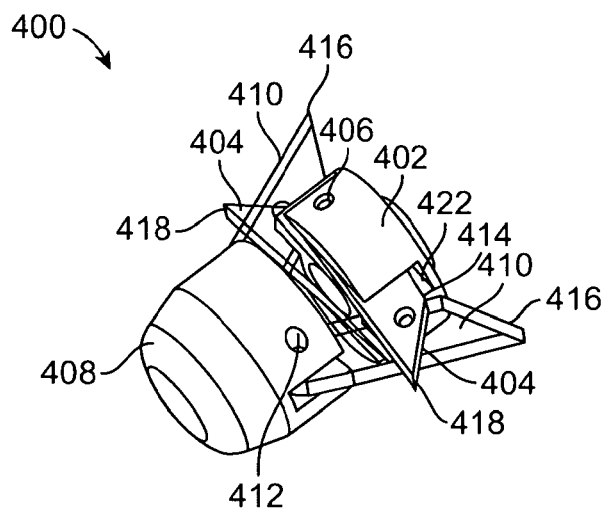
FIG. 12B is a perspective view showing the gripper of FIG. 12A in a deployed state.
Figure 12C:
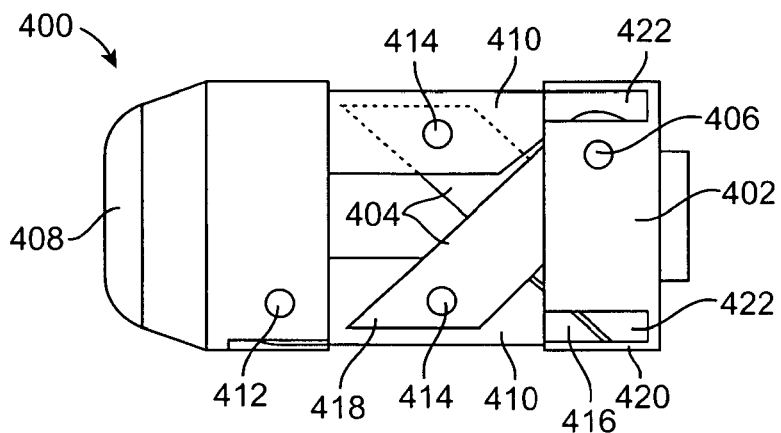
FIG. 12C is a side elevation view showing the gripper of FIG. 12A in a retracted or undeployed state.
Figure 12D:
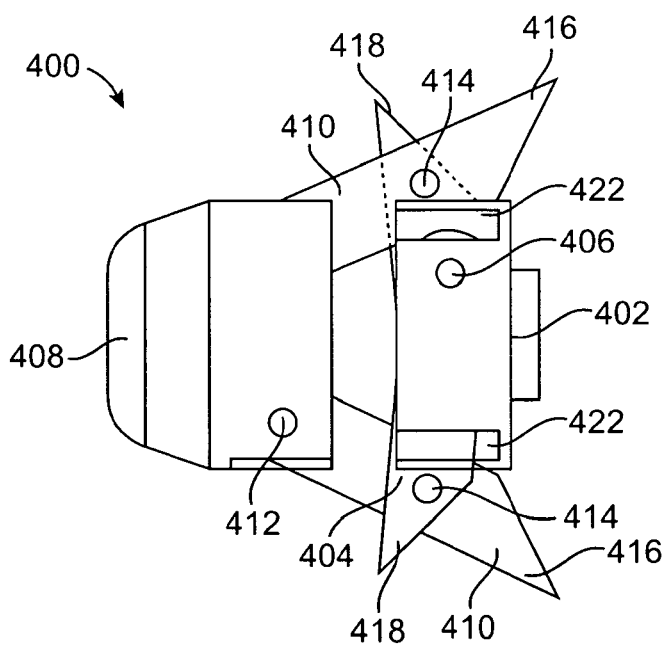
FIG. 12D is a side elevation view showing the gripper of FIG. 12A in a deployed state.
Figure 12E:
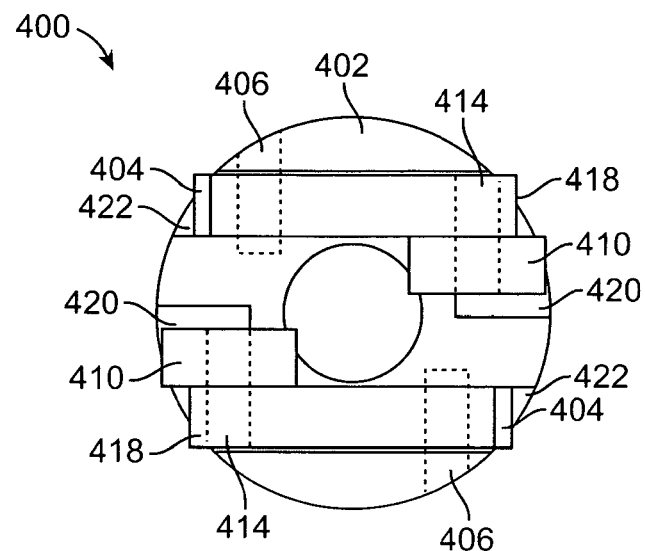
FIG. 12E is a proximally-looking end view (with an end piece removed for clarity) showing the gripper of FIG. 12A in a retracted or undeployed state.
Figure 12F:
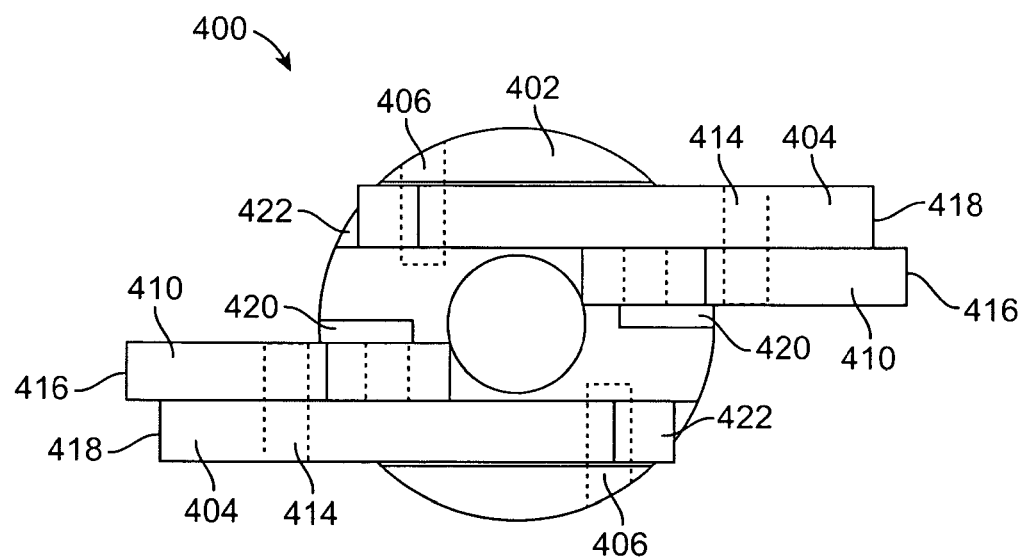
FIG. 12F is a proximally-looking end view (with an end piece removed for clarity) showing the gripper of FIG. 12A in a deployed state.
Figure 12G:
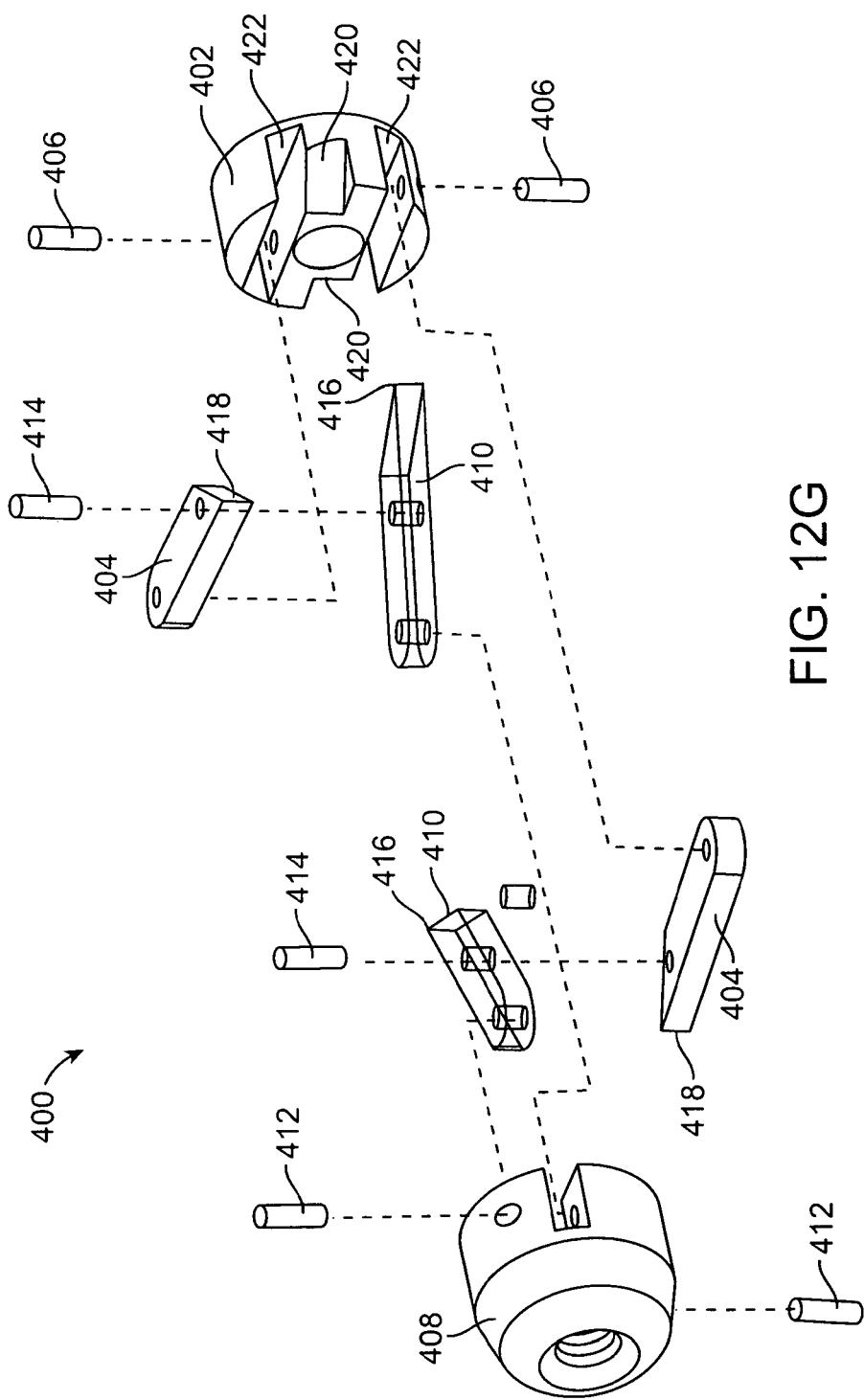
FIG. 12G is an exploded perspective view showing the gripper of FIG. 12A.

Gripper 400 is movable between a retracted state in which short arms 410 are substantially aligned with the longitudinal axis of gripper 400 (as shown in FIGS. 12A, 12C and 12E) and a deployed state in which the short arms are pivoted radially outward (as shown in FIGS. 12B, 12D and 12F). Gripper 400 is moved from the retracted state to the deployed state by axially compressing end pieces 402 and 408 towards one another, such as with a pull-wire or screw actuator as previously described. Gripper 400 may be returned from the deployed state to the retracted state by applying an axially tensile force to end pieces 402 and 408. In the deployed state, the distal ends 416 of short arms 410 engage the inner surface of the bone (not shown). Depending on the penetration depth of distal ends 416 of short arms 410 into the bone, the distal ends 418 of long arms 404 may provide additional bone gripping.

Proximal end piece 402 is provided with recesses 420 to receive distal ends 416 of short arms 410 when in the retracted position. Proximal end piece 402 is also provided with recesses 422 to receive long arms 404, particularly when in the deployed position.

The particular arrangement of gripper 400 provides high contact force even at low deployment angles. This is achieved by the long moment arms of long arms 404 crossing over the center of gripper 400 to create higher compressive forces. Therefore, this arrangement does not need to expand as much as the scissors gripper 304 described previously to become effective. By comparison, gripper 400 has a large difference in direction and distance at the root of the center-line compressive forces running along the two arms to create a large expansive moment that produces a large contact force even when the device is just starting to expand.

Referring to FIGS. 13A-13H, another gripper embodiment 500 is shown. Gripper 500 is similar to gripper 400 described above in that it includes high moment arms crossing over the centerline of the gripper to provide high contact forces even at low expansion angles. Gripper 500, however, includes three sets of scissor-arm pairs instead of two, providing two contact areas every 120 degrees around the gripper instead of every 180 degrees as does gripper 400. While embodiments having two and three sets of gripper arms are shown, other embodiments of the invention (not shown) may use only a single set of arms or more than three sets. Additionally, while the arm sets shown each have two arms, it is envisioned that each "set" of arms may include a single arm pinned to the two end pieces, or more than two arms.

Gripper 500 includes a first end piece 502 with three long arms 504 each pivotably connected at their proximal ends to first end piece 502 by a pin 506. First end piece 502 is provided with recesses 520 to receive long arms 504, as best seen in FIG. 13E. Gripper 500 also includes a second end piece 508 with three short arms 510 each pivotably connected at their proximal ends to second end piece 508 by a pin 512. Second end piece 508 is provided with recesses 522 to receive short arms 510. A distal portion of each long arm 504 is pivotably connected to a distal portion of each short arm 510 by a pin 514, thereby forming three pairs of scissor-arms, each pair spanning between end pieces 502 and 508.

Figure 13A:
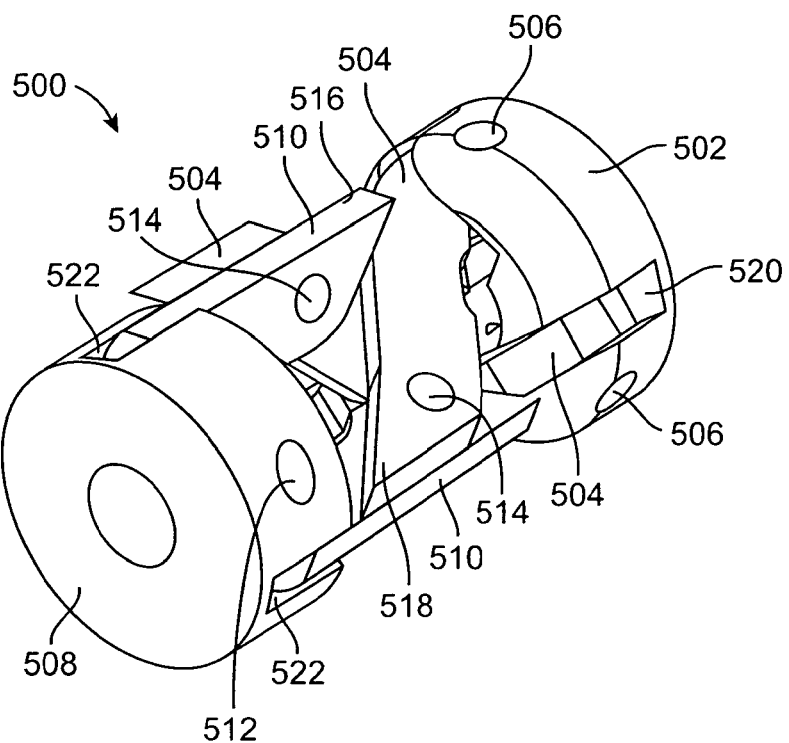
FIG. 13A is a perspective view showing another alternative gripper design in a retracted or undeployed state.
Figure 13B:
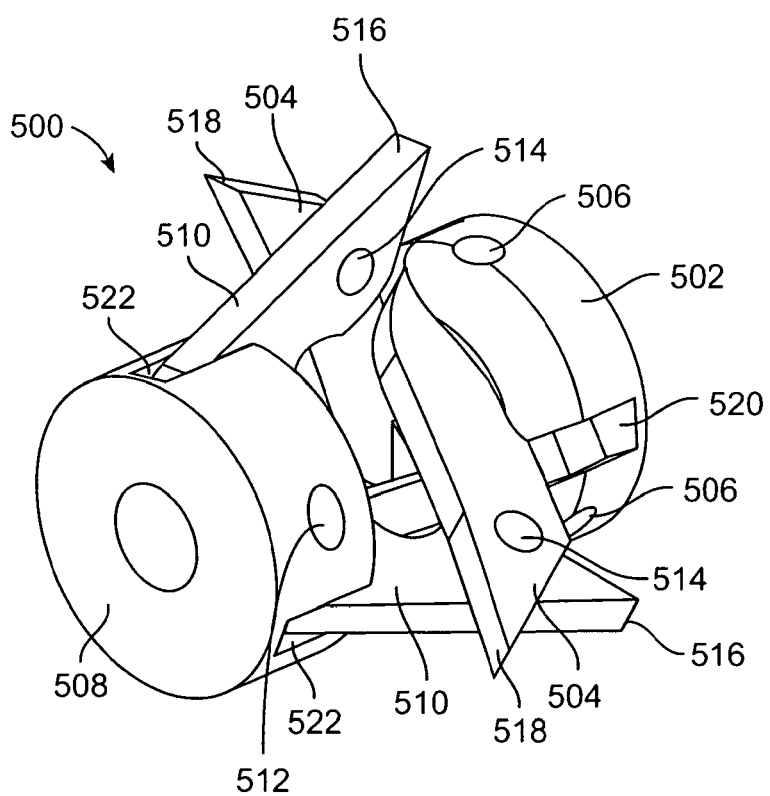
FIG. 13B is a perspective view showing the gripper of FIG. 13A in a deployed state.
Figure 13C:
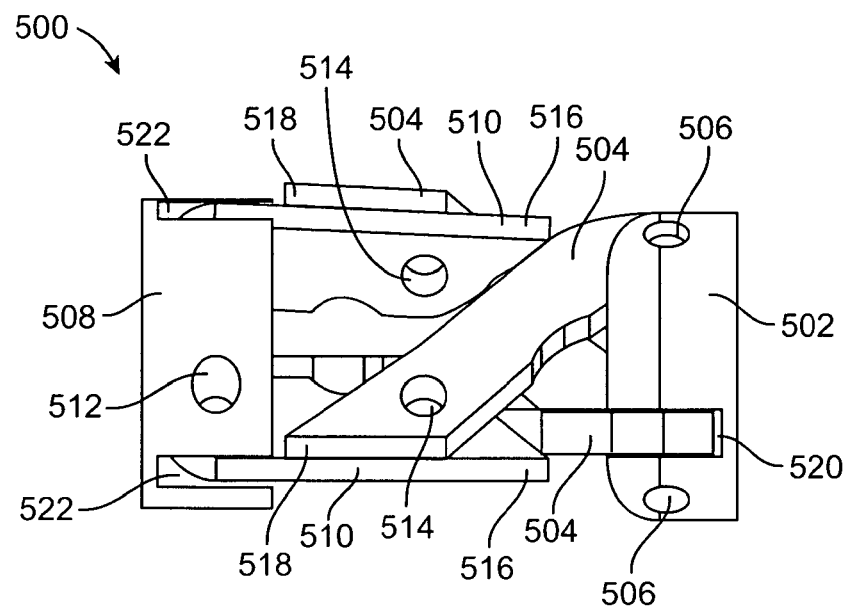
FIG. 13C is a side elevation view showing the gripper of FIG. 13A in a retracted or undeployed state.
Figure 13D:
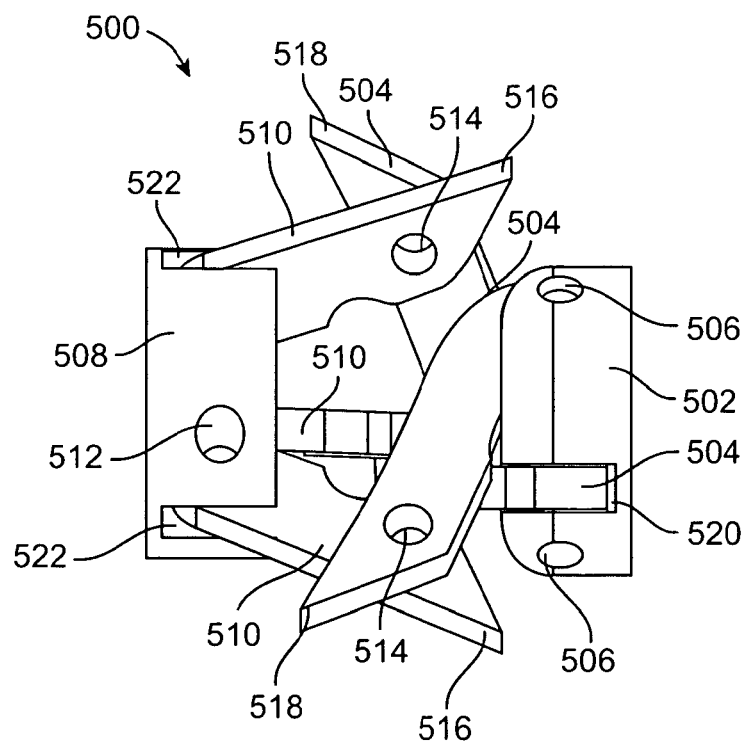
FIG. 13D is a side elevation view showing the gripper of FIG. 13A in a deployed state.
Figure 13E:
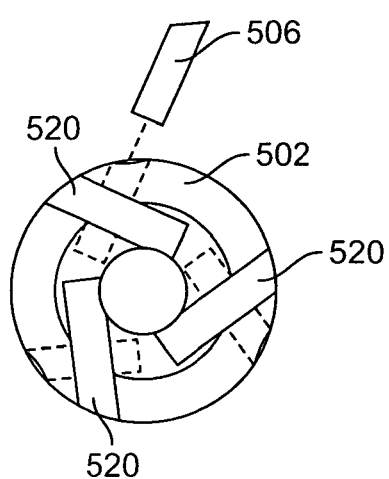
FIG. 13E is an end view showing an end component of the gripper of FIG. 13A.
Figure 13F:
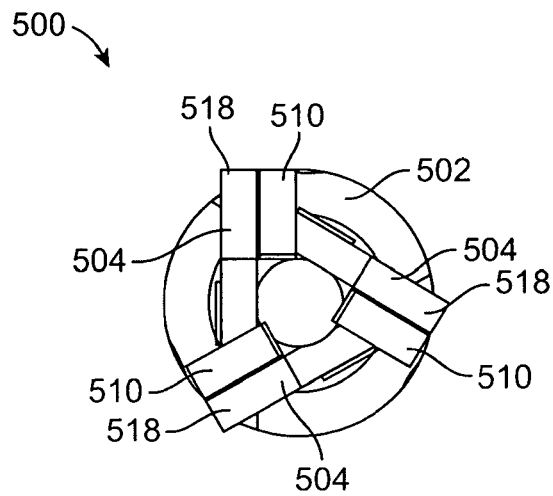
FIG. 13F is an end view (with an end component removed for clarity) showing the gripper of FIG. 13A in a retracted or undeployed state.
Figure 13G:
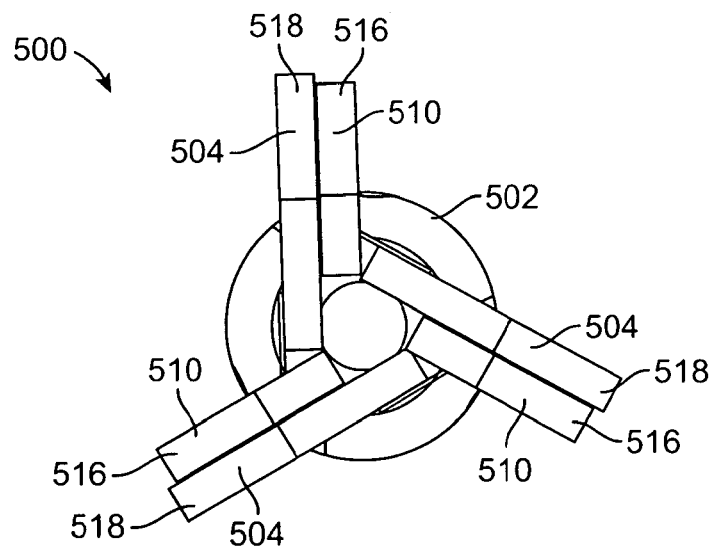
FIG. 13G is an end view (with an end component removed for clarity) showing the gripper of FIG. 13A in a deployed state.
Figure 13H:
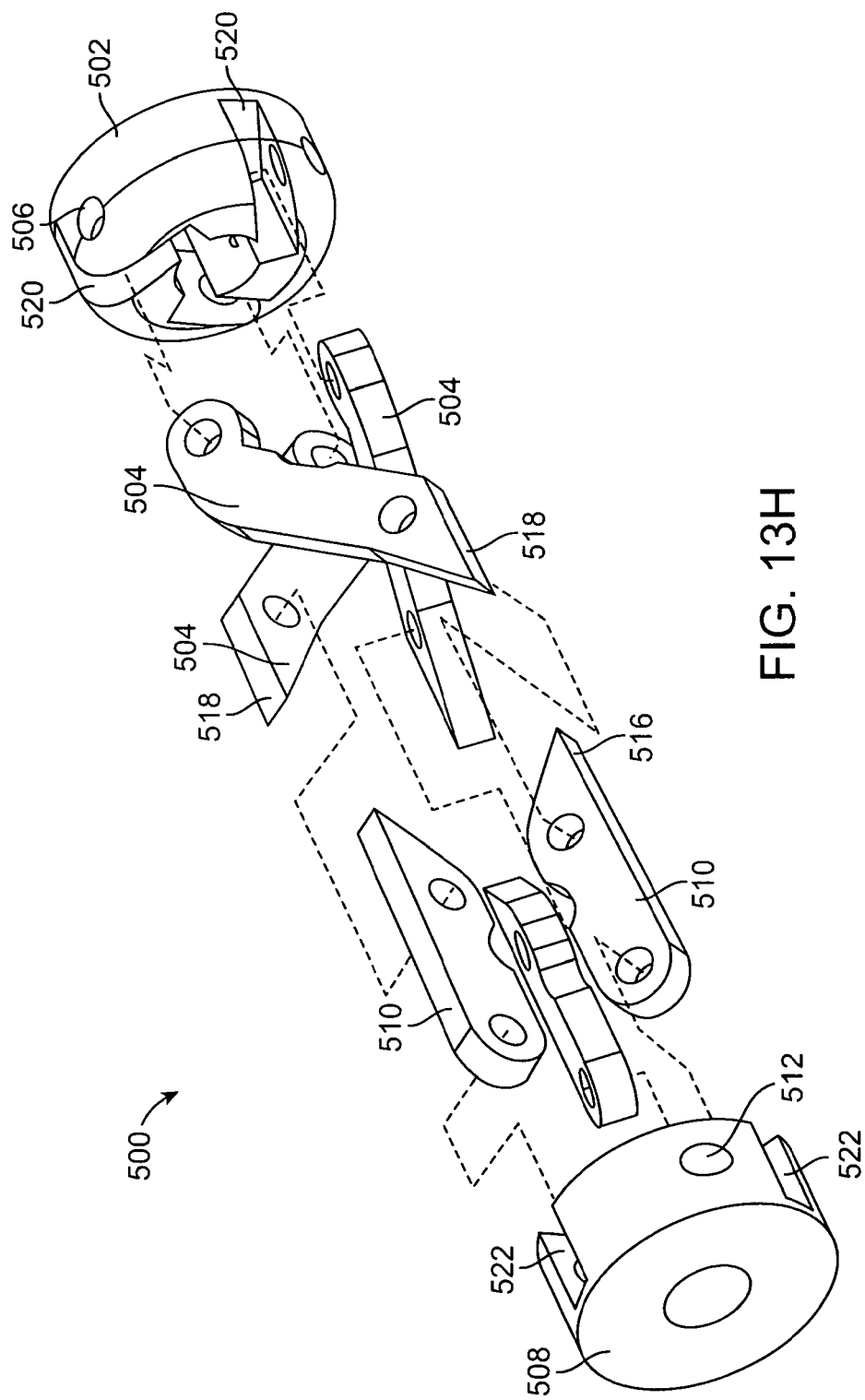
FIG. 13H is an exploded perspective view showing the gripper of FIG. 13A.

Gripper 500 is movable between a retracted state in which short arms 510 are substantially aligned with the longitudinal axis of gripper 500 (as shown in FIGS. 13A, 13C and 13F) and a deployed state in which the short arms 510 are pivoted radially outward (as shown in FIGS. 13B, 13D and 13G). Gripper 500 may be moved from the retracted state to the deployed state by axially compressing end pieces 502 and 508 towards one another, such as with an actuator as previously described. Gripper 500 may be returned from the deployed state to the retracted state by applying an axially tensile force to end pieces 502 and 508. In the deployed state, the distal ends 516 of short arms 510 and the distal ends 518 of long arms 504 engage the inner surface of the bone (not shown). Notches may be formed on the inside edges of each of the arms as shown so that they do not interfere with other components when in the retracted or deployed positions. Advantages of gripper 500 include a high gripping force at low radial expansion, and an ability to stabilize a bone fixation device in an intramedullary space having a circular or elliptical cross-section by gripping at three locations around the circumference.

Figure 14A:
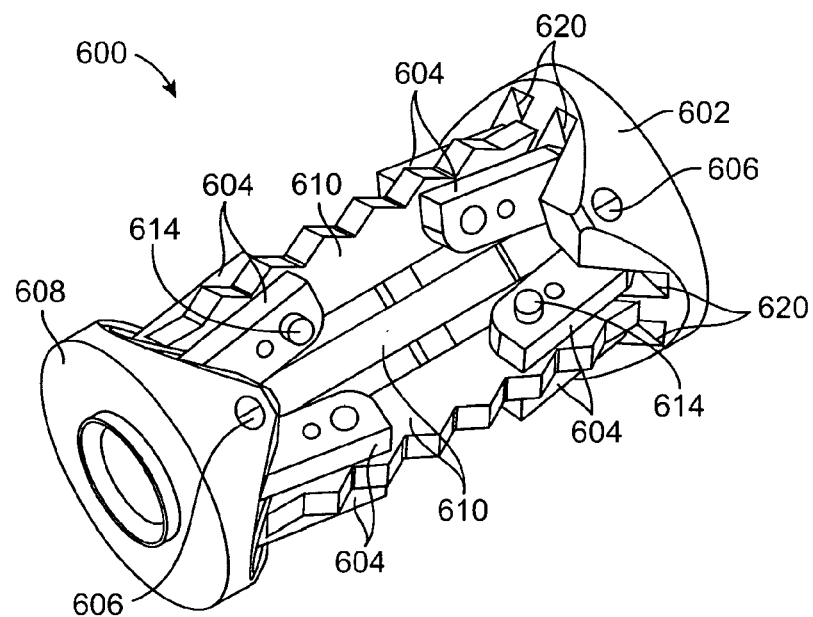
FIG. 14A is a perspective view showing another alternative gripper design in a retracted or undeployed state.
Figure 14B:
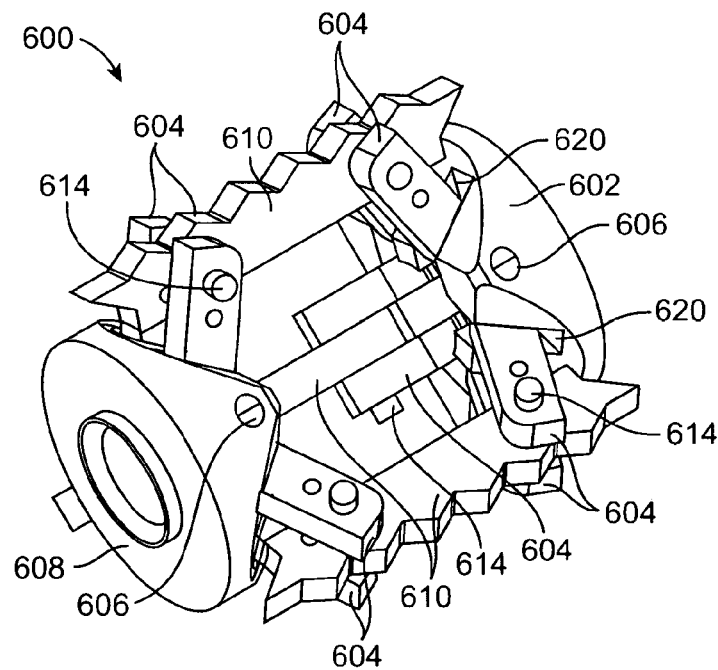
FIG. 14B is a perspective view showing the gripper of FIG. 14A in a deployed state.
Figure 14C:
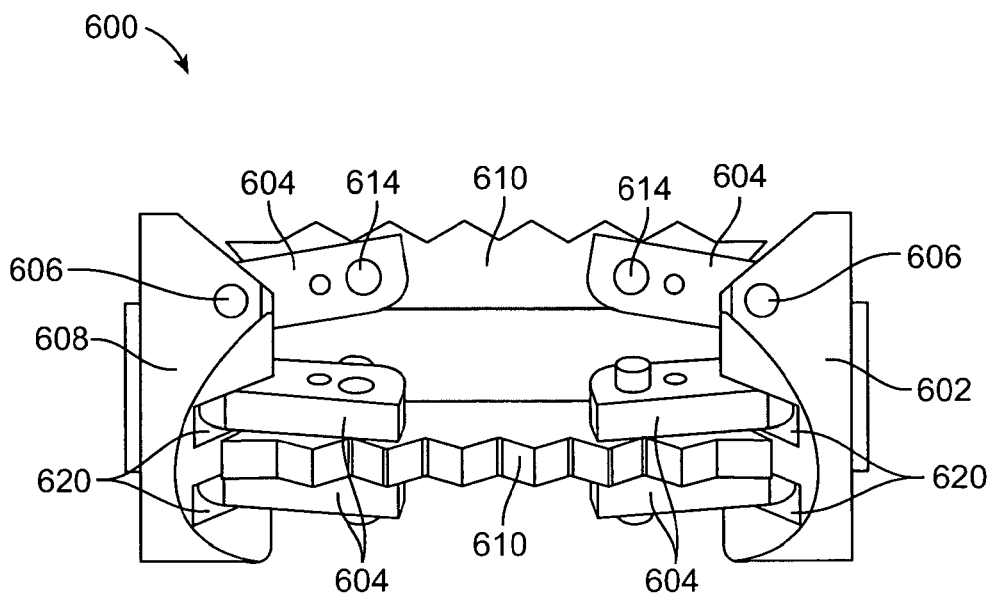
FIG. 14C is a side elevation view showing the gripper of FIG. 14A in a retracted or undeployed state.
Figure 14D:
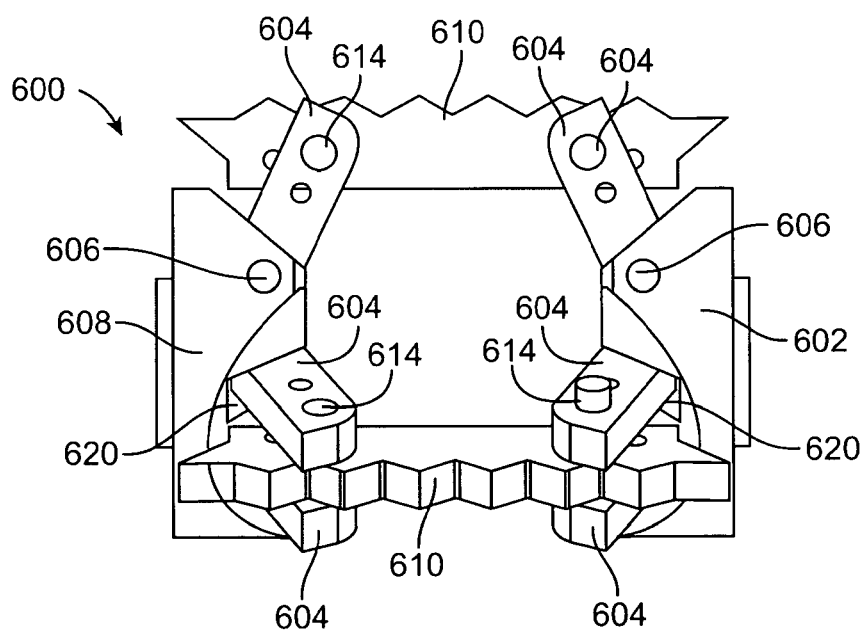
FIG. 14D is a side elevation view showing the gripper of FIG. 14A in a deployed state.
Figure 14E:
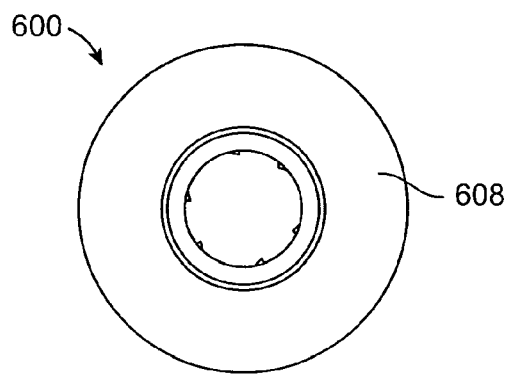
FIG. 14E is an end view showing the gripper of FIG. 14A in a retracted or undeployed state.
Figure 14F:
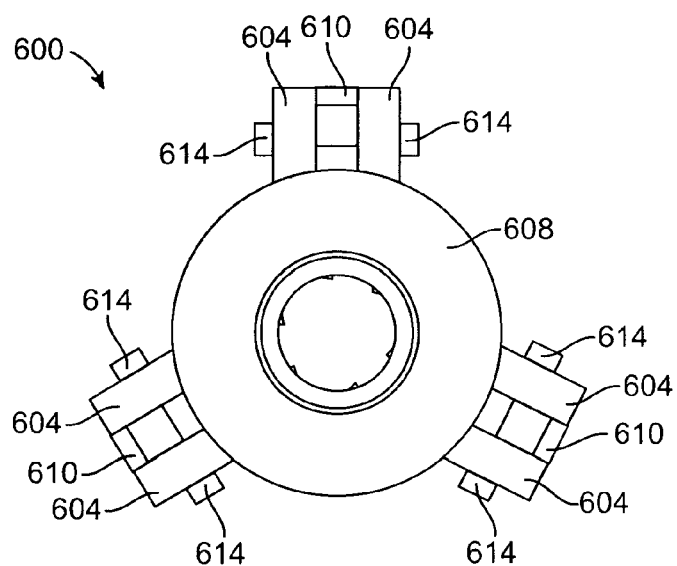
FIG. 14F is an end view showing the gripper of FIG. 14A in a deployed state.
Figure 14G:
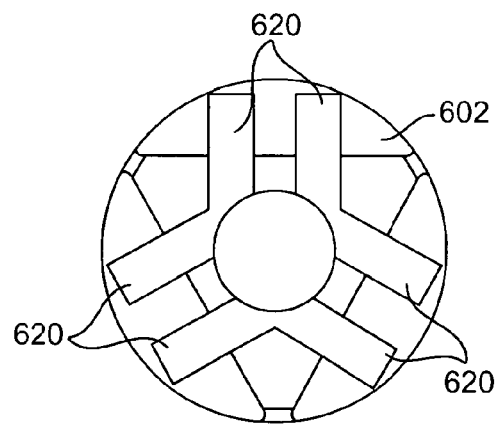
FIG. 14G is an end view showing an end component of the gripper of FIG. 14A.
Figure 14H:
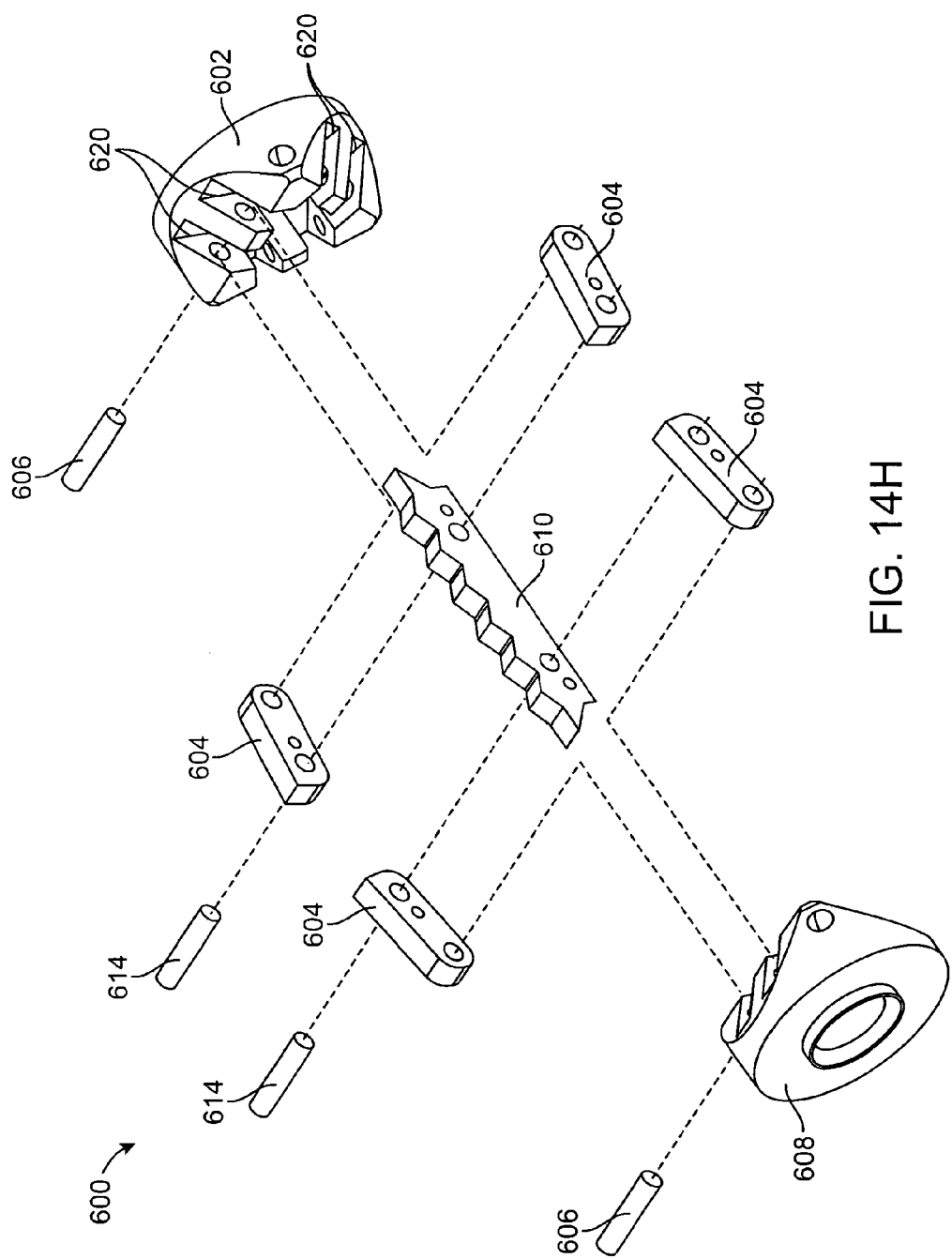
FIG. 14H is an exploded perspective view showing the gripper of FIG. 14A with only one set of gripper arms shown for clarity.

Referring to FIGS. 14A-14H, another gripper embodiment 600 is shown. Gripper 600 includes a first end piece 602 with three pairs of short arms 604 each pivotably connected at their proximal ends to first end piece 602. First end piece 602 is provided with six recesses 620 to receive short arms 604, as best seen in FIG. 14G. A pin 606 is used to pivotably secure each of the three pairs of short arms 604 to first end piece 602. Gripper 600 also includes a second end piece 608, which may be constructed to be identical to first end piece 602. Second end piece 608 also includes six recesses 620 to receive another three pairs of short arms 604. These additional three pairs of short arms 604 are pivotably secured at their proximal ends to second end piece 608 with three more pins 606. A distal end of each pair of short arms 604 connected to first end piece 602 is pivotably connected to one end of a long arm 610 by a pin 614. In a similar manner, a distal end of each pair of short arms 604 connected to second end piece 608 is pivotably connected to the opposite end of a long arm 610 by a pin 614. This arrangement forms three sets of arms spanning between first end piece 602 and second end piece 608. For clarity, only one of these three sets of arms is shown in FIG. 14H. As seen in FIG. 14H, each set of arms includes one long arm 610 and four short arms 604, all pivotably interconnected by two pins 614 and pivotably secured to the end pieces 602 and 608 by two pins 606. In other embodiments (not shown), each set of arms may include two long arms 610 instead of one, and/or two short arms 604 instead of four (one short arm 604 located at each end of the long arm(s) 610). Also, in other embodiments, one, two, four, or more sets of arms may be used instead of three. Radially outward facing surfaces of long arms 610 may be provided with serrations as shown for increased bone gripping capability.

Gripper 600 is movable between a retracted state in which long arms 610 are substantially aligned with the longitudinal axis of gripper 600 and in a radially inward position (as shown in FIGS. 14A, 14C and 14E) and a deployed state in which long arms 610 remain substantially aligned with the gripper axis but are moved to a radiallly outward position by pivoting short arms 604 (as shown in FIGS. 14B, 14D and 14F). Gripper 600 may be moved from the retracted state to the deployed state by axially compressing end pieces 602 and 608 towards one another, such as with an actuator as previously described. Gripper 600 may be returned from the deployed state to the retracted state by applying an axially tensile force to end pieces 602 and 608. In the deployed state, outwardly facing serrations of long arms 610 and the distal ends of short arms 604 engage the inner surface of the bone (not shown). The arrangement of gripper 600 distributes the radial pressure of the gripping arms over a larger cylinder within the bone. Three lines of contact are formed, spaced at every 120 degrees. Small holes may be provided in arms 604 and 610 as shown, and positioned such that the holes align when the gripper is in the retracted state. By inserting small pins or wires into the holes, the gripper may be temporarily locked in the retracted state. This may be useful when an intramedullary device requires significant pushing force to insert into the bone.

Figure 15A:
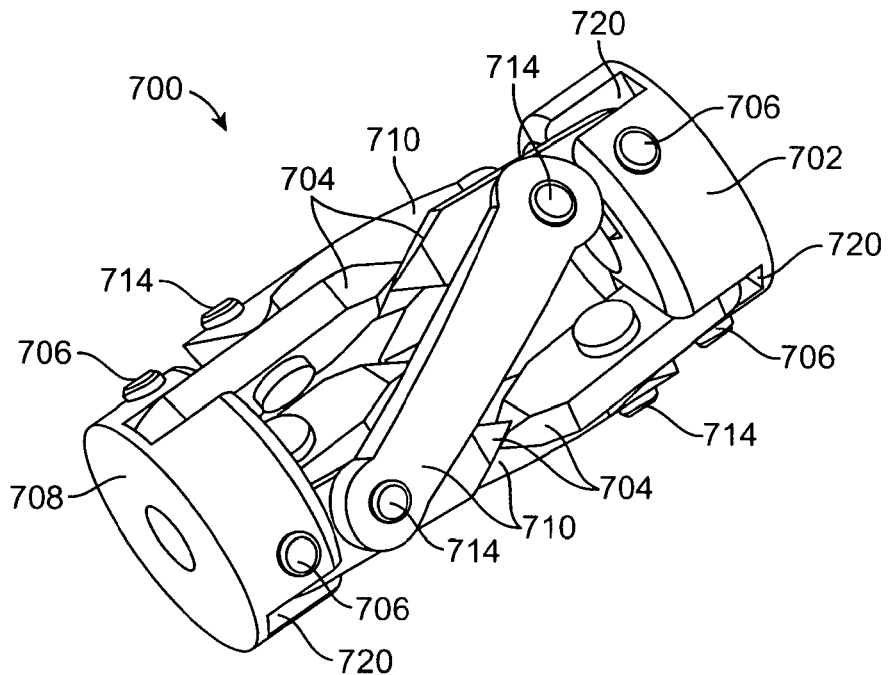
FIG. 15A is a perspective view showing another alternative gripper design in a retracted or undeployed state.
Figure 15B:
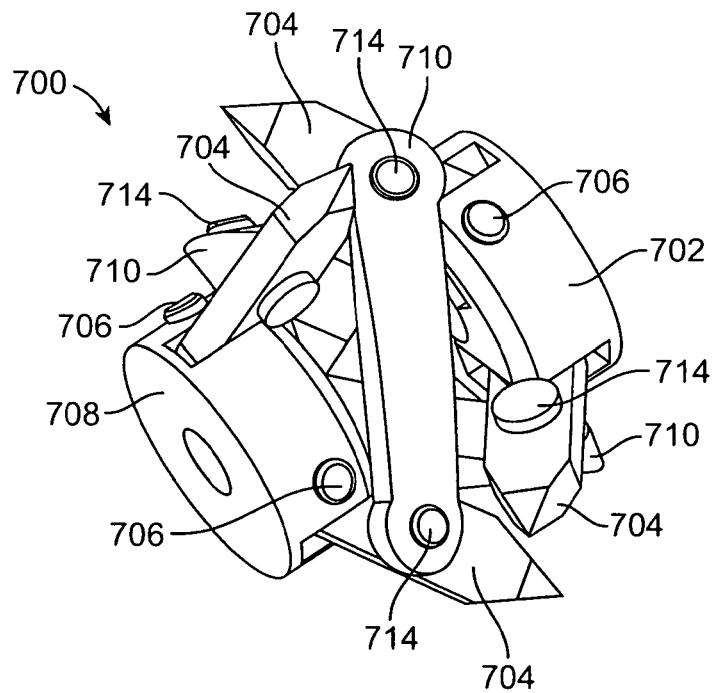
FIG. 15B is a perspective view showing the gripper of FIG. 15A in a deployed state.
Figure 15C:
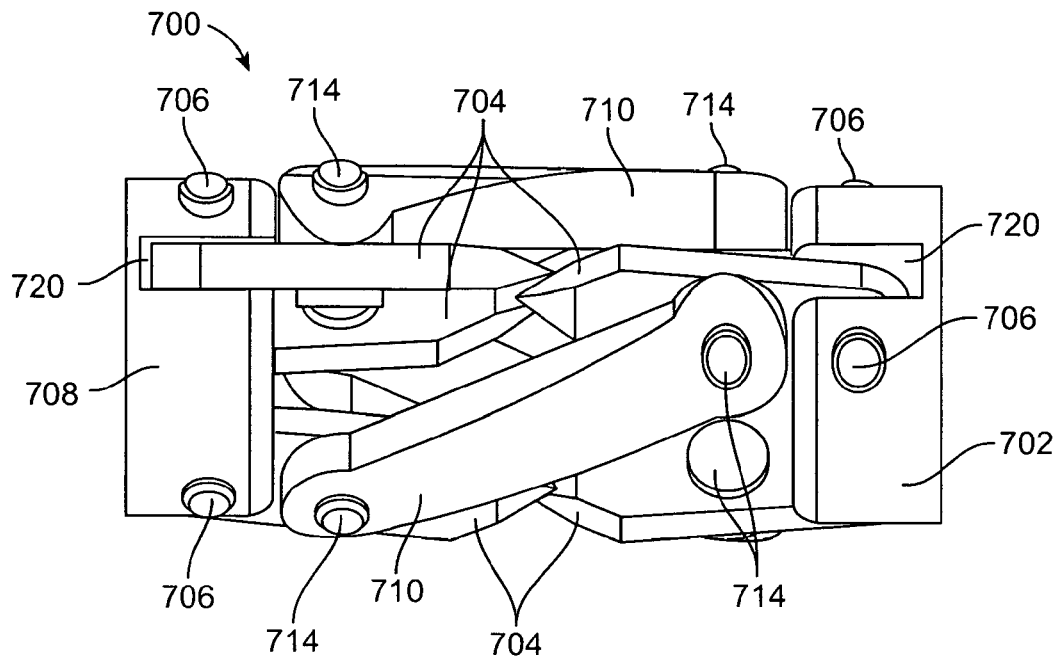
FIG. 15C is a side elevation view showing the gripper of FIG. 15A in a retracted or undeployed state.
Figure 15D:
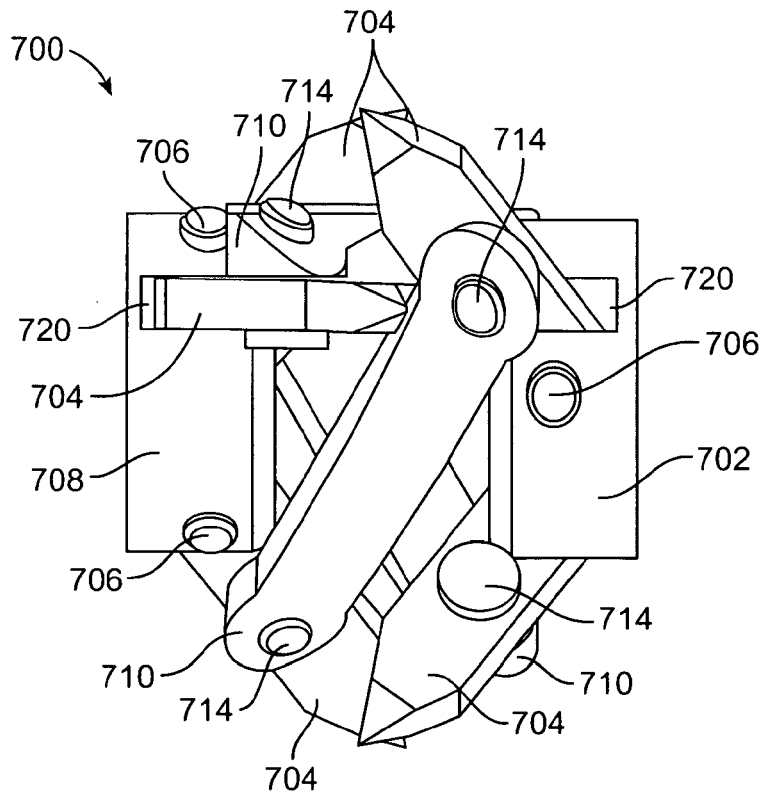
FIG. 15D is a side elevation view showing the gripper of FIG. 15A in a deployed state.
Figure 15E:
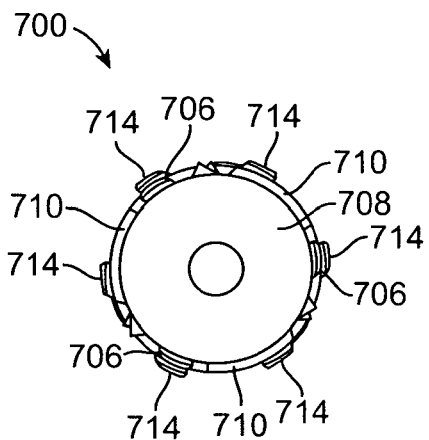
FIG. 15E is an end view showing the gripper of FIG. 15A in a retracted or undeployed state.
Figure 15F:
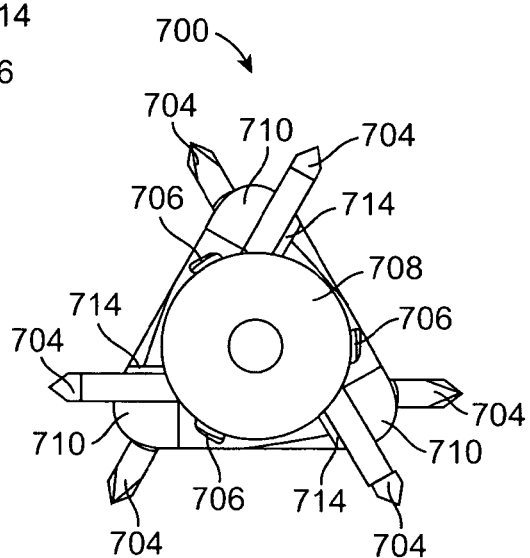
FIG. 15F is an end view showing the gripper of FIG. 15A in a deployed state.
Figure 15G:
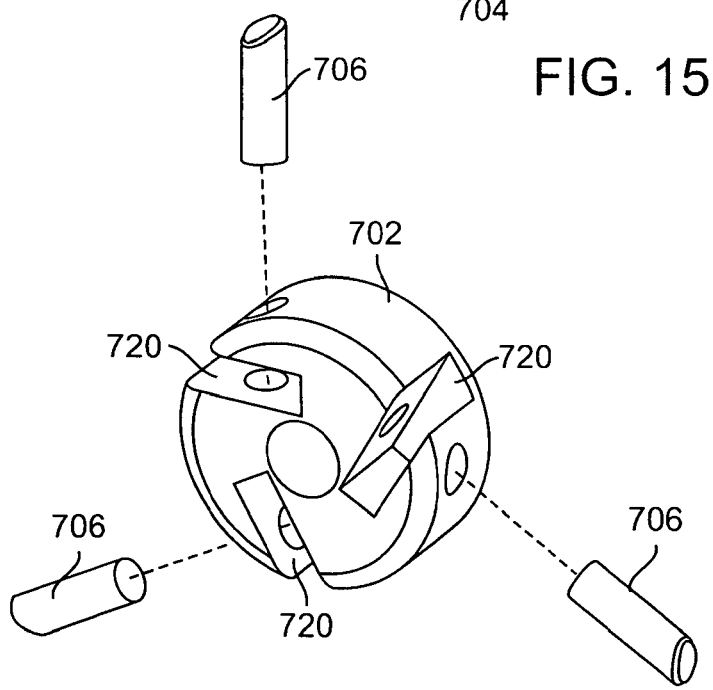
FIG. 15G is an exploded perspective view showing an end component of the gripper of FIG. 15A with arm-mounting pins.

Referring to FIGS. 15A-15H, another gripper embodiment 700 is shown. Gripper 700 includes a first end piece 702 with three short arms 704 each pivotably connected at their proximal ends to first end piece 702. First end piece 702 is provided with three recesses 720 to receive short arms 704, as best seen in FIG. 15G. Pins 706 are used to pivotably secure each of the three short arms 704 to first end piece 702. Gripper 700 also includes a second end piece 708, which may be constructed to be identical to first end piece 702. Second end piece 708 also includes three recesses 720 to receive another three short arms 704. These additional three short arms 704 are pivotably secured at their proximal ends to second end piece 708 with three more pins 706. A distal end of each short arm 704 connected to first end piece 702 is pivotably connected to one end of a long arm 710 by a pin 714. In a similar manner, a distal end of each short arm 704 connected to second end piece 708 is pivotably connected to the opposite end of a long arm 710 by a pin 714. This arrangement forms three sets of arms spanning between first end piece 702 and second end piece 708. For clarity, only one of these three sets of arms is shown in FIG. 15H. As seen in FIG. 15H, each set of arms includes one long arm 710 and two short arms 704, all pivotably interconnected by two pins 714 and pivotably secured to the end pieces 702 and 708 by two pins 706. With this arrangement, each long arm 710 connects two coplanar short arms 704 generally situated 120 degrees apart from each other. In other embodiments (not shown), each set of arms may include two long arms 710 instead of one, and/or four short arms 704 instead of two (two short arms 704 located at each end of the long arm(s) 710). Also, in other embodiments, one, two, four, or more sets of arms may be used instead of three.

Gripper 700 is movable between a retracted state in which short arms 704 are substantially aligned with the longitudinal axis of gripper 700 (as shown in FIGS. 15A, 15C and 15E) and a deployed state in which short arms 704 are pivoted radially outward (as shown in FIGS. 15B, 15D and 15F). Gripper 700 may be moved from the retracted state to the deployed state by axially compressing end pieces 702 and 708 towards one another, such as with an actuator as previously described. Gripper 700 may be returned from the deployed state to the retracted state by applying an axially tensile force to end pieces 702 and 708. In the deployed state, the pointed distal ends of short arms 704 engage the inner surface of the bone (not shown). The arrangement of gripper 700 distributes the radial pressure of the gripping arms over six points of contact with the bone, as best seen in FIG. 15F. Three lines of contact are formed, spaced at every 120 degrees.

It should be noted here that each long arm 710 of gripper 700 is oriented at an angle with respect to the longitudinal axis of the gripper when in the retracted position. This angle increases as gripper 700 is moved into the deployed position. This arrangement provides the advantage of high expansion forces at low expansion angles, similar to the grippers of FIGS. 12A-12G and 13A-13H described above. It should also be noted that each long arm 710 has an inward surface that is flat and an outward surface that is contoured to match the cylindrical projection of end pieces 702 and 708 when gripper 700 is in the retracted state. This allows gripper 700 to be easily introduced into a bone. The particular arrangement of gripper 700 also advantageously centers itself and an attached fixation device inside an intramedullary space when being deployed.

Various descriptive terms such as "long arm" and "short arm" have been used in the above discussions to aid the reader in understanding the embodiments of the present invention. It should be noted that these terms are not meant to be limiting, as in some embodiments a "long arm" may be constructed to be longer, shorter, or of equal length as the "short arm". Similarly, all of the components described as either "long arms" or "short arms" in any particular embodiment do not necessarily need to be the same length.

Referring to FIGS. 16A-16D, a tubular gripper embodiment is shown. Gripper 800 is generally tube-shaped and has a series of slots 802 formed through its wall thickness along the length and around the circumference of the tube. In this embodiment, each slot 802 is helical, as shown. In other embodiments, the slots may be straight or form other patterns. Slots 802 may be formed by laser cutting, punching, milling, etching, sawing, electro-discharge machining, or otherwise removing material from the body of the gripper. Slots 802 may also be created by molding, extruding or otherwise forming the beam members 804 between the slots 802. Gripper 800 may be formed from metal, composite, plastic, amorphous materials, shape memory alloy, and/or other suitable materials.

Figure 16A:
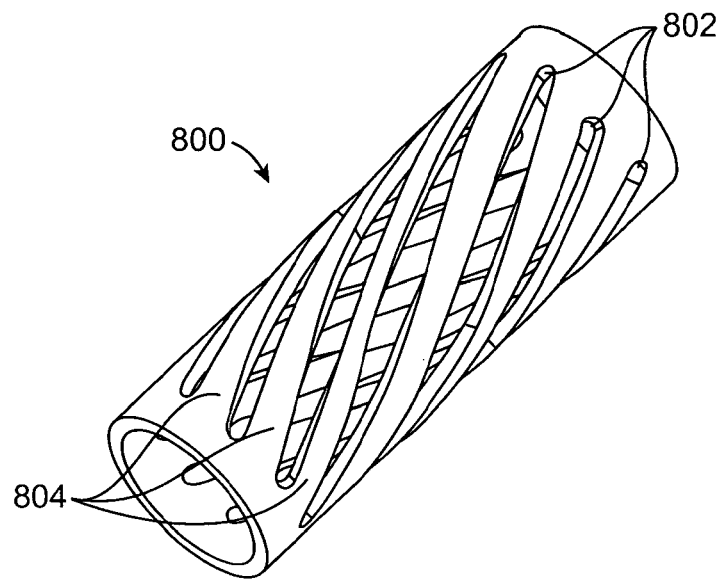
FIG. 16A is a perspective view showing another alternative gripper design in a retracted or undeployed state.
Figure 16B:
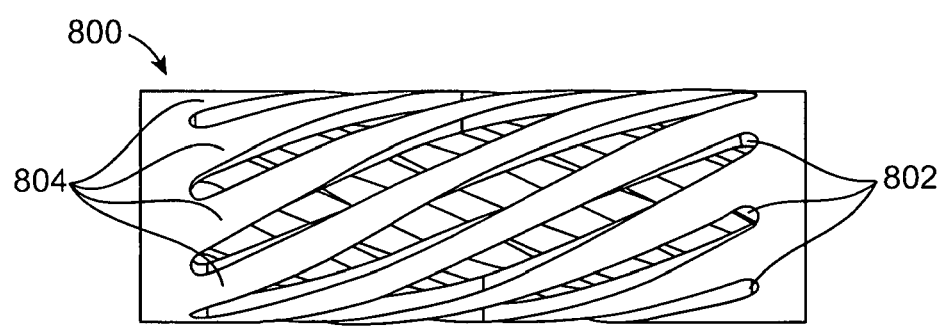
FIG. 16B is a side elevational view showing the gripper of FIG. 16A in a retracted or undeployed state.
Figure 16C:
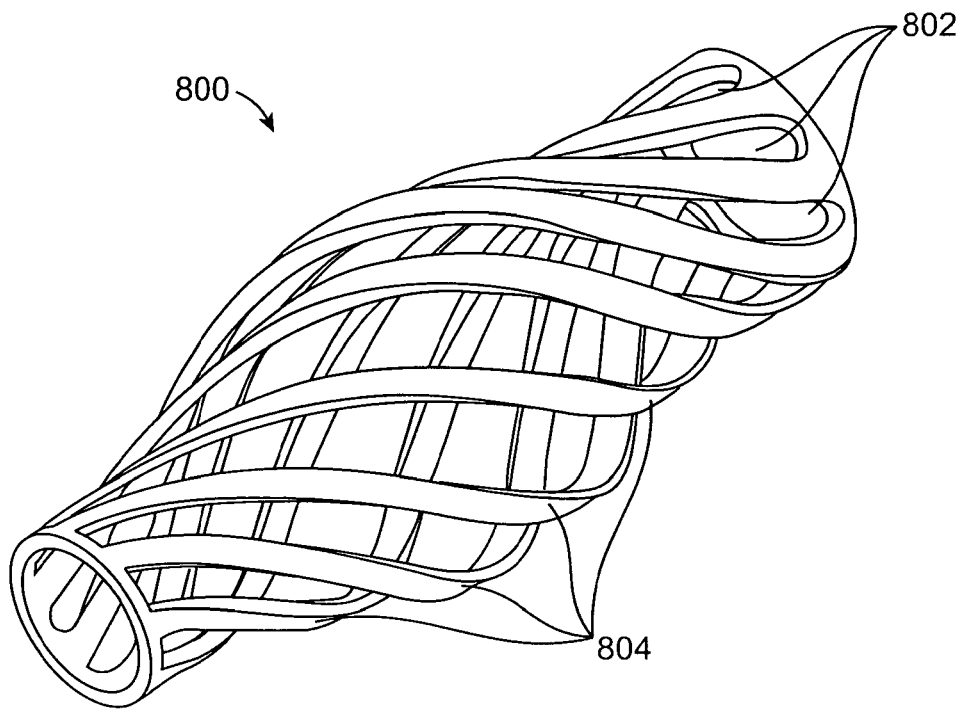
FIG. 16C is a perspective view showing the gripper of FIG. 16A in a deployed state.
Figure 16D:
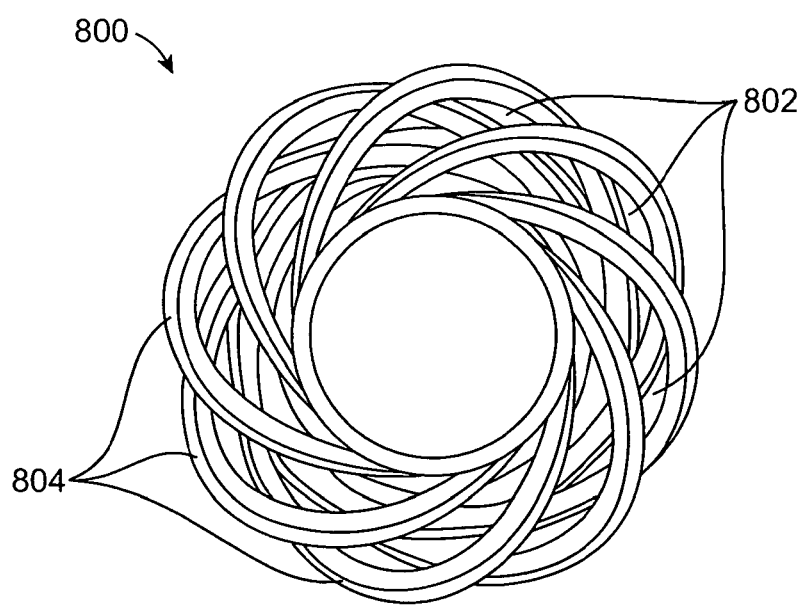
FIG. 16D is an end view showing the gripper of FIG. 16A in a deployed state.

FIGS. 16A and 16B show gripper 800 in a retracted state. By applying a compressive axial load to the ends of gripper 800 as with the previously described grippers, gripper 800 expands radially outward into a deployed state, as shown in FIGS. 16C and 16D. In the deployed state, mid-portions of beam members 804 arc outwardly to contact an inner surface of bone to anchor an attached fixation device to the bone. By applying a tensile force to the ends of gripper 800, it may be at least partially returned to the retracted state. In some embodiments of the invention, beam members 804 undergo only elastic deformation when moving into the deployed state. In other embodiments, members 804 may undergo plastic deformation.

In some embodiments, a bone fixation device incorporating gripper(s) 800 may rotationally constrain the ends of the gripper relative to one another as the ends move axially. In other embodiments, the ends may be left unconstrained. In still other embodiments, the ends of gripper 800 may be biased or forced to rotate relative to one another as they move axially closer and/or farther apart. Such arrangements may advantageously increase or decrease the amount of expansion that occurs when the gripper is axially compressed, and/or may similarly alter the amount of retraction that occurs when the gripper is axially pulled under tension.

Figure 17A:
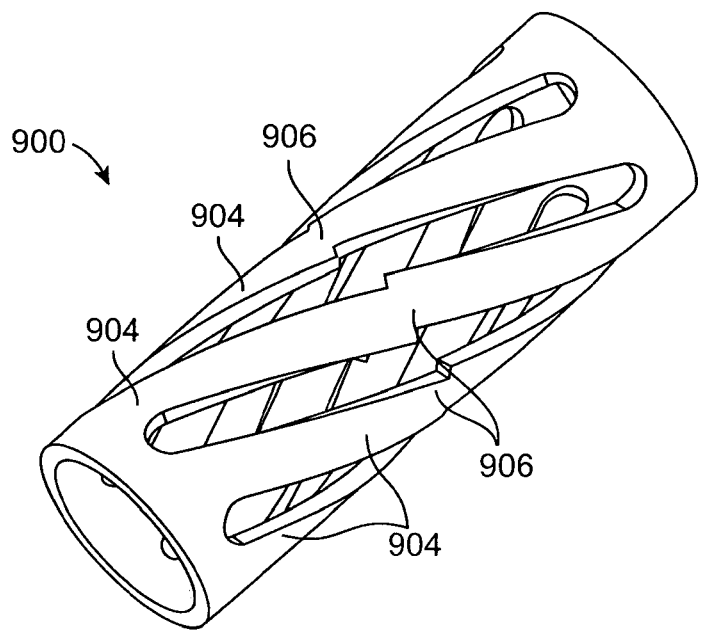
FIG. 17A is a perspective view showing another alternative gripper design in a retracted or undeployed state.
Figure 17B:
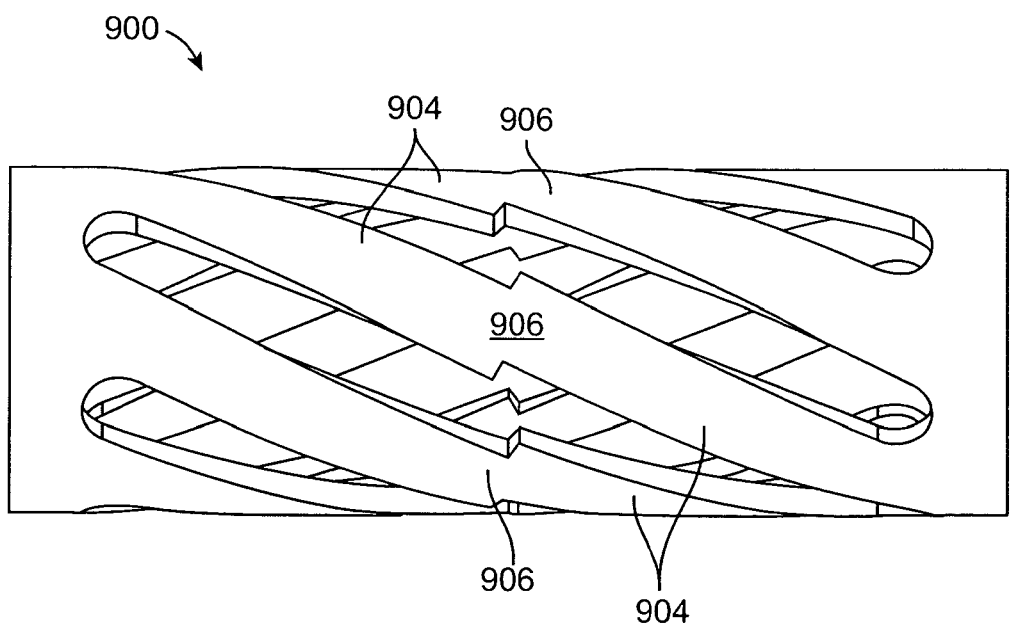
FIG. 17B is a side elevational view showing the gripper of FIG. 17A in a retracted or undeployed state.

FIGS. 17A and 17B show another tubular gripper embodiment. Gripper 900 is similar to gripper 800, but beam members 904 each have an offset portion 906 located at their mid-portions. These offset portions 906 create a pair of sharp points on opposite sides of each beam member that can enhance the gripping effectiveness of gripper 900 by engaging with the interior bone surface when the gripper is deployed.

Figure 18A:
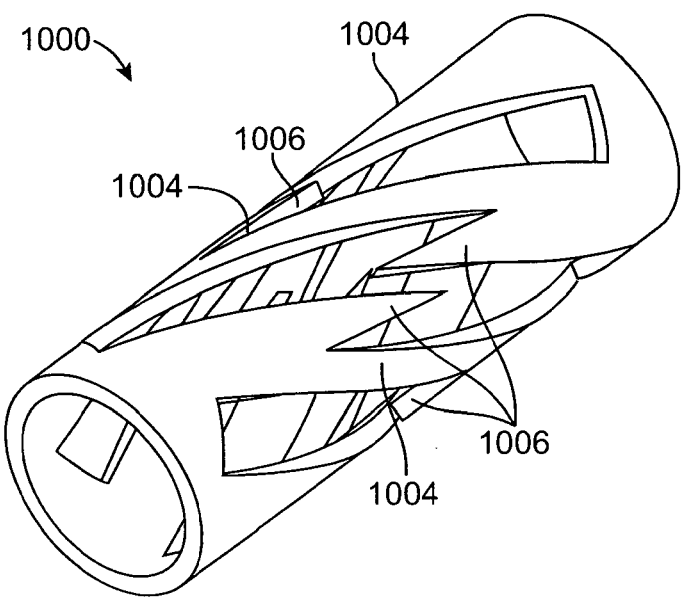
FIG. 18A is a perspective view showing another alternative gripper design in a retracted or undeployed state.
Figure 18B:
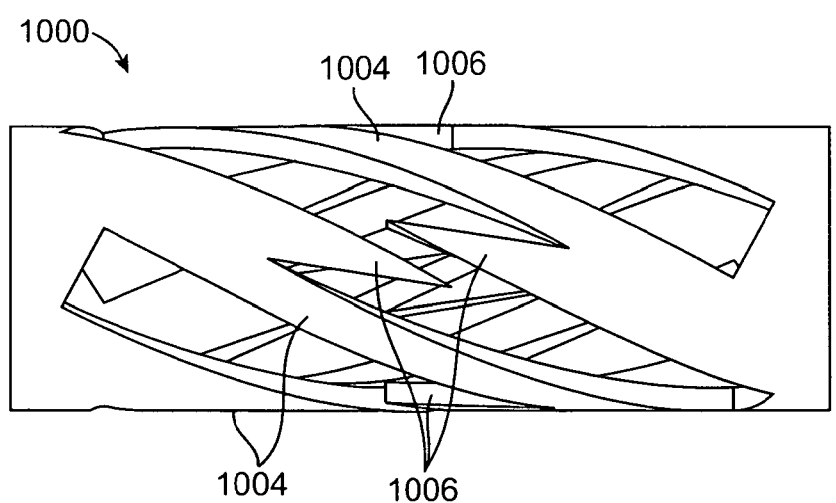
FIG. 18B is a side elevational view showing the gripper of FIG. 18A in a retracted or undeployed state.

FIGS. 18A and 18B show another tubular gripper embodiment. Gripper 1000 is similar to both grippers 800 and 900. Gripper 1000 includes a protruding member 1006 located along each side of each beam member 1004. Pointed ends of opposite facing protruding members 1006 provide additional gripping engagement when gripper 1000 is deployed.

Figure 19A:
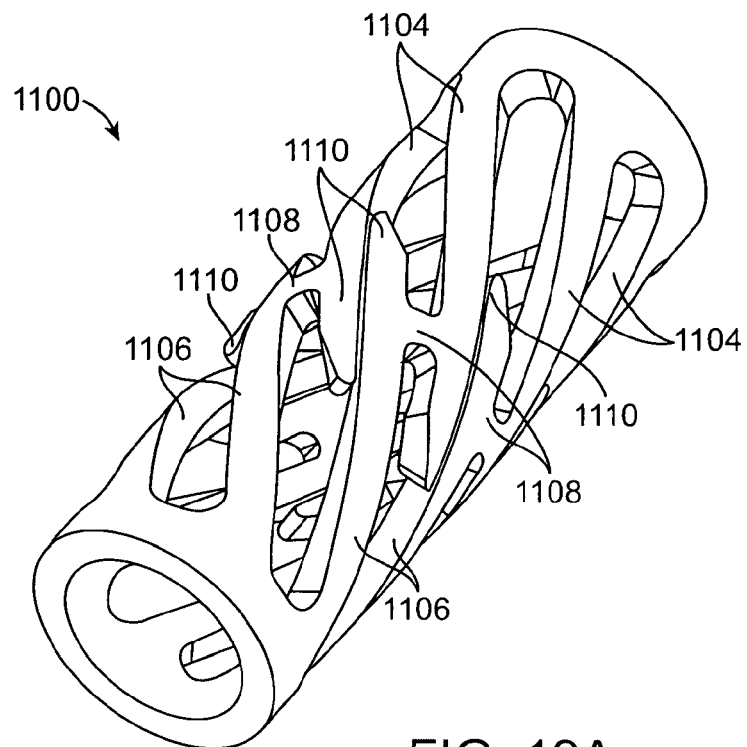
FIG. 19A is a perspective view showing another alternative gripper design in a retracted or undeployed state.
Figure 19B:
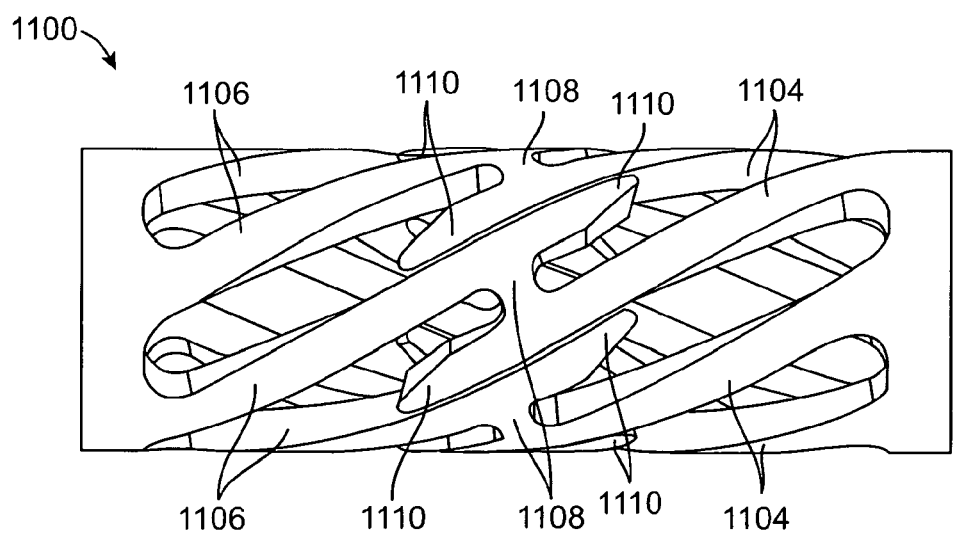
FIG. 19B is a side elevational view showing the gripper of FIG. 19A in a retracted or undeployed state.

FIGS. 19A and 19B show another tubular gripper embodiment. Gripper 1100 includes a first series of beam members 1104 helically extending from a first end of the gripper, and a second series of opposing beam members 1106 helically extending from the opposite end of the gripper and which interdigitate with the first series 1104. The first series of beam members 1104 are interconnected with the second series 1106 by a series of short leaf springs 1108 around the mid-circumference of gripper 1100. As gripper 1100 axially compresses and beam members 1104 and 1106 bend toward a deployed state, the distal ends 1110 of members 1104 and 1106 engage with the interior surface of the bone.

Figure 20A:
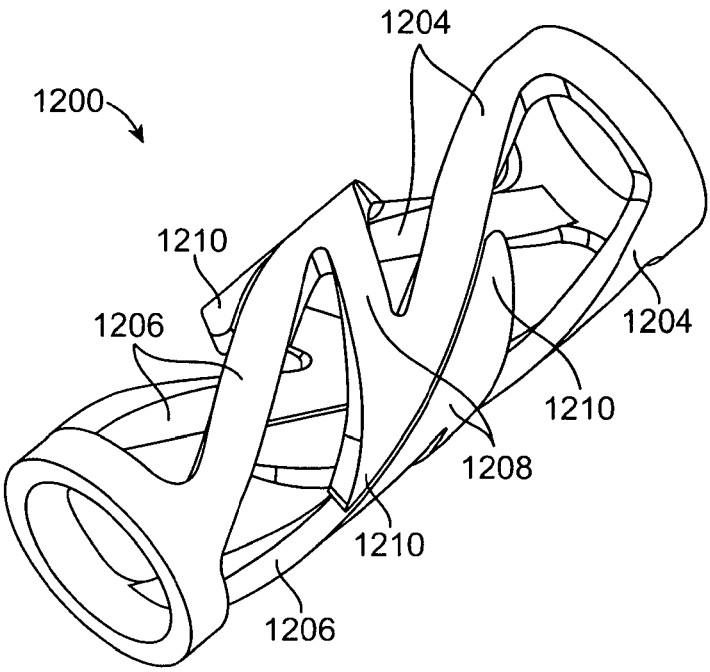
FIG. 20A is a perspective view showing another alternative gripper design in a retracted or undeployed state.
Figure 20B:
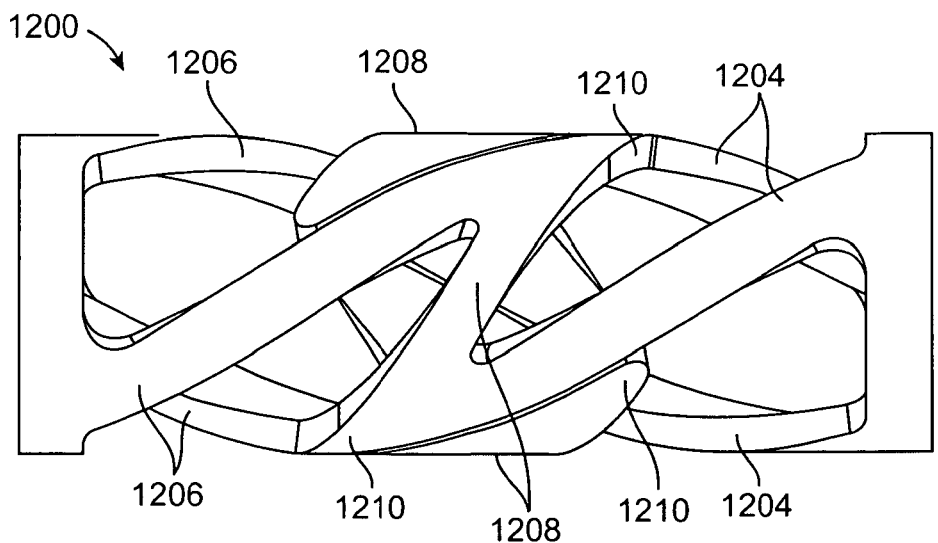
FIG. 20B is a side elevational view showing the gripper of FIG. 20A in a retracted or undeployed state.

FIGS. 20A and 20B show another tubular gripper embodiment. Gripper 1200 of this embodiment is similar to gripper 1100 of the previous embodiment, but fewer beam members 1204 and 1206 are employed in gripper 1200, and the beam members 1204 and 1206 are interconnected with longer, Z-shaped leaf springs 1208. As gripper 1200 axially compresses and beam members 1204 and 1206 bend toward a deployed state, the distal ends 1210 of members 1204 and 1206 engage with the interior surface of the bone.

Figure 21A:
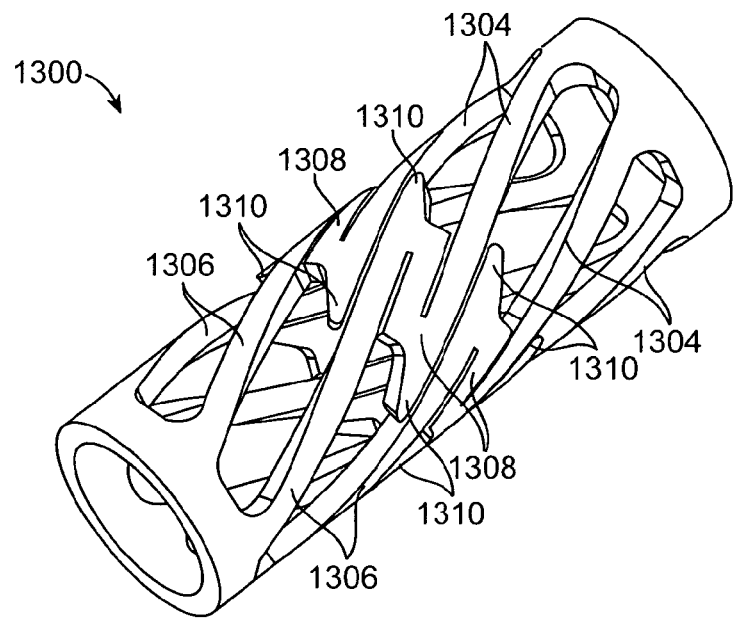
FIG. 21A is a perspective view showing another alternative gripper design in a retracted or undeployed state.
Figure 21B:
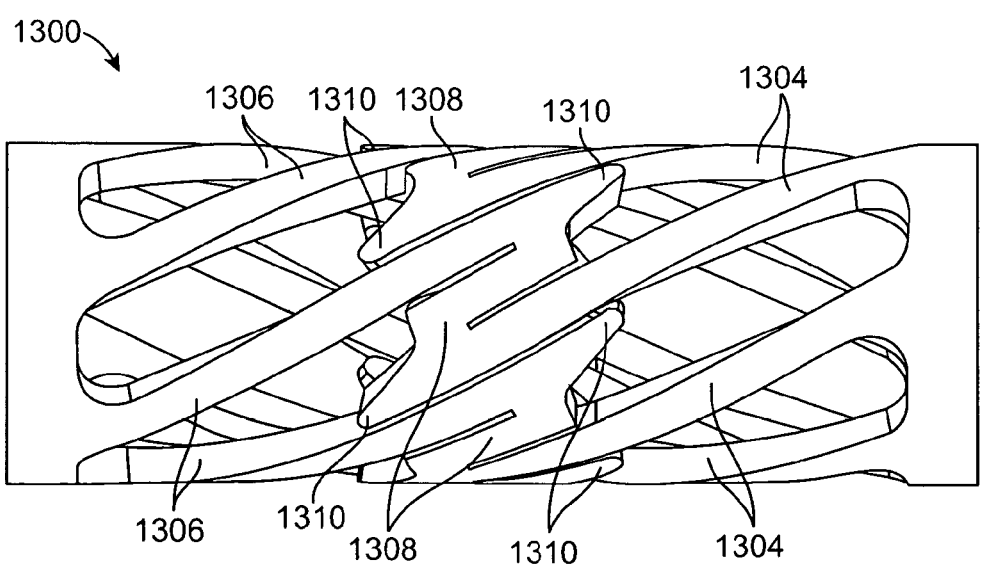
FIG. 21B is a side elevational view showing the gripper of FIG. 21A in a retracted or undeployed state.

FIGS. 21A and 21B show another tubular gripper embodiment. Gripper 1300 of this embodiment is also similar to gripper 1100 shown in FIGS. 19A and 19B, but the beam members 1304 and 1306 are interconnected with serpentine leaf springs 1308. As gripper 1300 axially compresses and beam members 1304 and 1306 bend toward a deployed state, the distal ends 1310 of members 1304 and 1306 engage with the interior surface of the bone.

In any of the above-described tubular gripper embodiments, a thinned down portion (not shown) may be provided at a predetermined location or locations along one or more of the beam members to cause the beam member to bend at that particular location during deployment under axial compressive loading.

Figure 22A:
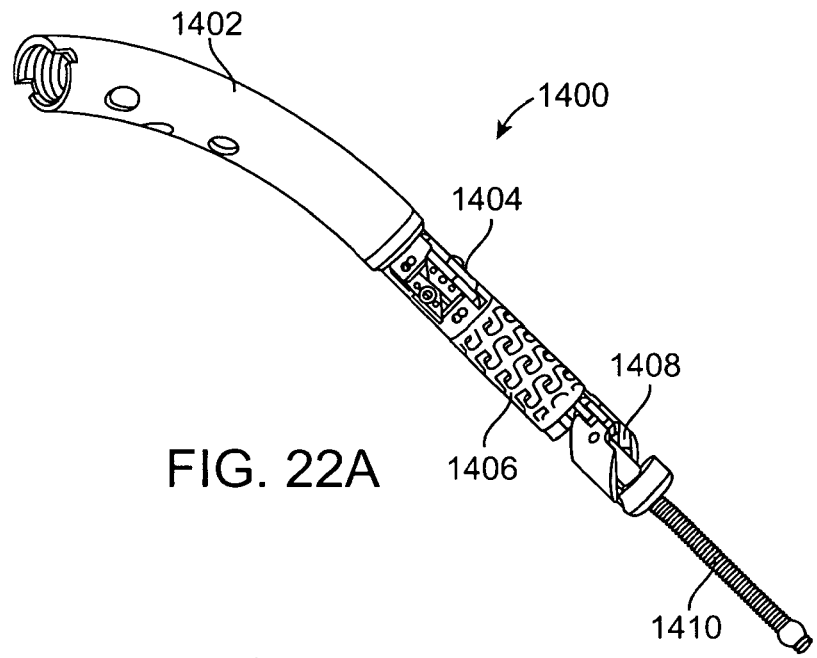
FIG. 22A is a perspective view showing another bone fixation device in a retracted or undeployed state.
Figure 22B:
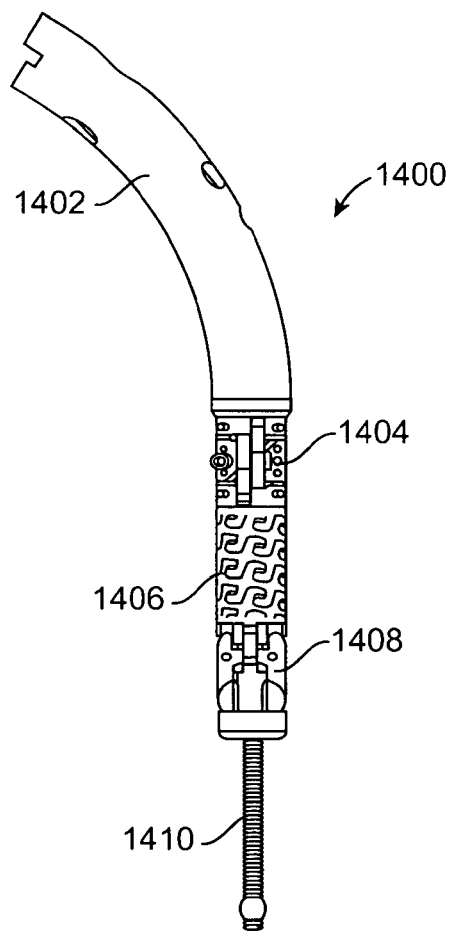
FIG. 22B is a top plan view showing the device of FIG. 22A in a retracted or undeployed state.
Figure 22D:
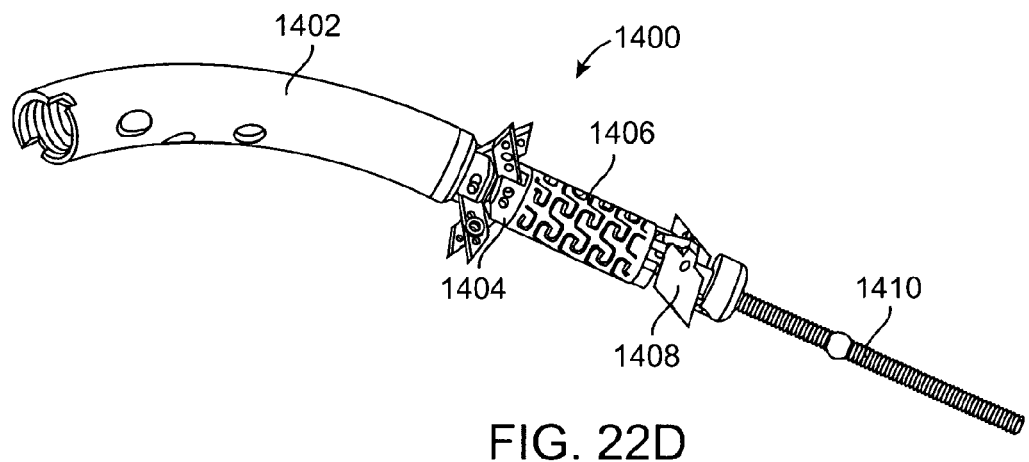
FIG. 22D is a perspective view showing the device of FIG. 22A in a deployed state.
Figure 22C:
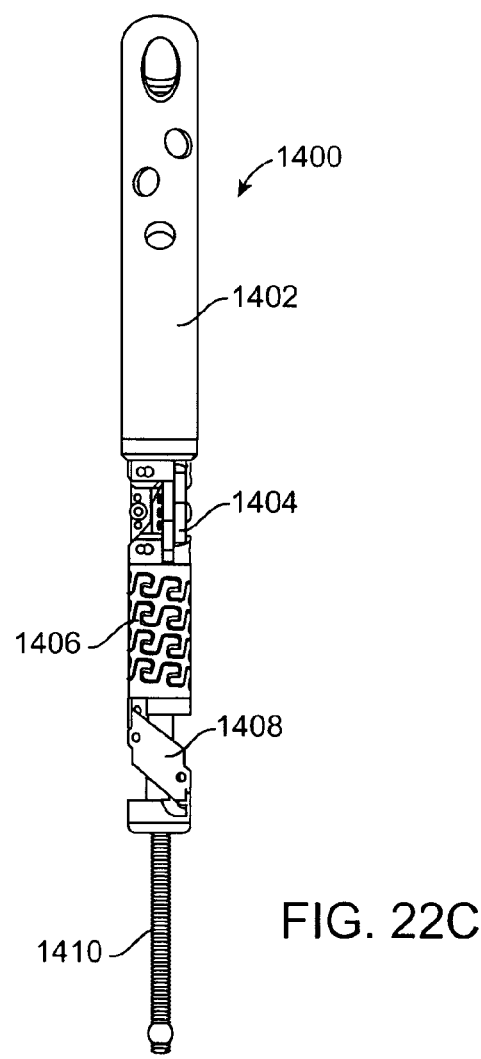
FIG. 22C is a side elevational view showing the device of FIG. 22A in a retracted or undeployed state.
Figure 22E:
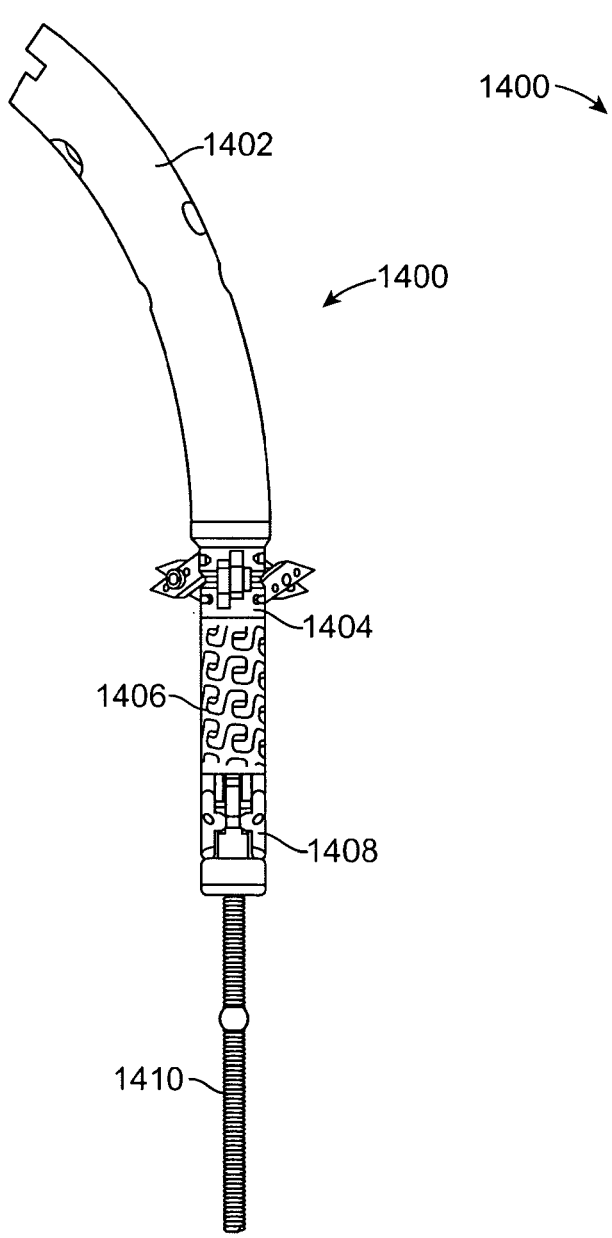
FIG. 22E is a top plan view showing the device of FIG. 22A in a deployed state.
Figure 22F:
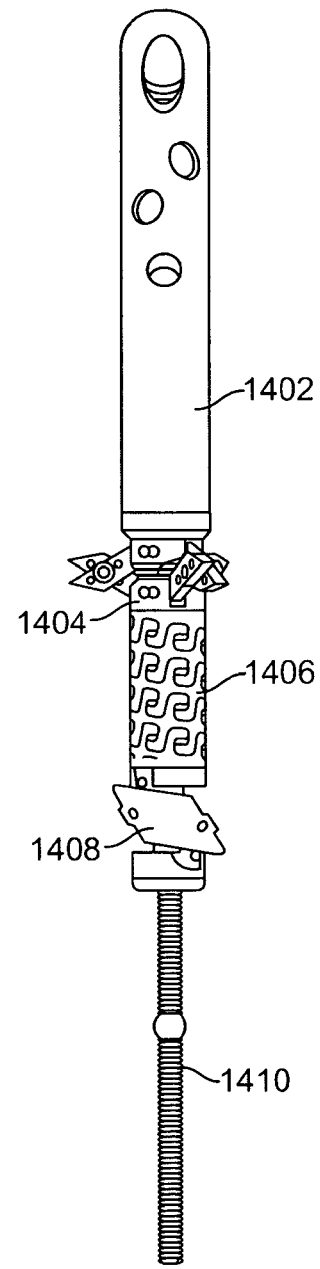
FIG. 22F is a side elevational view showing the device of FIG. 22A in a deployed state.

FIGS. 22A-22F show another exemplary embodiment of a bone fixation device 1400 constructed according to aspects of the present invention. Device 1400 includes a curved hub 1402, a proximal gripper 1404, a flexible-to-rigid body portion 1406, a distal gripper 1408, and an actuation lead screw 1410. FIGS. 22A-22C show device 1400 in an undeployed state, while FIGS. 22D-22F show device 1400 in a deployed state.

Figure 23A:
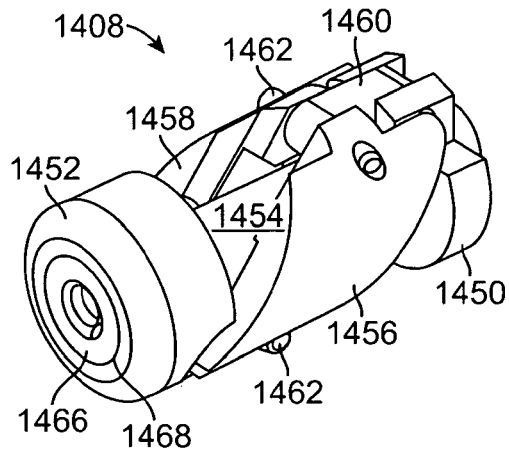
FIG. 23A is an enlarged perspective view showing just the distal gripper of the device of FIG. 22A in a retracted or undeployed state.
Figure 23B:
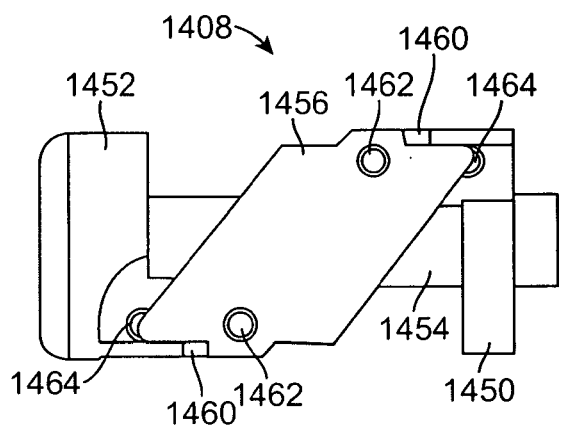
FIG. 23B is a side elevational view showing the gripper of FIG. 23A in a retracted or undeployed state.
Figure 23C:
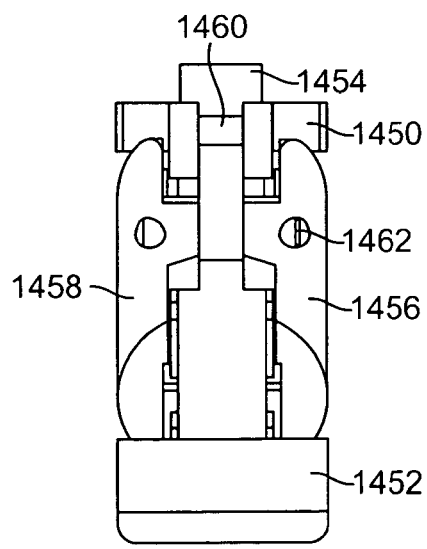
FIG. 23C is a top plan view showing the gripper of FIG. 23A in a retracted or undeployed state.
Figure 23D:
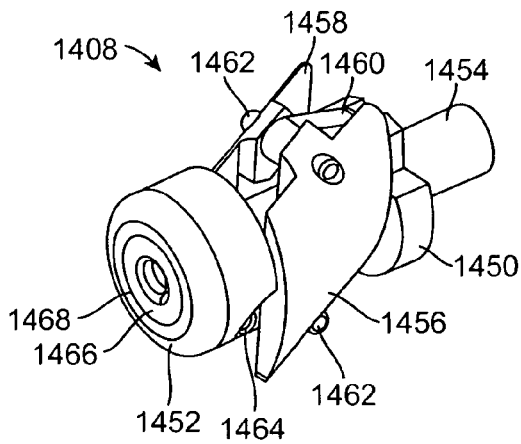
FIG. 23D is a perspective view showing the gripper of FIG. 23A in a deployed state.
Figure 23E:
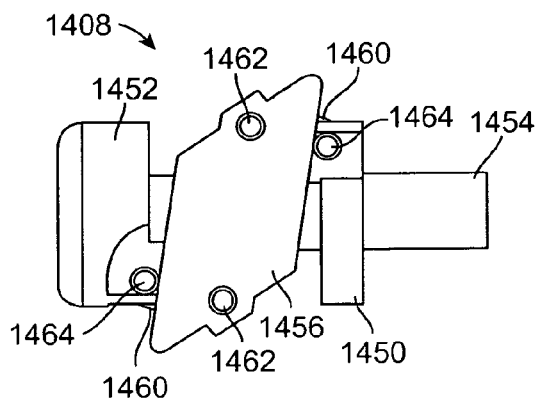
FIG. 23E is a side elevational view showing the gripper of FIG. 23A in a deployed state.
Figure 23F:
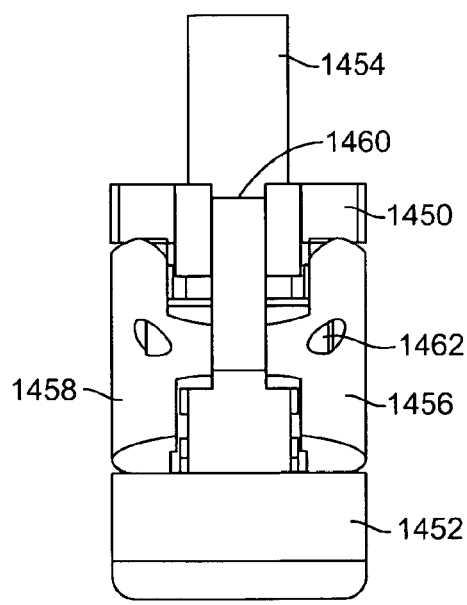
FIG. 23F is a top plan view showing the gripper of FIG. 23A in a deployed state.
Figure 23G:
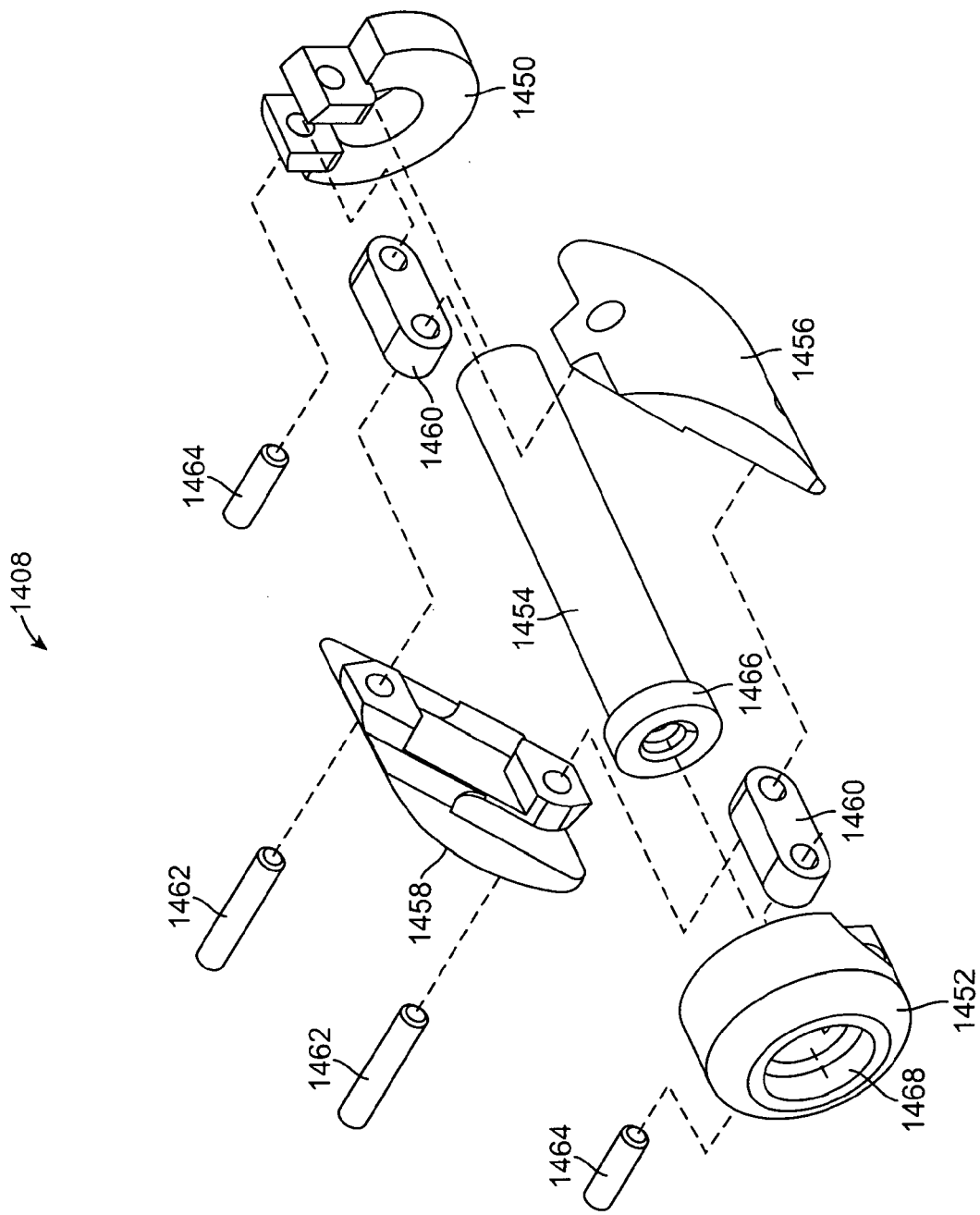
FIG. 23G is an exploded perspective view showing the gripper of FIG. 23A.

FIGS. 23A-23G show further details of distal gripper 1408 of device 1400 described above. As best seen in FIG. 23G, distal gripper 1408 comprises a proximal end piece 1450, a distal end piece 1452, a tubular core 1454, a first gripper arm 1456, a second gripper arm 1458, two link bars 1460, 1460, two long pins 1462, 1462, and two short pins 1464, 1464.

Tubular core 1454 may include a flange 1466 at its distal end as shown for engaging in a circular bore 1468 in the distal side of distal end piece 1452 for transferring axial loads. Tubular core 1454 may be fastened to distal end piece 1452, such as by a press fit and/or welding. Proximal end piece 1450 includes a central opening for receiving the tubular core 1454 such that proximal end piece may freely slide along the tubular core 1454.

Upper portions of both first and second gripper arms 1456, 1458 are pivotably connected to proximal link bar 1460 by a single long pin 1462. Proximal link bar 1460 in turn is pivotably connected to proximal end piece 1450 by a short pin 1464. Similarly, lower portions of both first and second gripper arms 1456, 1458 are pivotably connected to distal link bar 1460 by the other long pin 1462. Distal link bar 1460 in turn is pivotably connected to distal end piece 1452 by the other short pin 1464.

At least a portion of tubular core 1454 may be internally threaded for engaging actuation lead screw 1410 (shown in FIGS. 22A-22F). As actuation lead screw 1410 is turned in an actuation or deployment direction, tubular core 1454 and attached distal end piece 1452 is drawn in a proximal direction. Since proximal end piece 1450 is prevented from also moving in the proximal direction by flexible-to-rigid body portion 1406 (shown in FIGS. 22A-22F), tubular core 1454 telescopes through proximal end piece 1450 into the central bore of flexible-to-rigid body portion 1406. In other words, when gripper 1408 is deployed, its distal and proximal end pieces 1452, 1450 are moved toward each other, with proximal end piece 1450 sliding along the outside surface of tubular core 1454. As this occurs, first and second gripper arms 1456, 1458 are forced to rotate from a retracted, undeployed position, as shown in FIGS. 23A-23C, toward an extended, deployed position, as shown in FIGS. 23D-23F. In the deployed position, the outward tips of gripper arms 1456, 1458 engage with bone tissue within the intramedullary space of the bone to secure gripper 1408 and device 1400 within the bone.

If desired, gripper 1408 may be moved back to the retracted, undeployed state by turning actuation lead screw 1410 (shown in FIGS. 22A-22F) in an opposite direction, causing tubular core 1454 and attached distal end piece 1452 to move in a distal direction, such that tubular core 1454 recedes from within flexible-to-rigid body portion 1406, distal and proximal end pieces 1452, 1450 separate, and gripper arms 1456, 1458 rotate back to the retracted position shown in FIGS. 23A-23C.

According to aspects of the present invention, in some embodiments the tubular core 1454 serves to isolate the threads of the actuation lead screw 1410 from corners and other geometry that could potentially damage the screw. This can improve reliability of the device and reduce or eliminate the chance of particulate matter being dislodged from the device and migrating into the patient. Tubular core 1454 may also serve to protect actuation lead screw 1410 from bending moments generated by the gripper during deployment. This in turn makes the device more robust and enables the screw to provide higher torque and higher tension performance.

Figure 24:
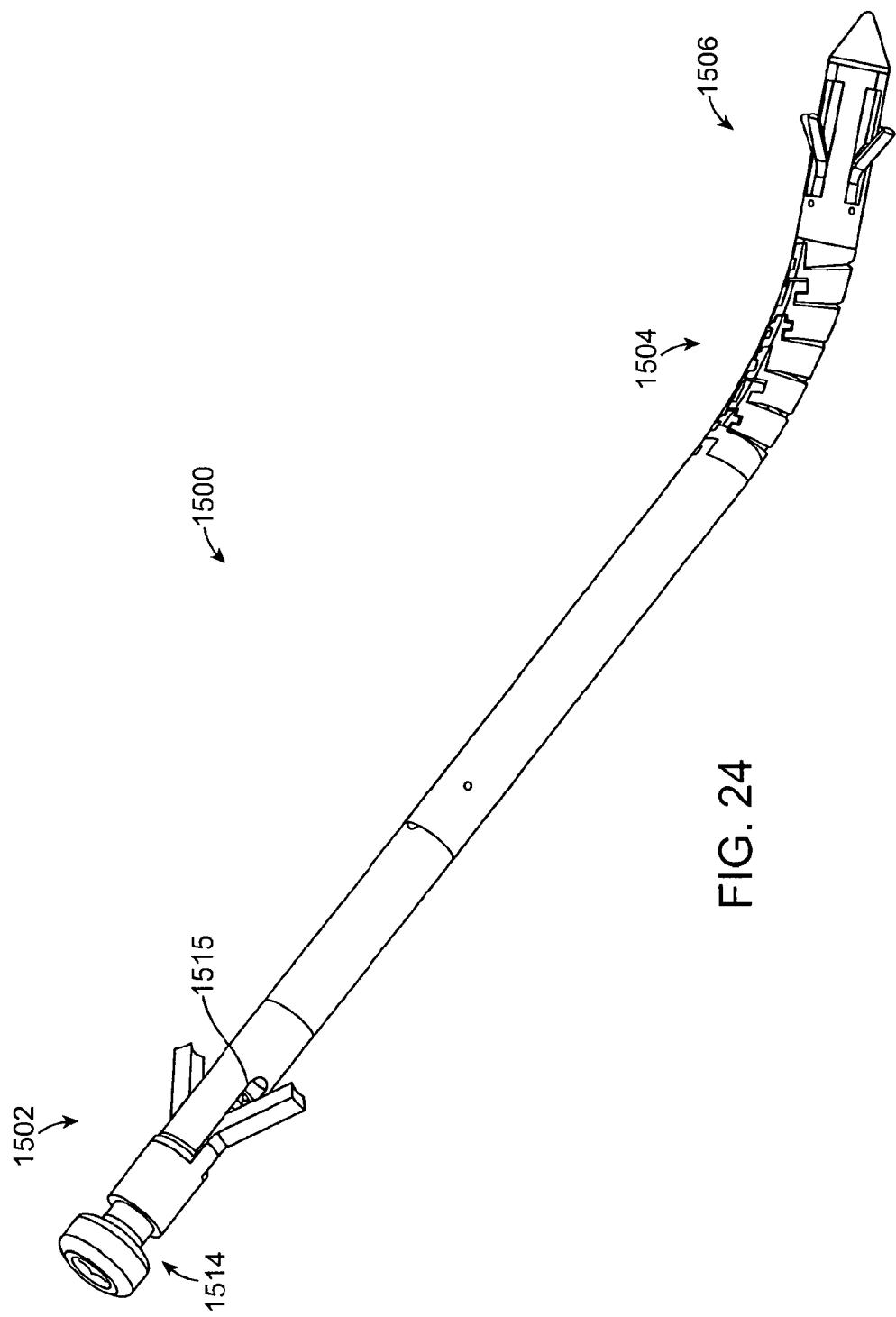
FIGS. 24-26 are various views showing another embodiment of a bone fixation device.
Figure 25:
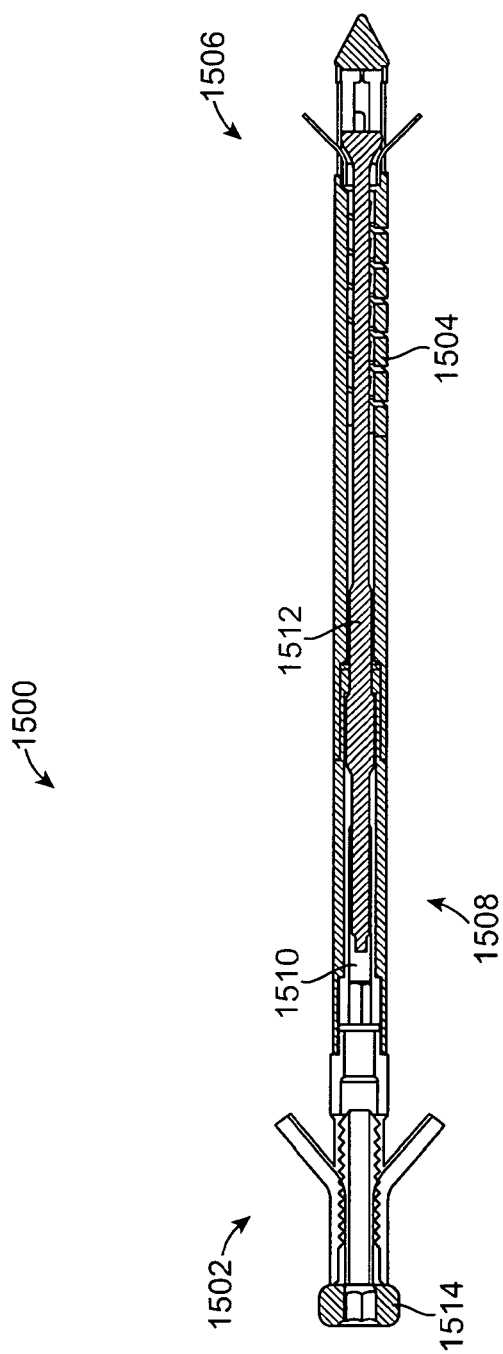
Figure 26:
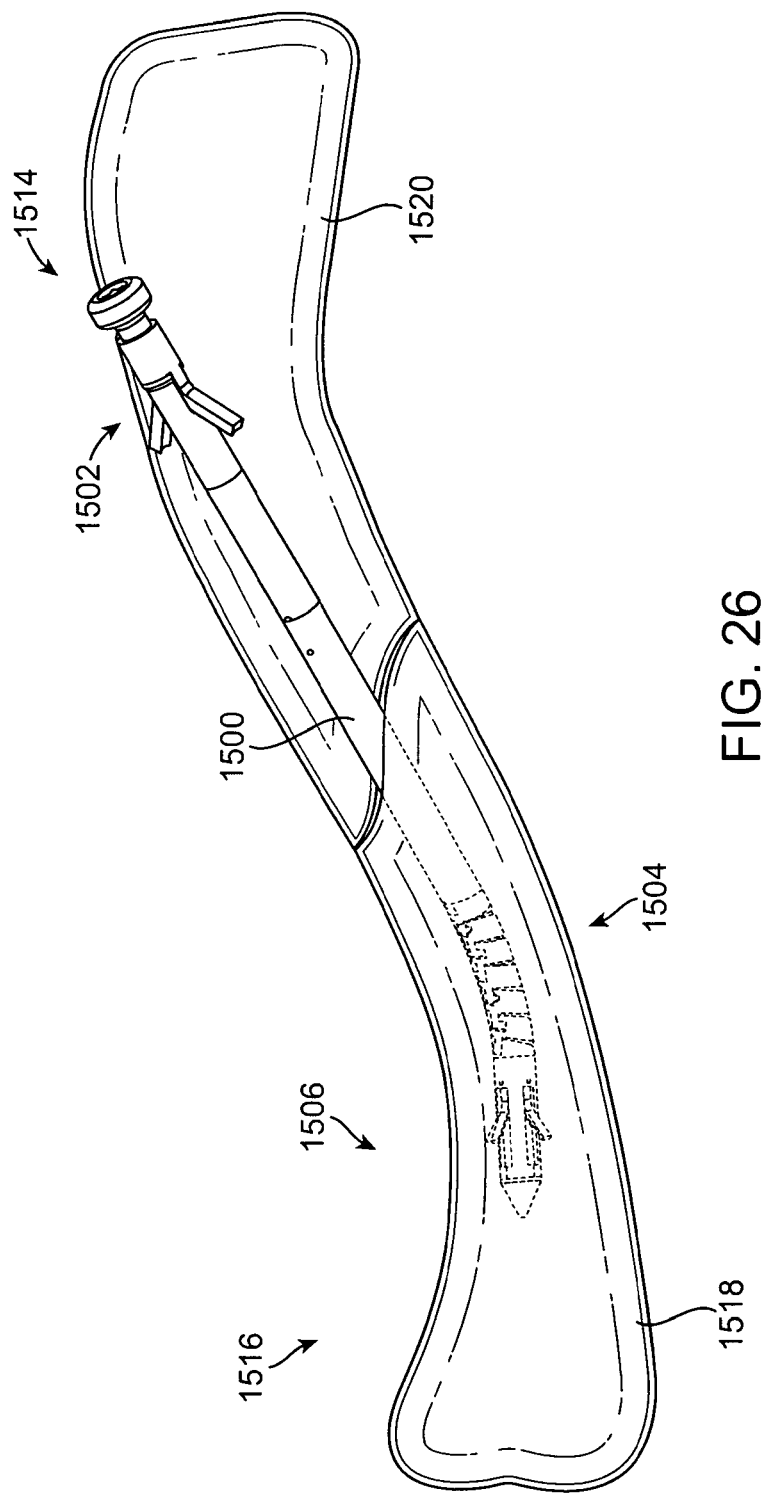

Referring to FIGS. 24-26, another embodiment of a bone fixation device is shown. Device 1500 is similar in construction and operation to the previously described bone fixation devices. Device 1500 includes a proximal gripper 1502, flexible-to-rigid body portion 1504, and distal gripper 1506. As can been seen in the figures, flexible-to-rigid portion 1504 of the elongate body of device 1500 is disposed at a location on the elongate body distal to a first gripper 1502 and proximal to a second gripper 1506.

As best seen in FIG. 25, device 1500 includes two separate actuators. The first actuator 1508 in located internally within device 1500 and operates in similar fashion to the actuators of devices previously described herein. First actuator 1508 includes an internally threaded tube 1510 that is driven by a keyed feature at its proximal end. Tube 1510 is coupled to externally threaded rod 1512. When tube 1510 is rotated, rod 1512 is drawn in a proximal direction. Ramped surfaces at the distal end of rod 1512 cause bendable arms of distal gripper 1506 to be outwardly deployed.

The second actuator 1514 of device 1500 comprises an externally threaded compression screw having a central lumen. The compression screw is coupled to internal threads within proximal gripper 1502. In some embodiments, the compression screw outwardly deploys one, two, three, four or more bendable gripper arms by driving the gripper arms distally against ramped surface(s). In other embodiments, the gripper arm(s) do not move axially when deployed. Instead, the compression screw moved axially in a proximal direction. Because the compression screw has a larger diameter in these embodiments than the internal diameter of a portion the proximal gripper, movement of the compression screw urges the gripper arms in an outward direction. Slots 1515 may be provided in the proximal end of device 1500 to resist torque from proximal gripper 1502

In operation, device 1500, with grippers 1502 and 1506 in a retracted state, may be inserted into the intramedullary space within a bone, such as a clavicle bone 1516 as shown in FIG. 26. Once device 1500 is in place inside the bone, the first actuator 1508 may be actuated from the proximal end of device 1500 by inserting a drive tool through the central lumen of the compression screw of the second actuator 1514, engaging the distal end of the drive tool with the keyed end of tube 1510 and turning, in a manner similar to that previously described. Longitudinal movement of rod 1512 toward the proximal end of device 1500 causes flexible-to-rigid body portion 1504 to foreshorten and assume its rigid state, and causes distal gripper 1506 to outwardly deploy against the bone, such as the medial segment 1518 of the clavicle bone 1516 shown in FIG. 26. The drive tool is then removed, and a drive tool having a larger keyed end is inserted into the keyed end of the compression screw to turn the second actuator 1514, causing the bendable arms of proximal gripper 1502 to outwardly deploy against the bone, such as the lateral segment 1520 of the clavicle bone 1516.

Figure 27:
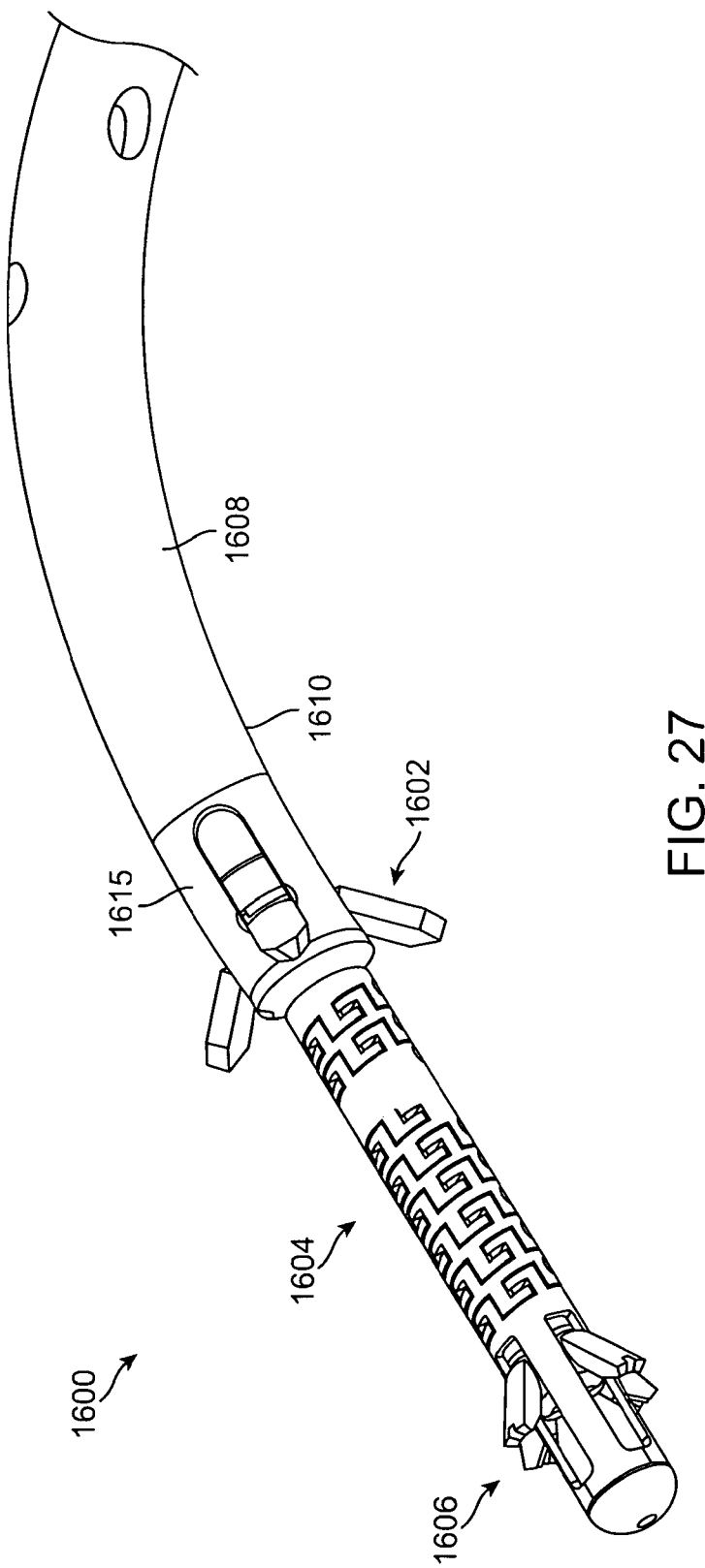
FIGS. 27-28 are views showing another embodiment of a bone fixation device.
Figure 28:
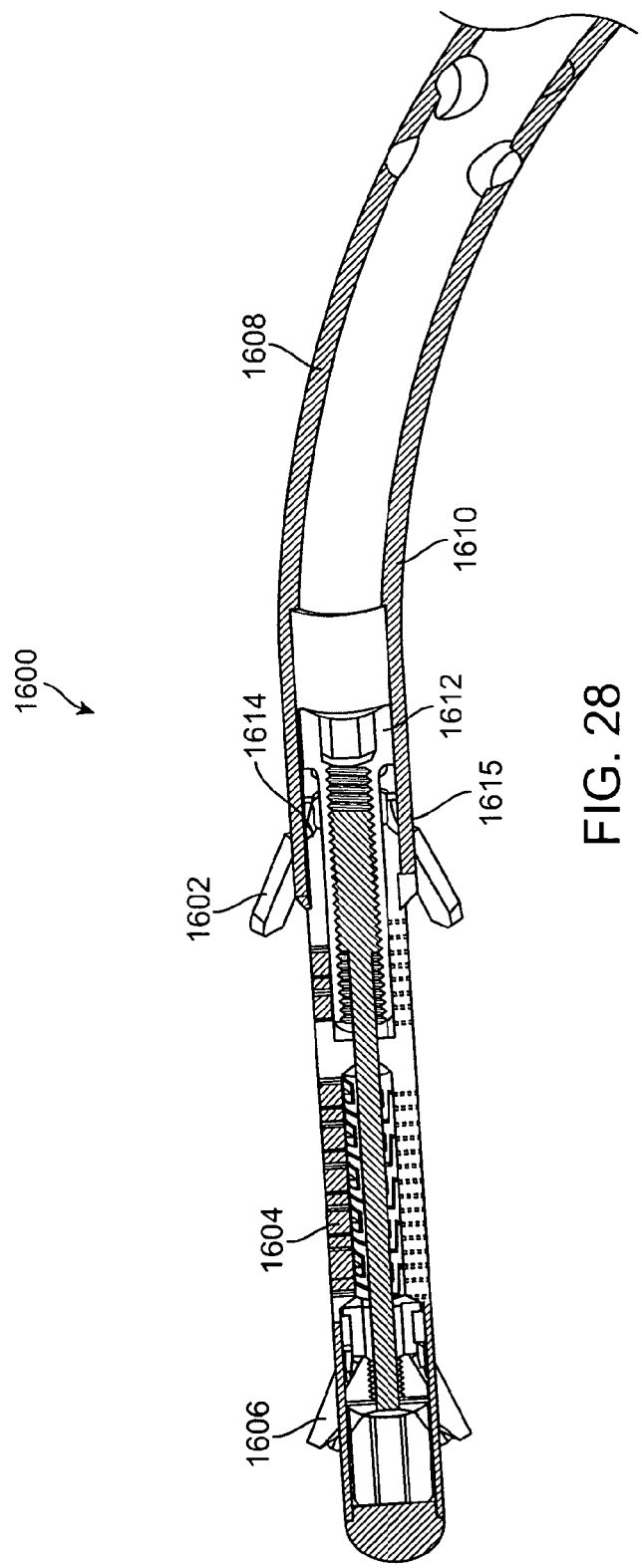
Figure 29:
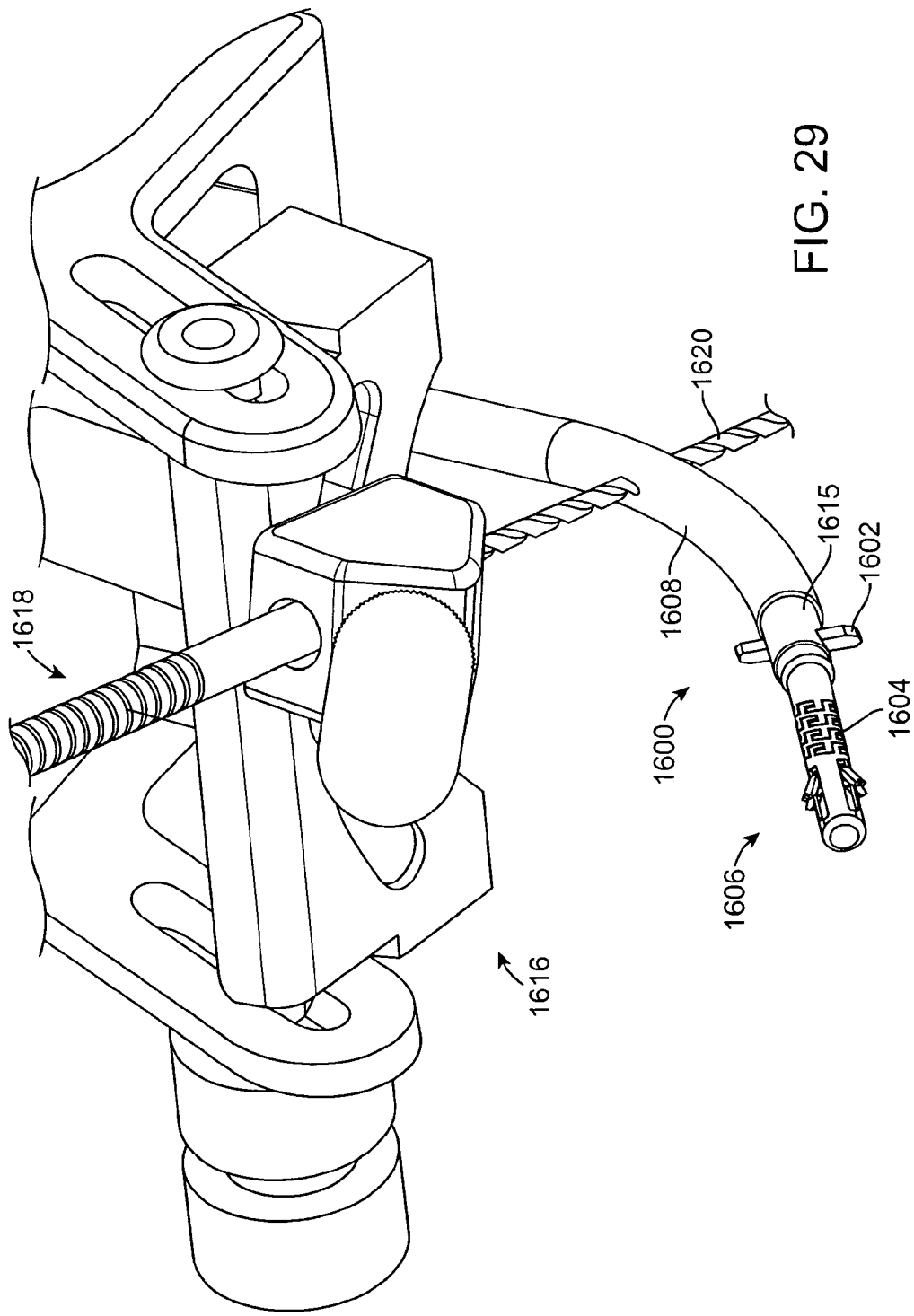
FIG. 29 is a perspective view showing the device of FIGS. 27-28 coupled with a screw hole forming guide tool.

Referring to FIGS. 27-29, another embodiment of a bone fixation device is shown. Device 1600 is similar in construction and operation to the previously described bone fixation devices. Device 1600 includes a proximal gripper 1602, flexible-to-rigid body portion 1604, and distal gripper 1606. As can been seen in the figures, flexible-to-rigid portion 1604 of the elongate body of device 1600 is disposed at a location on the elongate body distal to a first gripper 1602 and proximal to a second gripper 1606. In this embodiment, the bendable arms of proximal gripper 1602 are spaced 120 degrees apart around the axis of the device.

Device 1600 includes a curved hub 1608 having a straight section 1610 for holding inner actuation mechanism 1612. In this embodiment, the single actuation mechanism 1612 actuates both grippers 1602 and 1606. Flexible-to-rigid portion 1604 includes an interlocking cut pattern that prevents uncoiling of the body under tension. The body also has an anti-rotation feature built into it. A chamfer 1614 is provided at the proximal end of flexible-to-rigid portion 1604 to cause the bendable arms of proximal gripper 1602 to expand outwardly when body portion 1604 is driven proximally. The distal portion 1615 of curved hub 1608 may be tapered as shown to allow for easier implantation intraoperatively.

FIG. 29 illustrates how device 1600 may be used with an external fixture 1616 to allow screw holes to be formed in hub 1608 or flexible-to-rigid portion 1604 in vivo. In some embodiments, device 1600 is devoid of any preformed screw holes before it is installed in the bone. In some embodiments, hub 1608 is made from a biocompatible material such as PEEK to allow the screw holes to be easily formed in vivo. A depth gage 1618 may be provided on the screw forming tool 1620 to aid in screw hole formation.

Figure 30:
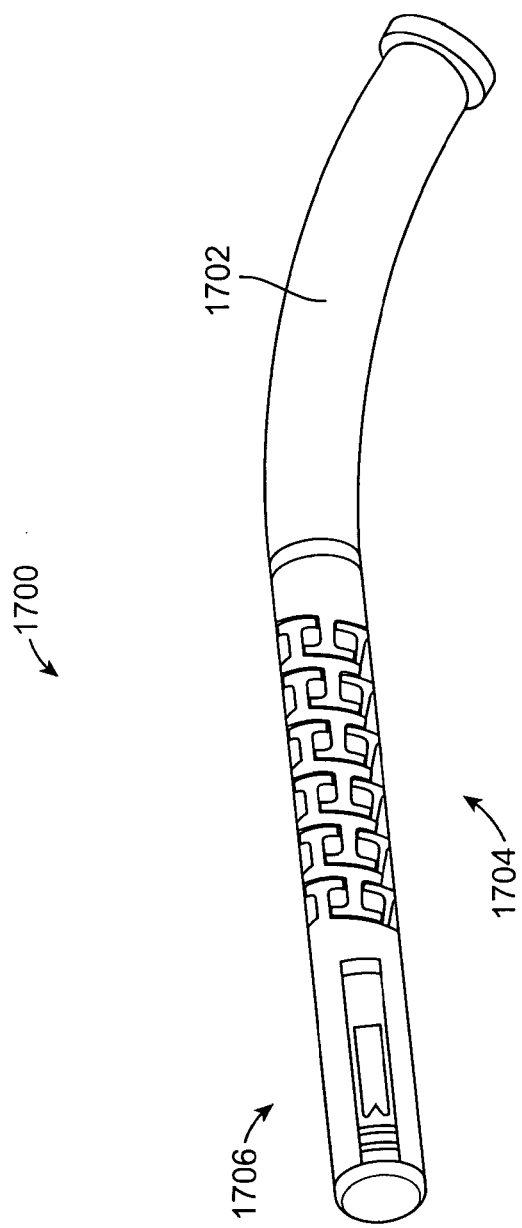
FIGS. 30-31 are various views showing another embodiment of a bone fixation device.
Figure 31:
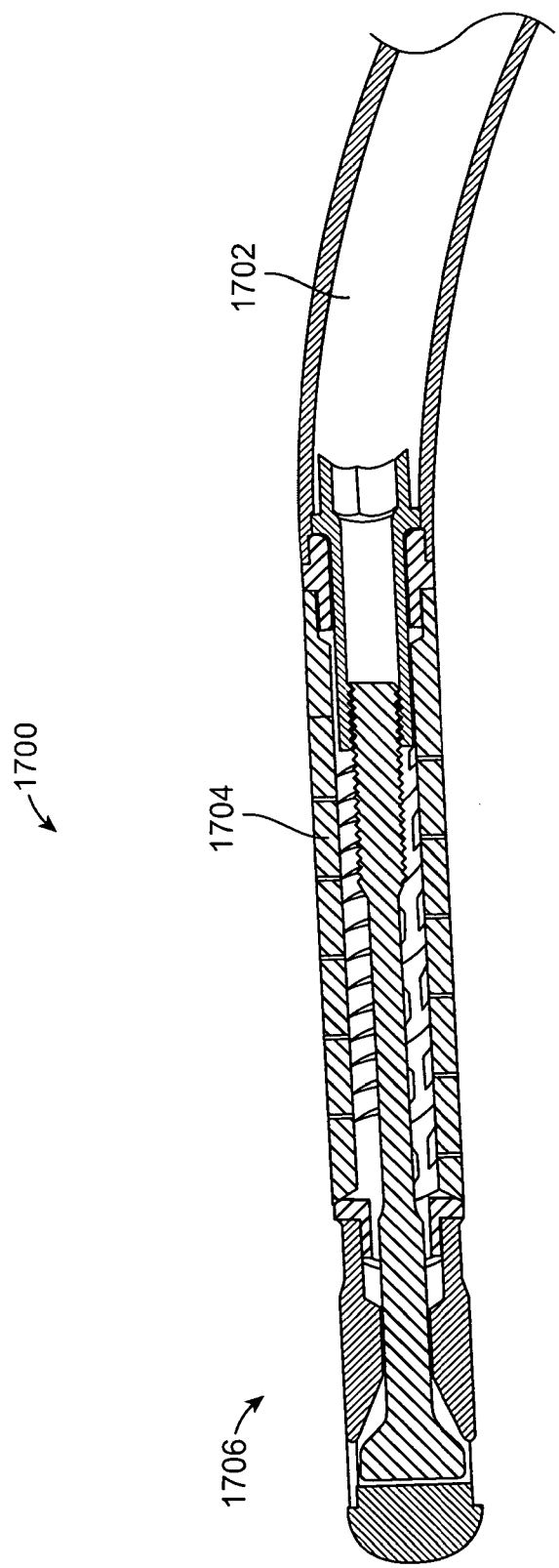
Figure 32:
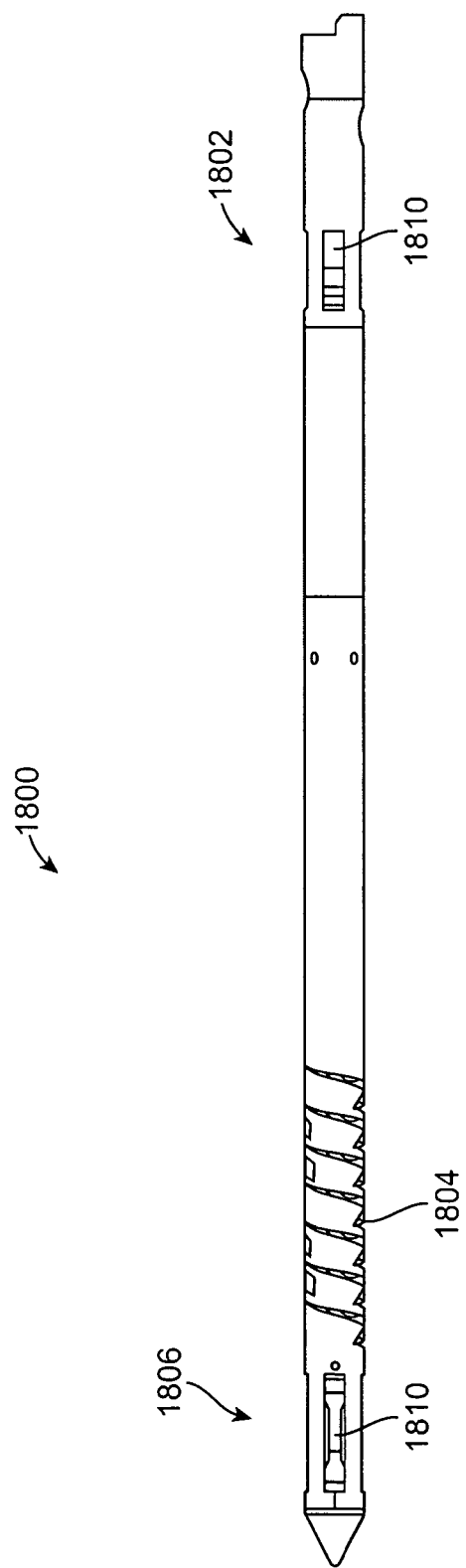
FIGS. 32-35 are various views showing another embodiment of a bone fixation device.

Referring to FIGS. 30-31, another embodiment of a bone fixation device is shown. Device 1700 is similar in construction and operation to the previously described bone fixation devices. Device 1700 includes a curved hub 1702 at its proximal end, a flexible-to-rigid body portion 1704, and a single gripper 1706 located at its distal end. As can been seen in the figures, the single actuatable bone engaging gripper 1706 is disposed on the elongate body at a location distal to the flexible-to-rigid portion 1704 of the elongate body of device 1700.

Referring to FIGS. 32-35, another embodiment of a bone fixation device is shown. Device 1800 is similar in construction and operation to the previously described bone fixation devices. Device 1800 includes a proximal gripper 1802, flexible-to-rigid body portion 1804, and distal gripper 1806. As can been seen in the figures, flexible-to-rigid portion 1804 of the elongate body of device 1800 is disposed at a location on the elongate body distal to a first gripper 1802 and proximal to a second gripper 1806. In this embodiment, each of the grippers 1802 and 1806 includes four fan-like bendable arms 1810 similar to those previously described.

Figure 33:
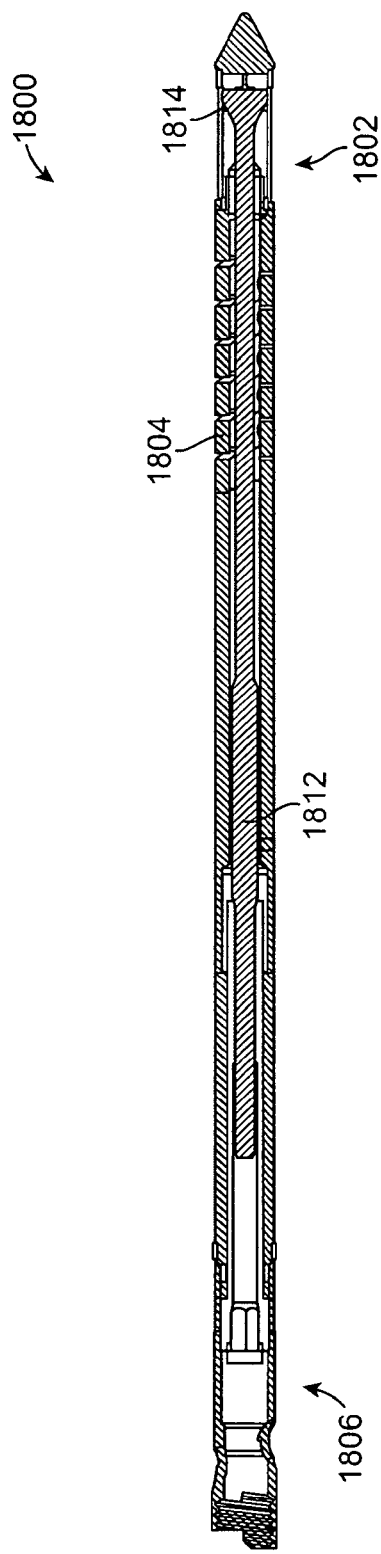
Figure 34:
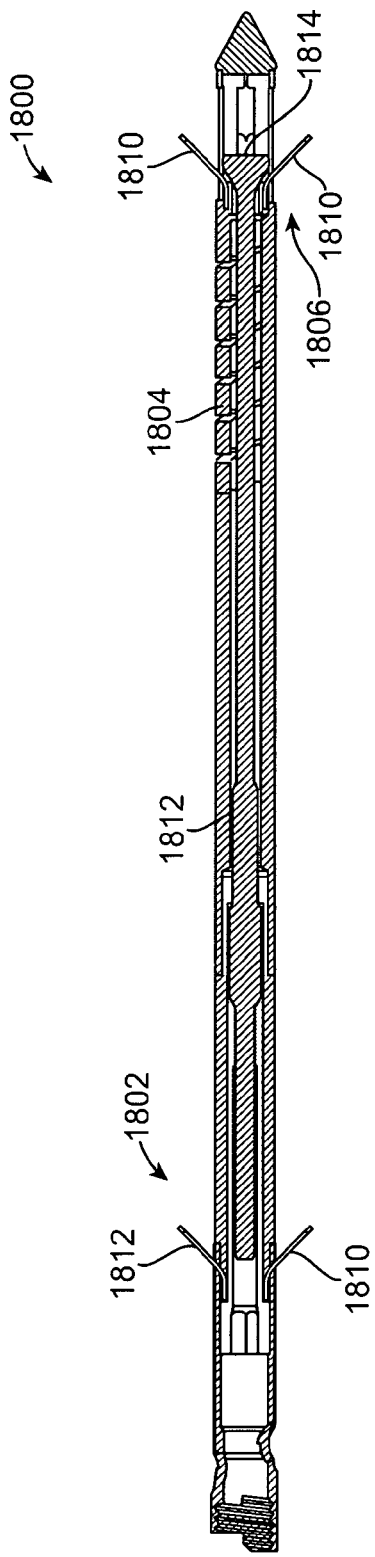
Figure 35:
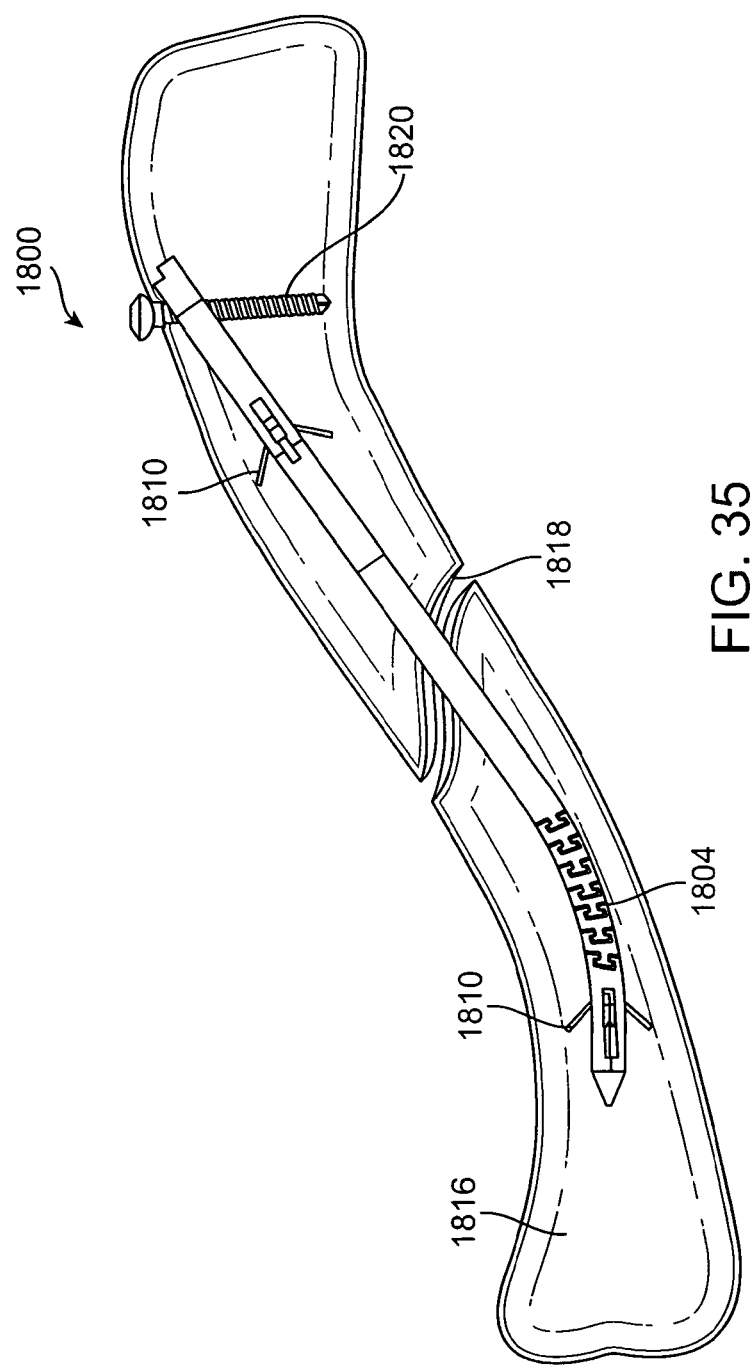
Figure 36:
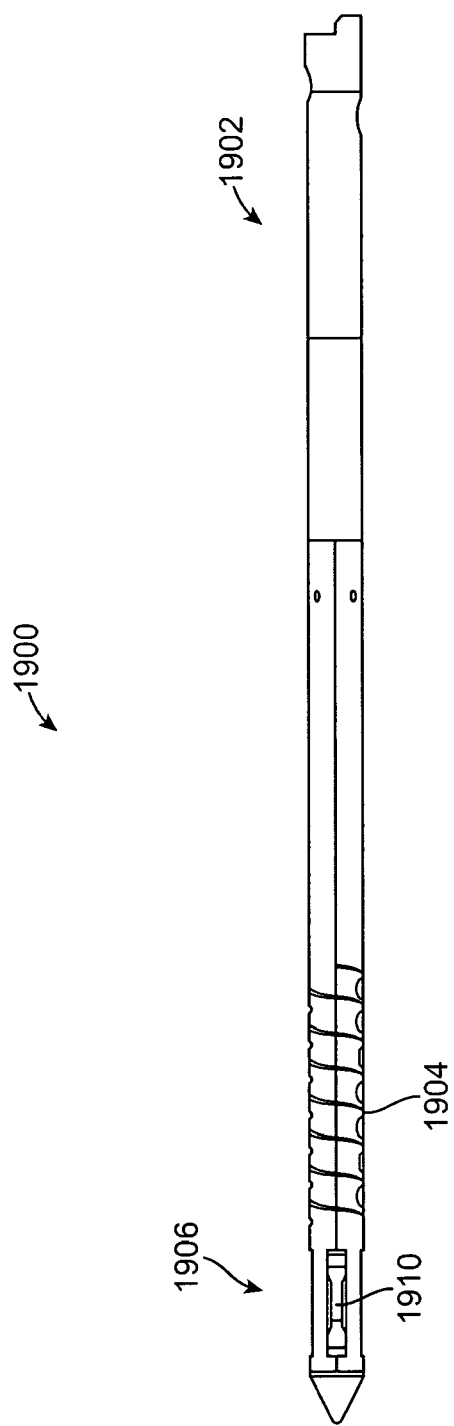
FIGS. 36-39 are various views showing another embodiment of a bone fixation device.

FIGS. 33 and 34 show cross-sections of device 1800, in which the actuator 1812 can be seen. The distal end of actuator rod 1812 is provided with a cam surface 1814 for outwardly deploying bendable arms 1810 of distal gripper 1806 from the retracted position shown in FIG. 33 to the deployed position shown in FIG. 34. FIG. 35 shows device 1800 implanted in clavicle bone 1816 across fracture 1818. One or more screws 1820 may be used to secure the proximal end of device 1800, as previously described.

Referring to FIGS. 36-39, another embodiment of a bone fixation device is shown. Device 1900 is similar in construction and operation to the previously described bone fixation devices. Device 1900 includes a straight hub 1902 at its proximal end, flexible-to-rigid body portion 1904, and distal gripper 1906. As can been seen in the figures, the single actuatable bone engaging gripper 1906 is disposed on the elongate body at a location distal to the flexible-to-rigid portion 1904 of the elongate body of device 1900. In this embodiment, single gripper 1906 includes four fan-like bendable arms 1910 similar to those previously described.

Figure 37:
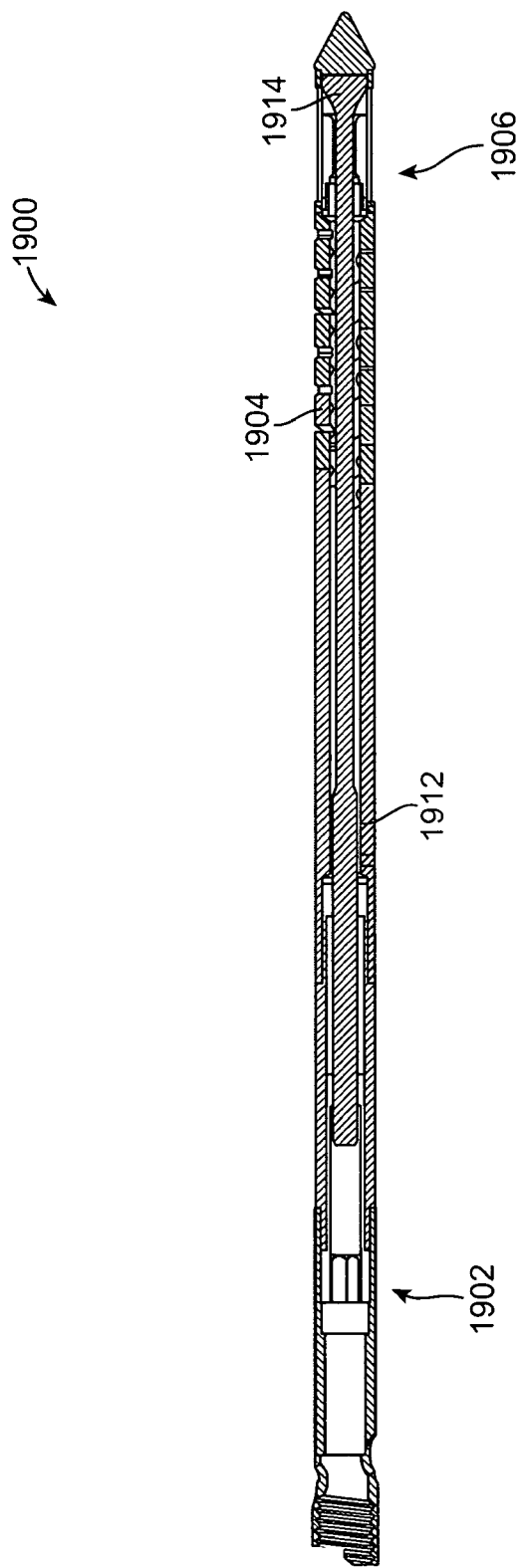
Figure 38:
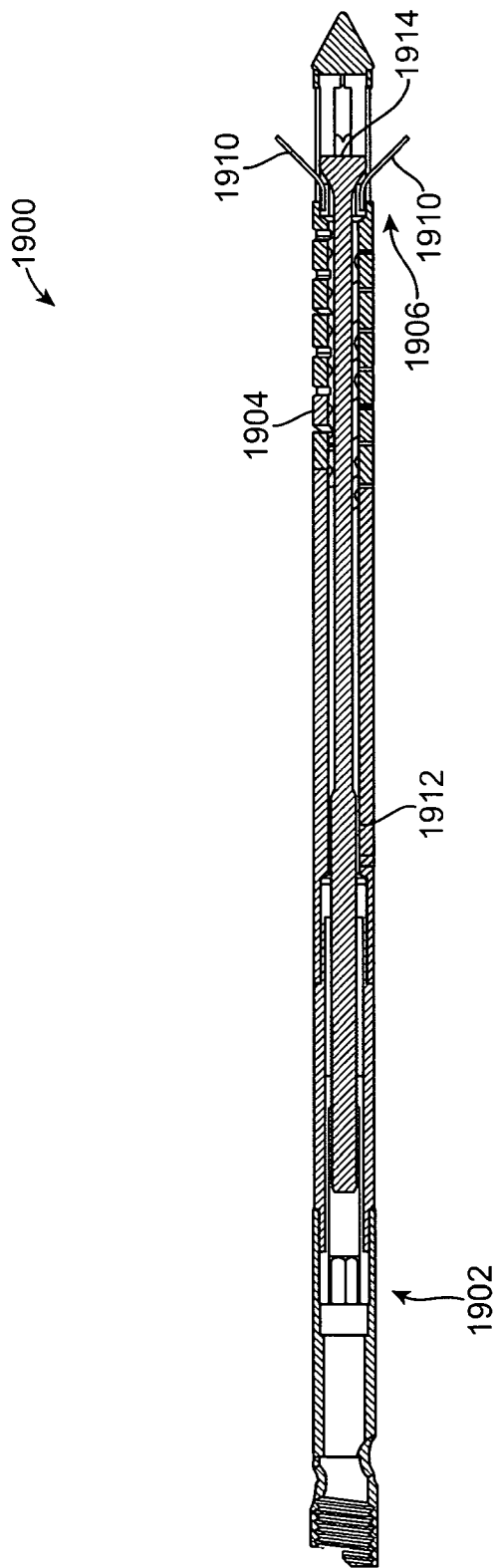
Figure 39:
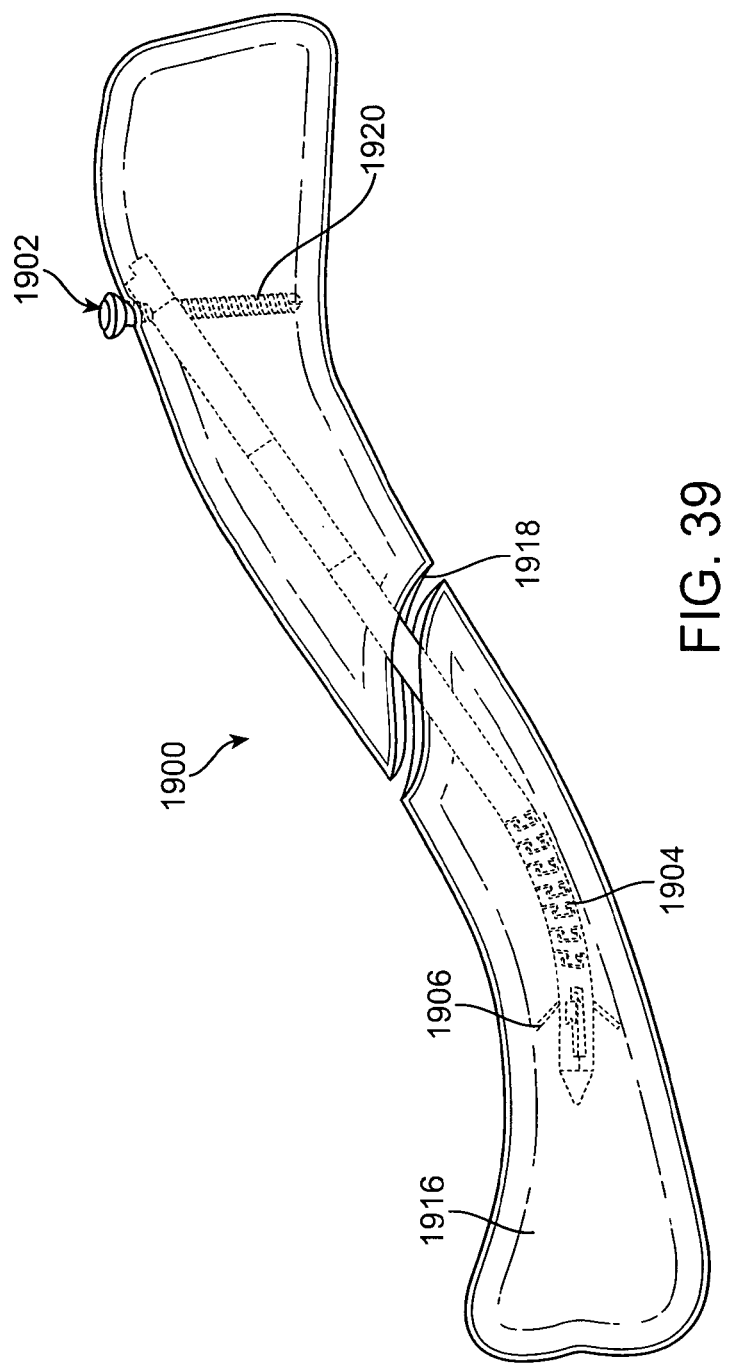

FIGS. 37 and 38 show cross-sections of device 1900, in which the actuator 1912 can be seen. The distal end of actuator rod 1912 is provided with a cam surface 1914 for outwardly deploying bendable arms 1910 of distal gripper 1906 from the retracted position shown in FIG. 37 to the deployed position shown in FIG. 38. FIG. 39 shows device 1900 implanted in clavicle bone 1916 across fracture 1918. One or more screws 1920 may be used to secure the proximal end of device 1900, as previously described.

Figure 40:
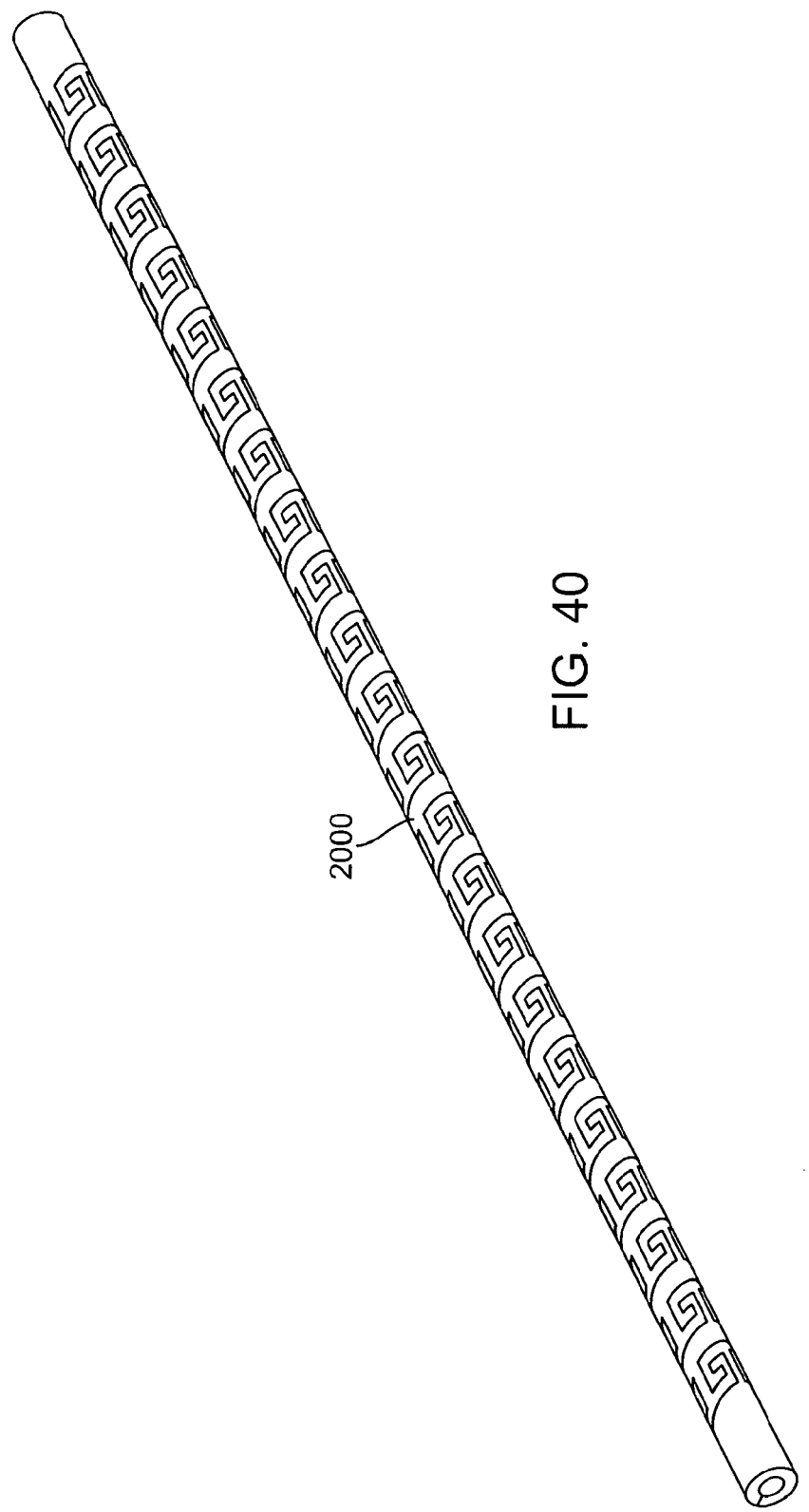
FIG. 40 is a perspective view showing another embodiment of a flexible-to-rigid body portion of a bone fixation device.
Figure 41:
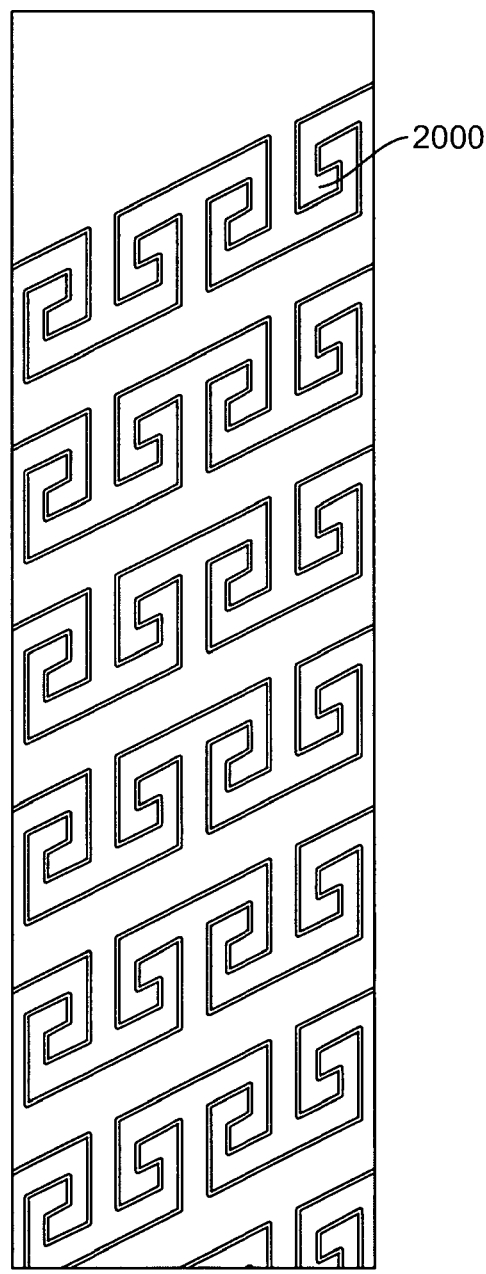
FIG. 41 is a plan view showing part of the cut pattern of the body portion of FIG. 40 laid flat.

Referring to FIGS. 40 and 41, another embodiment of a flexible-to-rigid body portion 2000 is shown. FIG. 40 shows a perspective view of body portion 2000 having a spiral cut formed through its tube wall. FIG. 41 shows a plan view of the cut pattern laid flat. Under axial compression, the extensions formed by the spiral cut collide, aiding in the rigidity of the construct.

Figure 42:
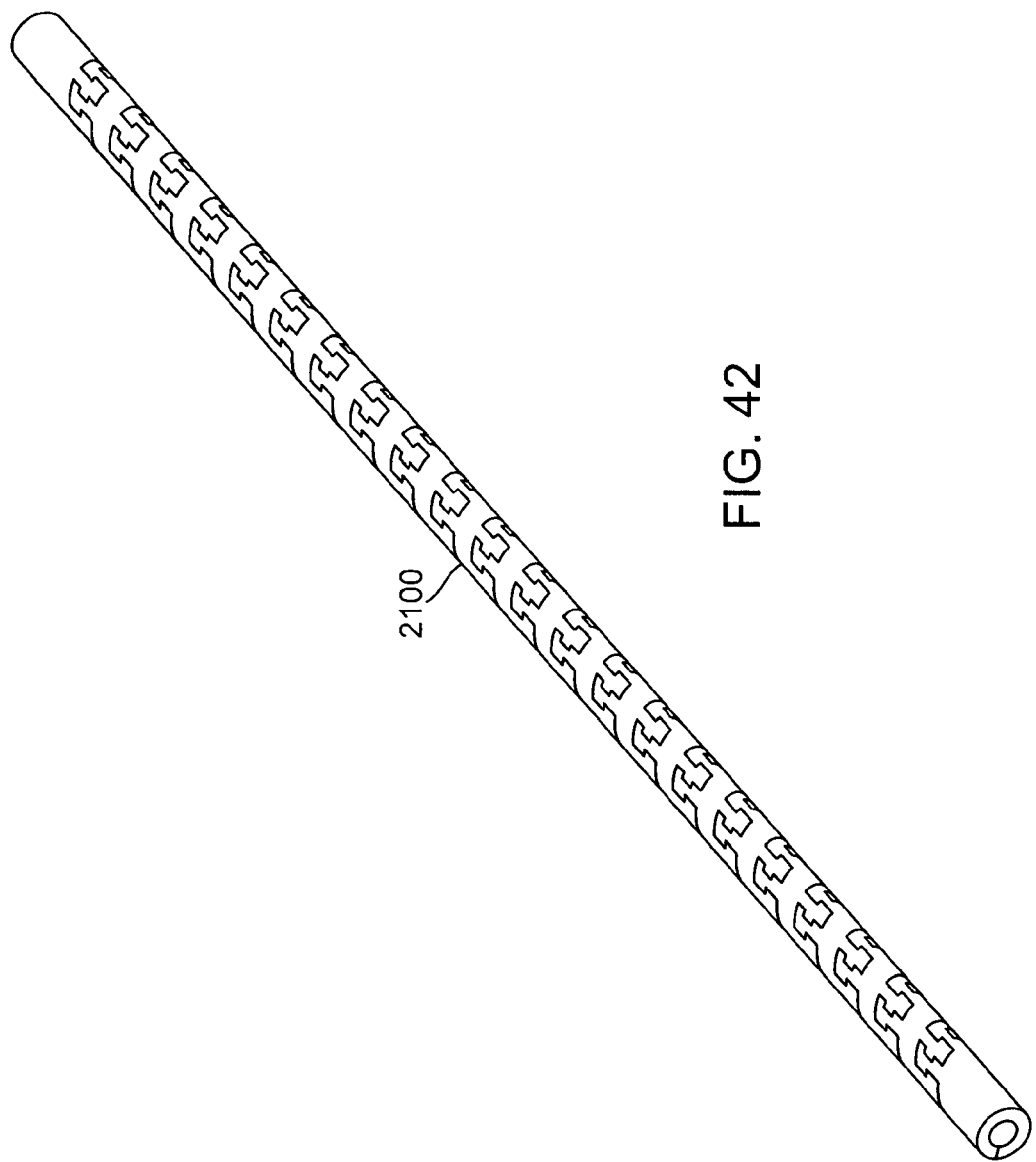
FIG. 42 is a perspective view showing another embodiment of a flexible-to-rigid body portion of a bone fixation device.
Figure 43A:
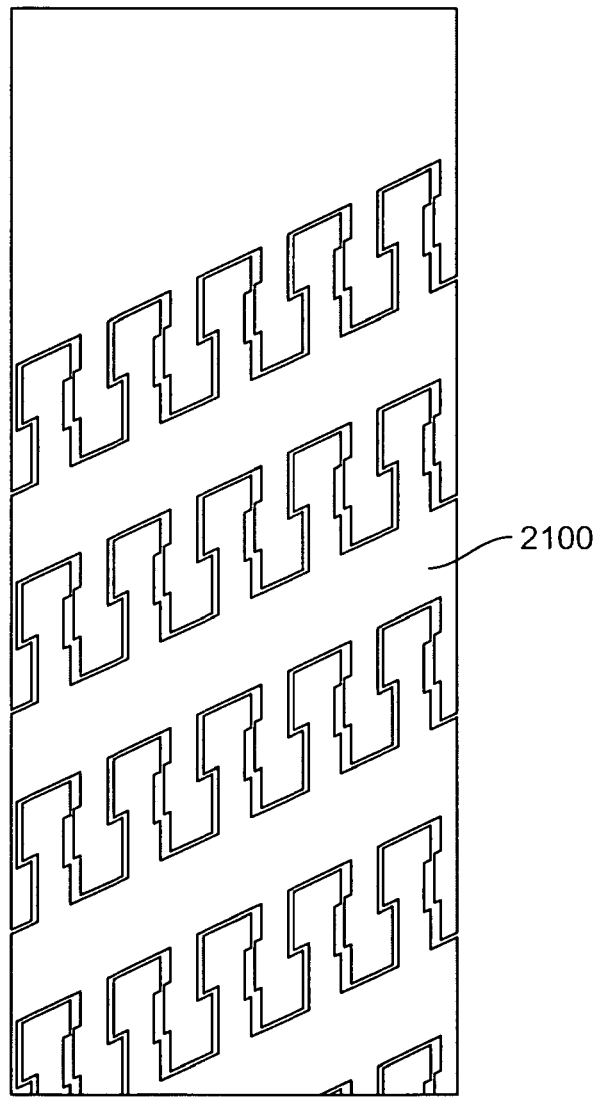
FIG. 43A is a plan view showing part of the cut pattern of the body portion of FIG. 42 laid flat.

Referring to FIGS. 42 and 43A, another embodiment of a flexible-to-rigid body portion 2100 is shown. FIG. 42 shows a perspective view of body portion 2100 having a spiral cut formed through its tube wall. FIG. 43A shows a plan view of the cut pattern laid flat. Axial compression causes the proximally and distally extending features to translate transverse to the longitudinal axis of the body portion 2100. This lateral movement causes keying features formed on the extending features to interengage, aiding in the rigidity of the construct.

Figure 43B:
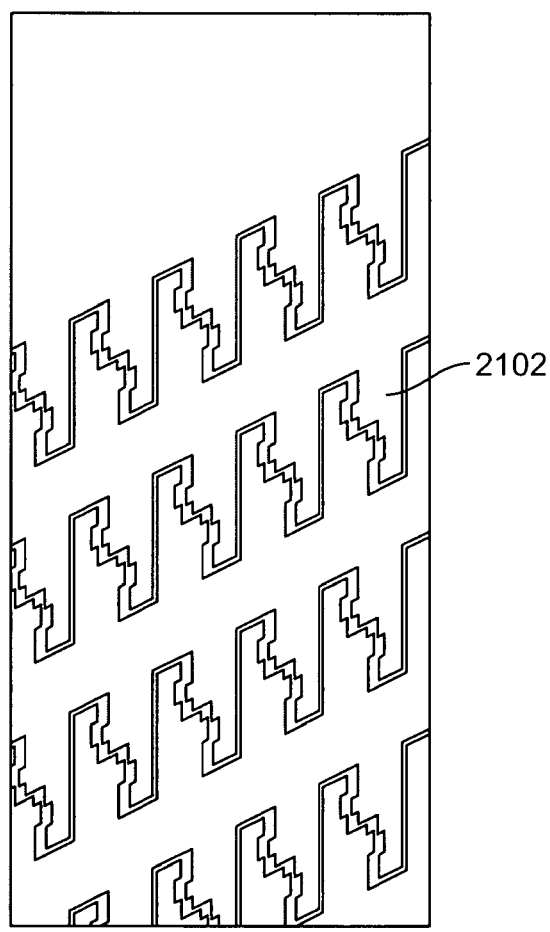
FIG. 43B is a plan view showing part of a cut pattern laid flat, similar to the one shown in FIGS. 42 and 43A.

Referring to FIG. 43B, another embodiment of a flexible-to-rigid body portion 2102 is shown in plan view, with the cut pattern laid flat. Like the pattern shown in FIG. 43A, axial compression causes the proximally and distally extending features to translate transverse to the longitudinal axis of the body portion 2102. This lateral movement causes keying features formed on the extending features to interengage, aiding in the rigidity of the construct.

Figure 44:
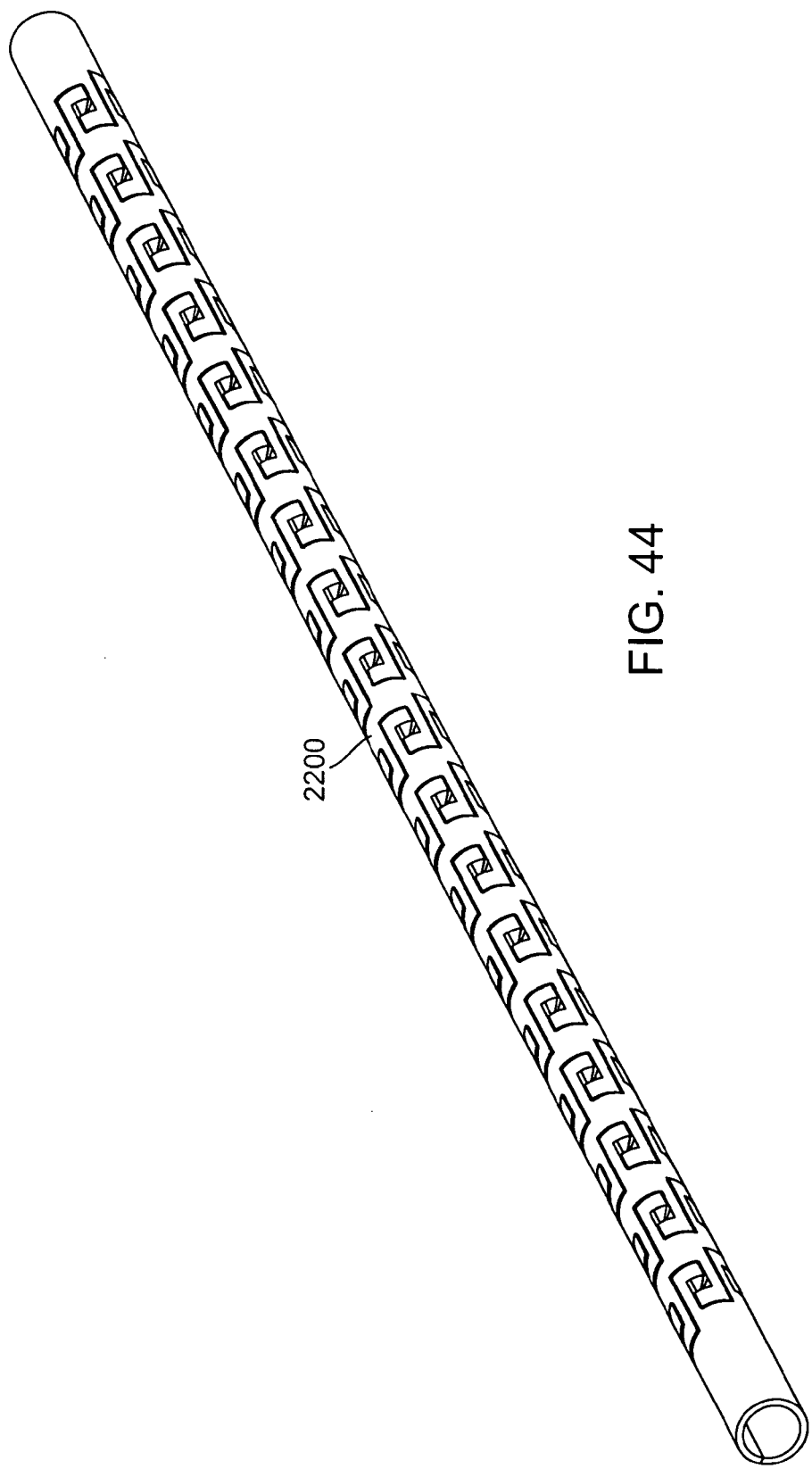
FIG. 44 is a perspective view showing another embodiment of a flexible-to-rigid body portion of a bone fixation device.
Figure 45:
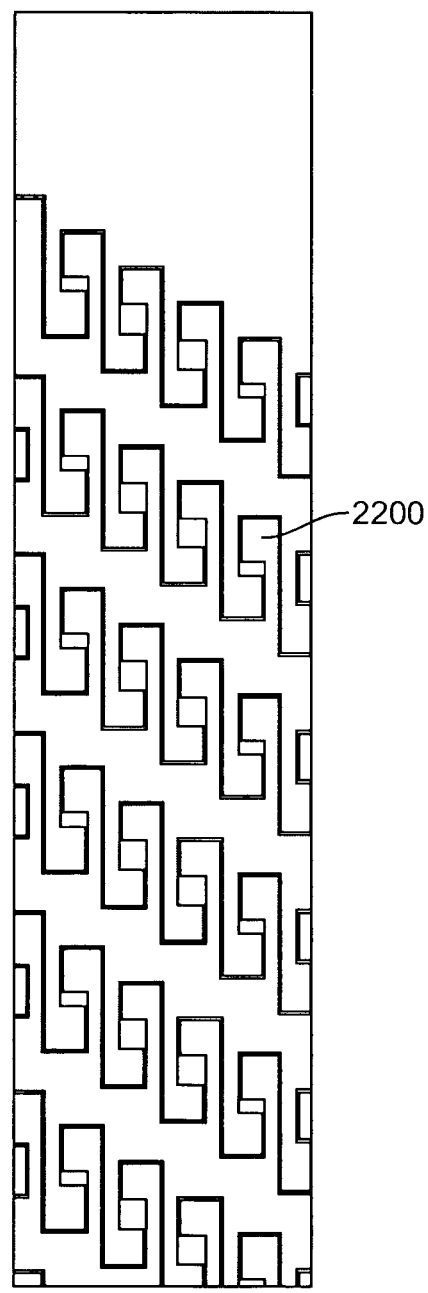
FIG. 45 is a plan view showing part of the cut pattern of the body portion of FIG. 44 laid flat.

Referring to FIGS. 44 and 45, another embodiment of a flexible-to-rigid body portion 2200 is shown. FIG. 44 shows a perspective view of body portion 2200 having a spiral cut formed through its tube wall. FIG. 45 shows a plan view of the cut pattern laid flat. The interlocking features of the spiral cut are transverse to the longitudinal axis of the body portion 2200. This maximizes contact surface in compression to aid in rigidity. The gap between the arms may be varied as shown to increase flexibility in one plane.

Figure 46:
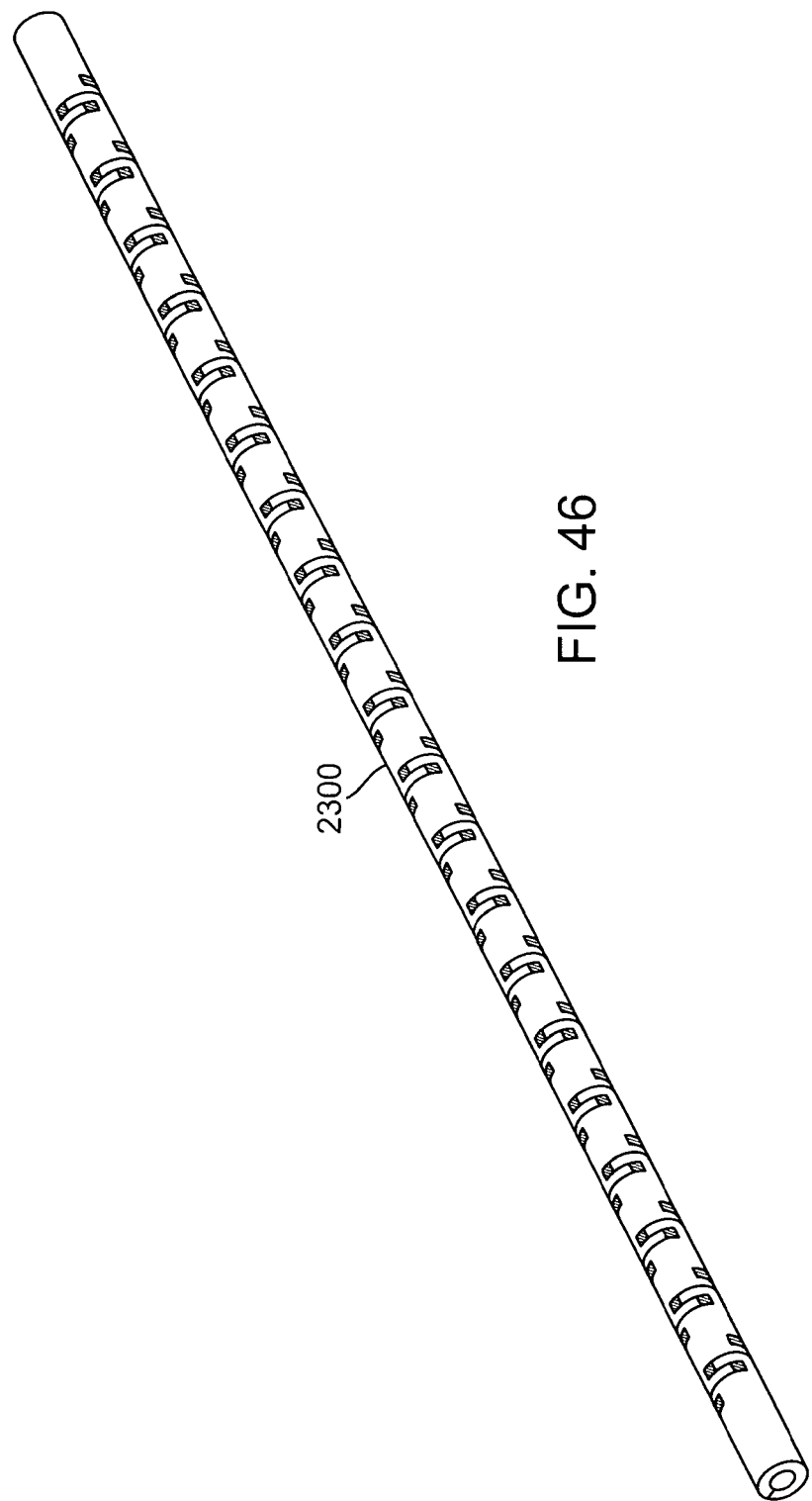
FIG. 46 is a perspective view showing another embodiment of a flexible-to-rigid body portion of a bone fixation device.
Figure 47:
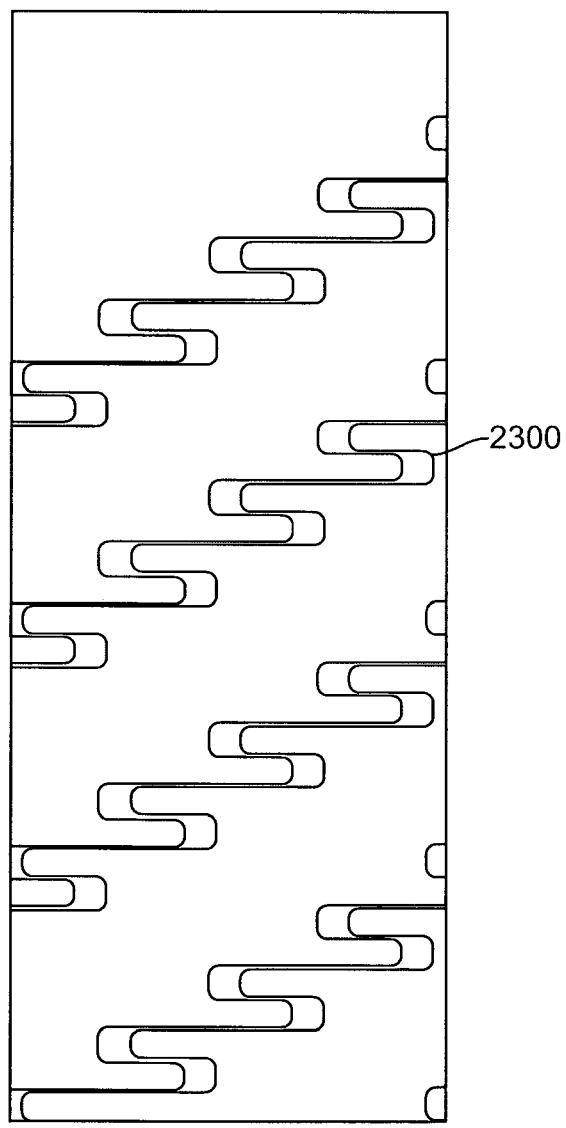
FIG. 47 is a plan view showing part of the cut pattern of the body portion of FIG. 46 laid flat.

Referring to FIGS. 46 and 47, another embodiment of a flexible-to-rigid body portion 2300 is shown. FIG. 46 shows a perspective view of body portion 2300 having a spiral cut formed through its tube wall. FIG. 47 shows a plan view of the cut pattern laid flat. The features of the spiral cut step horizontally, transverse to the longitudinal axis of the body portion 2200. This maximizes contact surface in compression. Varying gaps allow the body to twist more.

Figure 48:
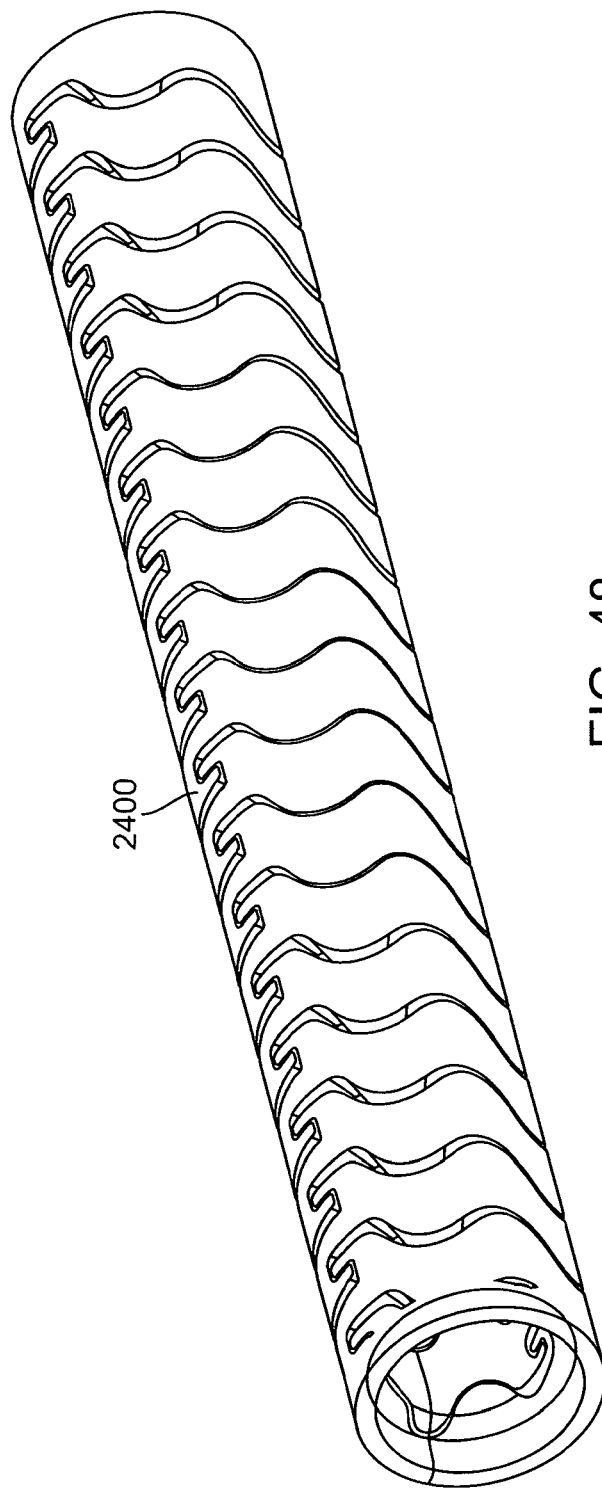
FIG. 48 is a perspective view showing another embodiment of a flexible-to-rigid body portion of a bone fixation device.
Figure 49:
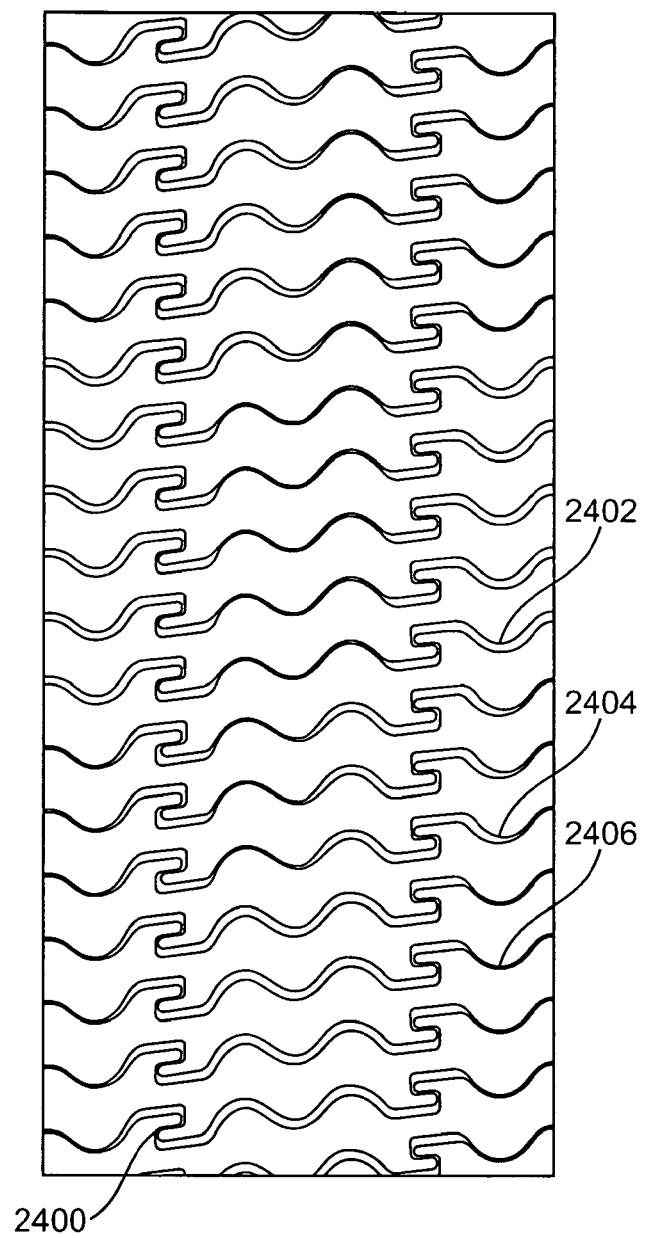
FIG. 49 is a plan view showing the cut pattern of the body portion of FIG. 48 laid flat.

Referring to FIGS. 48 and 49, another embodiment of a flexible-to-rigid body portion 2400 is shown. FIG. 48 shows a perspective view of body portion 2400 having a spiral cut formed through its tube wall. FIG. 49 shows a plan view of the cut pattern laid flat. The pattern of the spiral cut includes a sinusoidal wave interrupted by locking features. The gap formed by the cut can be varied longitudinally. For example, the gap at locations 2402, 2404 and 2406 can get progressively smaller as shown. When body portion 2400 is axially compressed, it forms a curve in each segment in which the gap is varied. The resulting shape is a curve which spirals down the length of the body, similar to the shape of a cork screw. In some embodiments, this shape aids the device in being able to grip the interior surfaces of the bone.

While exemplary embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. To the extent that any information that has been incorporated herein by reference conflicts with information in this application, the information in the present application takes precedent.

What is claimed is:

1. A bone fixation device comprising:
    an elongate body having a longitudinal axis and a flexible-to-rigid portion having a first state in which at least a portion of the body is flexible and a second state in which the body is generally rigid;
    a first actuatable bone engaging gripper disposed on the elongate body;
    a second actuatable bone engaging gripper disposed on the elongate body distal from the first gripper;
    a hub coupled to a proximal end of the elongate body; and
    an actuator operably connected to at least one of the first and the second grippers to actuate the gripper from a disengaged configuration to an engaged configuration, the first and the second grippers each having at least one bendable member, the member pivoting away from the longitudinal axis of the elongate body when the gripper is actuated, the actuator also being operably connected to the elongate body to change the elongate body from its flexible state to its rigid state,
    wherein the actuator comprises an actuator head comprising a ramped surface, wherein the actuator head is slideably disposed on an interior of the at least one of the first and the second grippers, the actuator head configured to outwardly actuate the at least one of the first and the second grippers away from the longitudinal axis;
    a second actuator, thereby allowing each of the two grippers to be independently actuated.

2. The bone fixation device of claim 1, wherein the flexible-to-rigid portion of the elongate body is disposed at a location on the elongate body distal to the first gripper and proximal to the second gripper.

3. The bone fixation device of claim 2 wherein the hub is straight.

4. The bone fixation device of claim 2 wherein the hub is curved.

5. The bone fixation device of claim 2 wherein the actuator and the second actuator are connected to actuate both grippers from a disengaged configuration to an engaged configuration.

6. A surgical kit comprising:
    the bone fixation device of claim 1; and
    an alignment tool configured to couple to the hub, the tool further configured to align with a portion of the device to form at least one screw hole into the portion of the device.

7. The surgical kit of claim 6 wherein the alignment tool is configured to align with at least the hub of the device to form a screw hole in the hub.

8. The surgical kit of claim 6 wherein the alignment tool is configured to align with at least the flexible-to-rigid portion of the device to form a screw hole in that portion.

9. The bone fixation device of claim 1, wherein the flexible-to-rigid portion of the elongate body is disposed at a location on the elongate body distal to both the first and the second grippers.

10. The bone fixation device of claim 9 wherein the hub is straight.

11. The bone fixation device of claim 9 wherein the hub is curved.

12. A surgical kit comprising:
    the bone fixation device of claim 9; and
    an alignment tool configured to couple to the hub, the tool further configured to align with a portion of the device to form at least one screw hole into the portion of the device.

13. The surgical kit of claim 12 wherein the alignment tool is configured to align with at least the hub of the device to form a screw hole in the hub.

14. The surgical kit of claim 12 wherein the alignment tool is configured to align with at least the flexible-to-rigid portion of the device to form a screw hole in that portion.

15. A bone fixation device comprising:
    a generally tubular body having a circumferential surface, an inner lumen, and a wall extending therebetween, and an actuatable bone engaging gripper disposed on the wall, the body being sized to fit within an intramedullary space within a bone, the body having a longitudinal axis;
    the gripper having at least one bendable member, the member pivoting away from the longitudinal axis of the tubular body when the gripper is actuated,
    an actuator operably connected to the gripper to actuate the gripper from a disengaged configuration to an engaged configuration,
    wherein the actuator comprises an actuator head comprising a ramped surface, wherein the actuator head is slideably disposed in the inner lumen, the actuator head configured to outwardly actuate the gripper away from the longitudinal axis,
    a helical slit through the body wall extending around the circumferential surface and axially along at least a portion of the body; and
    a compression mechanism configured to apply an axial compression to the body to move the slit towards a closed position, thereby transforming the body from a generally flexible state to a generally rigid state,
    wherein the helical slit forms multiple pairs of mating features, each pair having a proximally projecting member and a distally projecting member, the proximally projecting member having a ramped surface on its proximally facing end of sufficient angle to cause the proximally projecting member to move in a first generally transverse direction when under axial compression, the distally projecting member having a ramped surface on its distally facing end of sufficient angle to cause the distally projecting member to move in a second generally transverse direction generally opposite the first direction when under axial compression such that the projecting members of a pair move toward each other when under axial compression.

16. The bone fixation device of claim 15 wherein at least one of the projecting members of a pair comprises a laterally projecting keying feature that interengage with a keying feature of the opposite member of the pair when the members of the pair move toward each other.

17. The bone fixation device of claim 15 wherein at least one of the projecting members of a pair comprises a plurality of laterally projecting keying features that interengage with keying features of the opposite member of the pair when the members of the pair move toward each other.

18. The bone fixation device of claim 15 wherein each of the projecting members of a pair has a plurality of laterally projecting keying features that interengage with the keying features of the opposite member of the pair when the members of the pair move toward each other.

19. The bone fixation device of claim 17 wherein at least one of the plurality of laterally projecting keying features is nested on another of the laterally projecting keying features.

20. The bone fixation device of claim 15 further comprising at least two pairs of mating features located within one revolution of the helical slit.

21. The bone fixation device of claim 15 further comprising at least five pairs of mating features located within one revolution of the helical slit.

* * * * *